US 9,005,631 B2

(12) United States Patent
Berkower

(10) Patent No.: US 9,005,631 B2
(45) Date of Patent: Apr. 14, 2015

(54) MEMBRANE PROXIMAL REGION OF HIV GP41 ANCHORED TO THE LIPID LAYER OF A VIRUS-LIKE PARTICLE VACCINE

(75) Inventor: Ira Berkower, Washington, DC (US)

(73) Assignee: The United States of America as Represented by the Secretary of the Department of Health and Human Services, Washington, DC (US)

(*) Notice: Subject to any disclaimer, the term of this patent is extended or adjusted under 35 U.S.C. 154(b) by 747 days.

(21) Appl. No.: 13/057,414

(22) PCT Filed: Aug. 4, 2009

(86) PCT No.: PCT/US2009/052724
§ 371 (c)(1),
(2), (4) Date: Feb. 3, 2011

(87) PCT Pub. No.: WO2010/017209
PCT Pub. Date: Feb. 11, 2010

(65) Prior Publication Data
US 2011/0142869 A1 Jun. 16, 2011

Related U.S. Application Data

(60) Provisional application No. 61/086,098, filed on Aug. 4, 2008.

(51) Int. Cl.
*A61K 39/00* (2006.01)
*A61K 39/12* (2006.01)
(Continued)

(52) U.S. Cl.
CPC ........... *A61K 39/292* (2013.01); *A61K 39/21* (2013.01); *C07K 14/005* (2013.01);
(Continued)

(58) Field of Classification Search
None
See application file for complete search history.

(56) References Cited

U.S. PATENT DOCUMENTS 6,585,979 B1 * 7/2003 Berman ...................... 424/208.1
2007/0099262 A1 * 5/2007 Anderson et al. ............ 435/69.1

FOREIGN PATENT DOCUMENTS

WO    WO8907140    * 10/1989
WO    WO 98/20036    * 5/1998
(Continued)

OTHER PUBLICATIONS

Sheu et al., 1995 Deletion or alteration of hydrophobic amino acids at the first and the third transmembrane domains of hepatitis B suface antigen enhances its in production in *Escherichia coli*. Gene 160(2):179-84.*

(Continued)

*Primary Examiner* — Zachariah Lucas
*Assistant Examiner* — Stuart W Snyder
(74) *Attorney, Agent, or Firm* — Klarquist Sparkman, LLP

(57) ABSTRACT

Disclosed herein are isolated immunogens including variant hepatitis B surface antigens (HBsAgs). In an example, a variant HBsAg includes a HBsAg with one or more transmembrane domains of the HBsAg replaced with a gp41 antigenic insert. The antigenic insert can include an antigenic polypeptide fragment of gp41 including the membrane proximal region of gp41 and a transmembrane membrane region of gp41. The replacement of a membrane spanning domain of HBsAg with a membrane spanning domain of gp41 anchors gp41 into HBsAg in virtually the identical orientation as on HIV virions and correctly orients the nearby MPR on the lipid layer. Thus, the disclosed variant HBsAgs display the neutralization-sensitive MPR in association with a lipid layer, while presenting it at the most immunogenic site on HBsAg. Also disclosed are uses of these variant HBsAgs, and nucleic acids encoding variant HBsAgs, such as to induce an immune response to HIV-1.

12 Claims, 16 Drawing Sheets

(51) Int. Cl.
A61K 39/21 (2006.01)
A61K 39/29 (2006.01)
C07K 14/005 (2006.01)

(52) U.S. Cl.
CPC .... *A61K 2039/5258* (2013.01); *A61K 2039/64* (2013.01); *C07K 2319/03* (2013.01); *C12N 2730/10122* (2013.01); *C12N 2730/10134* (2013.01); *C12N 2740/15022* (2013.01); *C12N 2740/15034* (2013.01); *C12N 2740/16222* (2013.01)

(56) References Cited

FOREIGN PATENT DOCUMENTS

| WO | WO 2006/112929 A2 | * | 2/2006 | ............ C12N 15/62 |
| WO | WO 2006/112929 | | 10/2006 | |
| WO | WO2006112929 | * | 10/2006 | |

OTHER PUBLICATIONS

BAA02128: HIV1 truncated transmembrane glycoprotein sequence, published 1992.*
P03435.1: Influenza HA Signal peptide/leader sequence, published 1980.*
Sieling et al.,2003. Toll-like Receptor 2 ligands as adjuvants for Human Th1 responses. J. Immunol 2003; 170: 194-200.*
Barouch et al., 2008. Challenges in the development of an HIV1 vaccine. Nature. vol. 455/2 October. 613-619.*
Hoot et al., 2013. Recombinant HIV envelope proteins fail to engage germline versions of anti-CD4bs bNAbs. PLOS pathogens. vol. 9, Issue 1, e1003106, p. 1-14.*
GenBank P30019.1 (Created 1993) TM-1 domain identified in HBsAg.*
Lenz et al., 2005. Trimeric Membrane Anchored gp41 inhibits HIV membrane fusion. J.Biol.Chem. vol. 280 (6), 4095-4101.*
Barouch, D.A. Challenges in the development of an HIV-1 vaccine. Nature, 2008 455(7213: 613-619.*
Hoot et al., Recombinant HIV Envelope Proteins Fail to Engage Germline Versions of Anti-CD4bs bNAbs. PLoS Pathogens, 2013; 9(1) e1003106:1-14.*
Norder, et al. Genetic relatedness of hepatitis B viral strains of diverse geographical origin and natural variations in the primary structure of the surface antigen. J. Gen. Virol. 1993; 74(7): 1341-1348.*
Michel, et al. Optimisation of secretion of recombinant HBsAg virus-like particles: Impact on the development of HIV-1/HBV bivalent vaccines. Vaccine, 2007; 25: 1901-1907.*
Sheu and Lo, Deletion or alteration of hydrophobic amino acids at the first and the third transmembrane domains of hepatitis B surface antigen enhances its production in *Escherichia coli*. Gene. 1995; 160: 179-184.*
Lenz, et al. Trimeric Membrance-anchored gp41 Inhibits HIV Membrane Fusion. J. Biol. Chem. 2005; 280(6): 4095-4101.*
GenBank submission AEM27707; 1993.*
GenBank submission BAA 02128; 2003.*
Shimizu, et al. Analysis of a human immunodeficiency virus type 1 isolate carrying a truncated transmembrane glycoprotein. Virology. 1992; 189(2): 534-546.*
Min Jou, et al. Complete structure of the hemagglutinin gene from the human influenza A/Victoria/3/75 (H3N2) strain as determined from cloned DNA. Cell, 1980; 19: 683-696.*
McQueen, et al. Chimeric influenza virus hemagglutinin containing either the NH2 terminus or the COOH terminus of G protein of vesicular stomatitis virus is defective in transport to the cell surface. Proc. Natl. Acad. Sci., USA 1984; 81: 395-399.*
Eckhart, et al. Immunogenic presentation of a conserved gp41 epitope of human immunodeficiency virus type 1 on recombinant surface antigen of hepatitis B virus. J. Gen. Virol. 1996; 77: 2001-2008.*
Muster, et al. Mucosal Model of Immunization against Human Immunodeficiency Virus Type 1 with a Chimeric Influenza Virus. J. Virol. 1995; 69(11): 6678-6686.*
Eckhart et al., "Immunogenic presentation of a conserved gp41 epitope of human immunodeficiency virus type 1 on recombinant surface antigen of hepatitis B virus," *Journal of General Virology*, vol. 77, pp. 2001-2008, 1996.
Michel et al., "T- and B-Lymphocyte Responses to Human Immunodeficiency Virus (HIV) Type 1 in Macaques Immunized with Hybrid HIV/Hepatitis B Surface Antigen Particles," *Journal of Virology*, vol. 64, No. 5, pp. 2452-2455, 1990.
Patterson et al., "Formation of HIV-1 Envelope-Hepatitis B Core Antigen Hybrids with High Affinity for CD4," *Biochemical and Biophysical Research Communications*, vol. 285, pp. 639-643, 2001.
Phogat et al., "Analysis of the Human Immunodeficiency Virus Type 1 gp41 Membrane Proximal External Region Arrayed on Hepatitis B Surface Antigen Particles," *Virology*, vol. 373, No. 1, pp. 72-84, 2008.
Zwick et al., "Broadly Neutralizing Antibodies Targeted to the Membrane-Proximal External Region of Human Immunodeficiency Virus Type 1 Glycoprotein gp41," *Journal of Virology*, vol. 75, No. 22, pp. 10892-10905, 2001.
Berkower et al., "Hepatitis B Virus Surface Antigen Assembly Function Persists when Entire Transmembrane Domains 1 and 3 are Replaced by a Heterologous Transmembrane Sequence," *Journal of Virology*, vol. 85, No. 5, pp. 2439-2448, Mar. 2011.
Extended European Search Report issued Feb. 24, 2012 by the European Patent Office for corresponding European Patent Application No. 09805448.9, filed Aug. 4, 2009, 4 pp.
Patient et al., "Chimeric hepatitis B and C viruses envelope proteins can form subviral particles: implications for the design of new vaccine strategies," *New Biotechnology*, vol. 24, No. 4, pp. 226-234, Apr. 1, 2009.

* cited by examiner

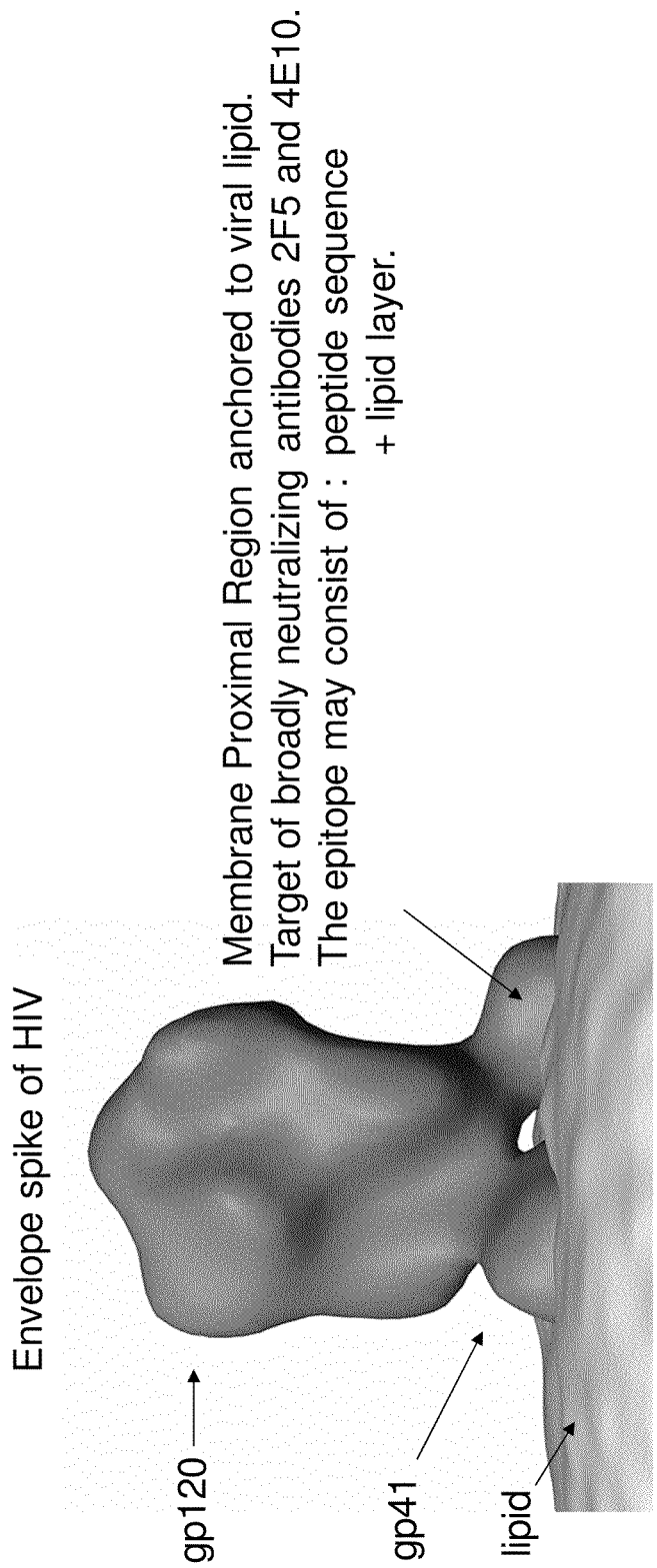

TM12    TM14    TM16

FIG. 6
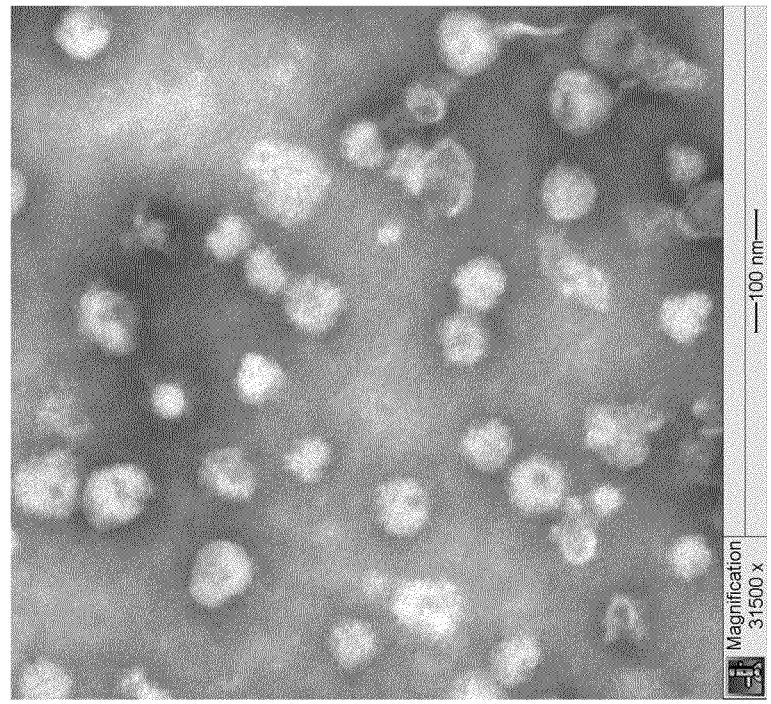
TM20
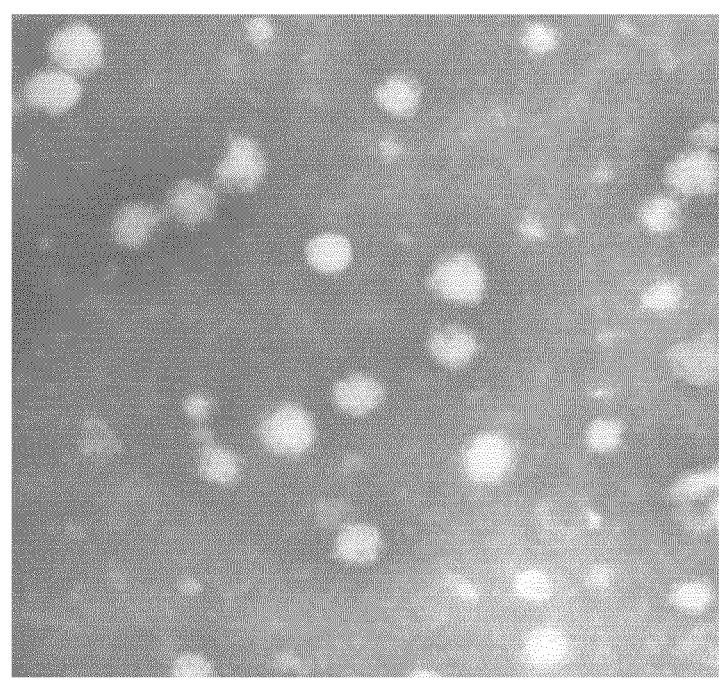
TM16

FIG. 7
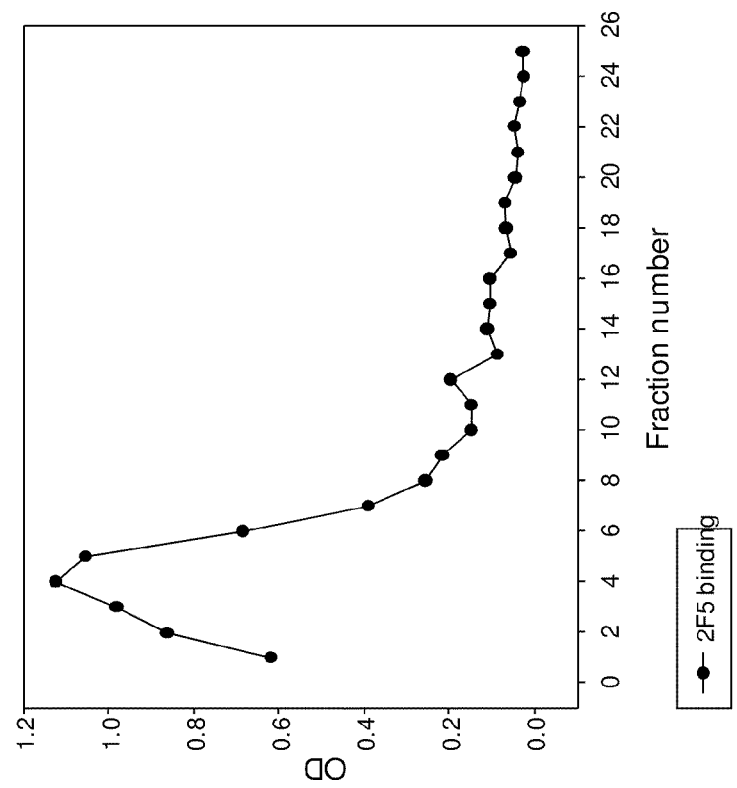
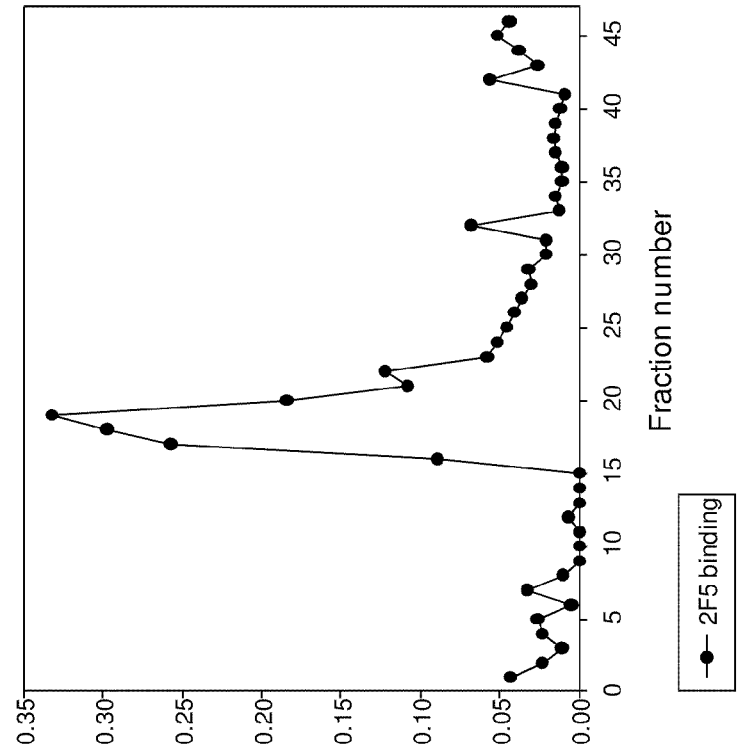

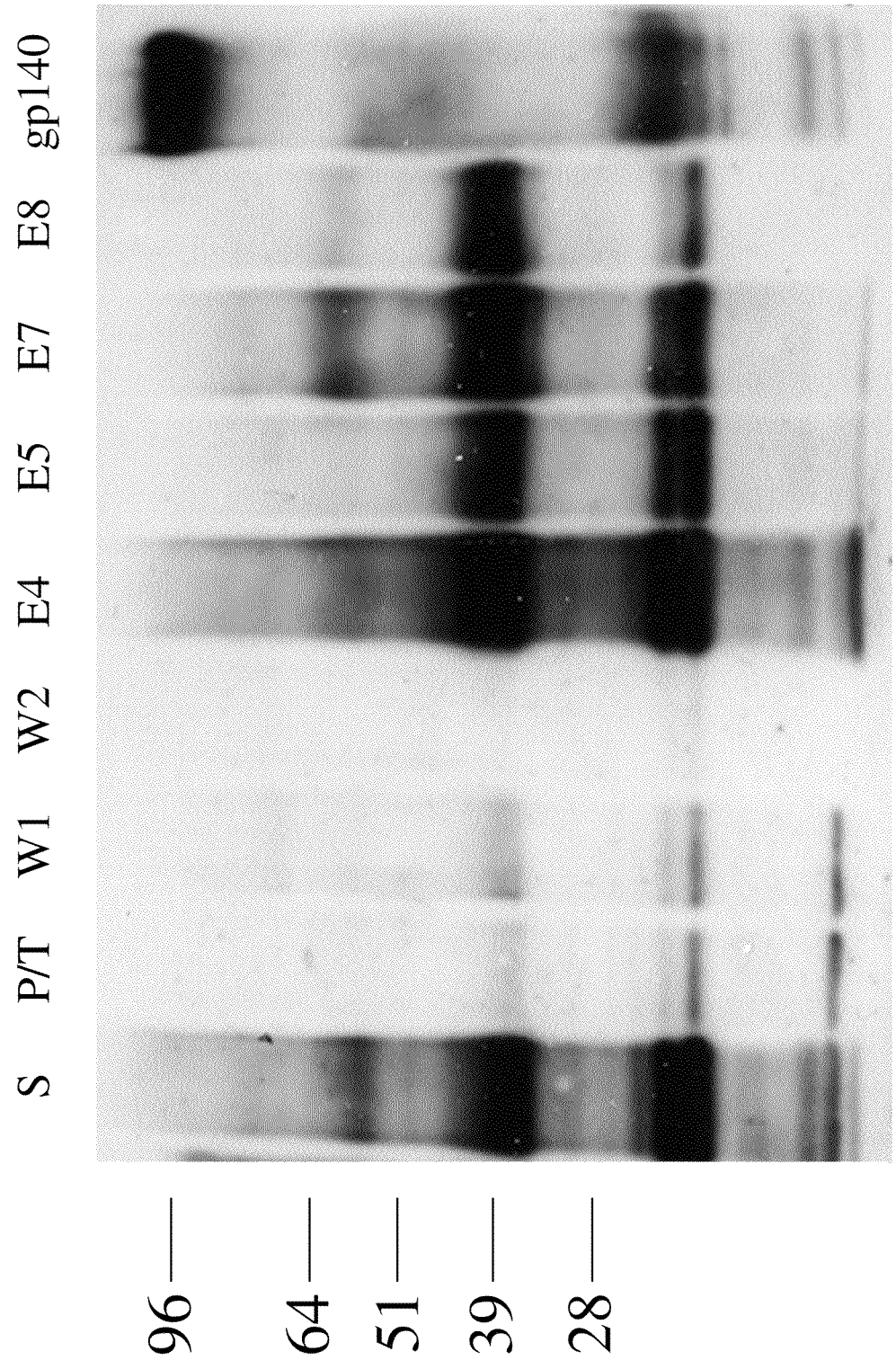

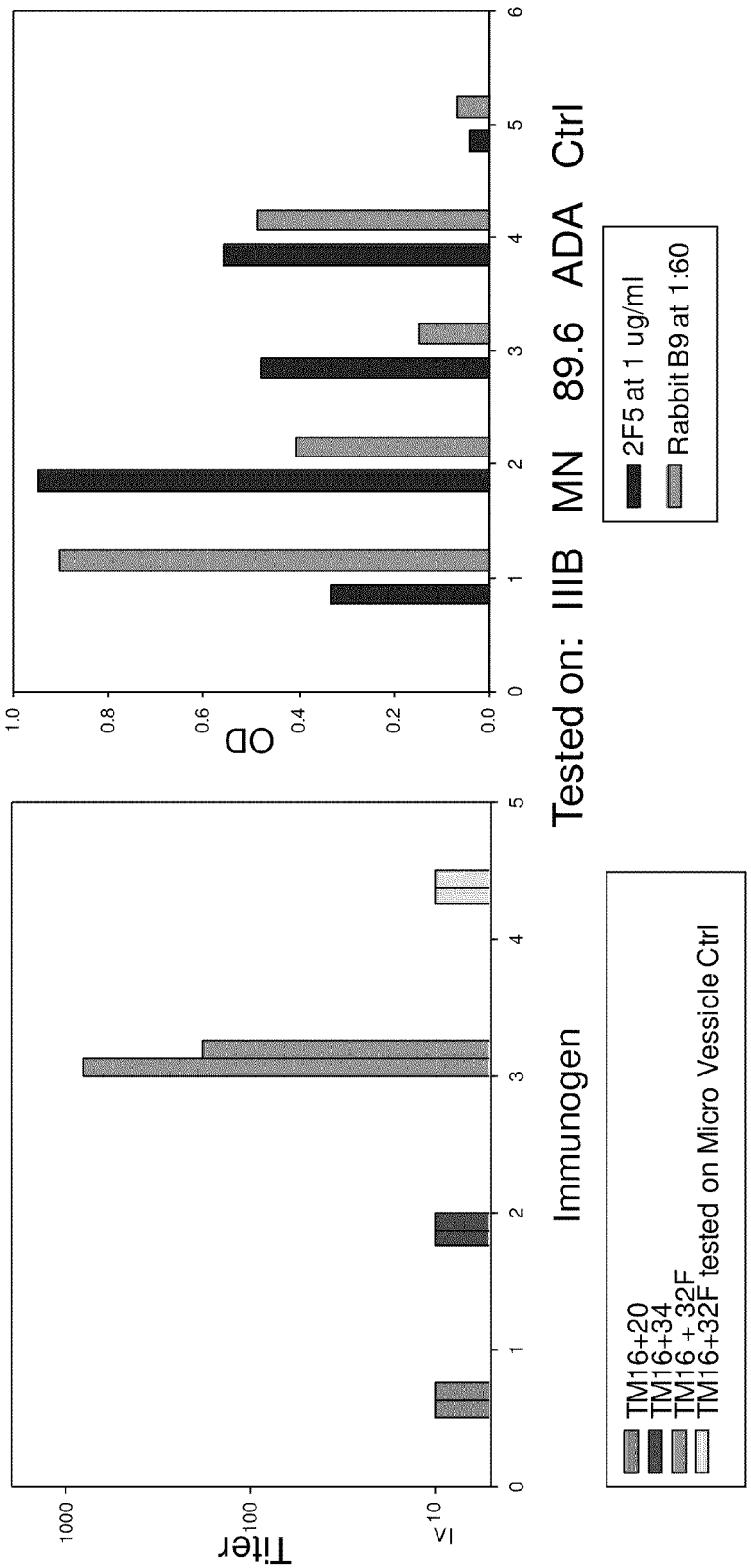

MEMBRANE PROXIMAL REGION OF HIV GP41 ANCHORED TO THE LIPID LAYER OF A VIRUS-LIKE PARTICLE VACCINE

CROSS REFERENCE TO RELATED APPLICATION

This is the §371 U.S. National Stage of International Application No. PCT/US2009/052724, filed on Aug. 4, 2009, which was published in English under PCT Article 21(2), which in turn claims the benefit of U.S. Provisional Application No. 61/086,098, filed Aug. 4, 2008, which is incorporated herein by reference in its entirety.

FIELD

This disclosure relates to the field of human immunodeficiency virus, specifically to the use of epitopes of glycoprotein 41 (gp41) to induce an immune response, including a protective immune response.

BACKGROUND

Acquired immune deficiency syndrome (AIDS) is recognized as one of the greatest health threats facing modern medicine. Treatments for human immunodeficiency virus (HIV)-infected individuals as well as the development of vaccines to protect against infection are urgently needed. One difficulty has been in eliciting neutralizing antibodies to the virus.

The HIV-1 envelope glycoproteins (gp120-gp41), which mediate receptor binding and entry, are the major targets for neutralizing antibodies. Although the envelope glycoproteins are immunogenic and induce a variety of antibodies, the neutralizing antibodies that are induced are strain-specific, and the majority of the immune response is diverted to non-neutralizing determinants (Weiss, R. A., et al., *Nature,* 316 (6023): 69-72, 1985; Wyatt, R. and J. Sodroski, *Science,* 280 (5371): 1884-1888, 1998). Broadly neutralizing antibodies have been isolated only rarely from natural HIV infection, as only five broadly-neutralizing antibodies have been identified to date. Three are gp41-directed (2F5, 4E10 and Z13) and the other two (b12 and 2G12) are gp120-directed. The three gp41 neutralizing antibodies recognize the membrane proximal region (MPR) of the HIV-1 gp41 glycoprotein. The MPR region includes a series of amino acids that lie on the HIV vsurface, just before gp41 crosses the viral membrane. The MPR is highly hydrophobic (50% of residues are hydrophobic), and is highly conserved across many HIV clades (Zwick, M. B., et al., *J Virol,* 75 (22): 10892-10905, 2001). Recently the hydrophobic context of MPR and the presence of lipid membrane were shown to be important for the optimal binding of 2F5 and 4E10 antibodies (Ofek, G., et al., *J Virol,* 78 (19): 10724-37, 2004).

To date, immunization with conserved membrane proximal elements or the core 2F5 epitope in a number of contexts has failed to elicit broadly neutralizing antibodies (Coeffier, E., et al., *Vaccine,* 19 (7-8): 684-693, 2000; Eckhart, L., et al., *J Gen Virol,* 77 (Pt 9): 2001-2008, 1996; Ernst, W., et al., *Nucleic Acids Res,* 26 (7): 1718-1723, 1998; Ho, J., et al., *Vaccine,* 20 (7-8): 1169-1180, 2002; Liang, X., et al., *Epitop Vaccine,* 17 (22): 2862-2872, 1999; Liao, M., et al., *Peptides,* 21 (4): 463-468, 2000; Xiao, Y., et al., *Immunol Invest,* 29 (1): 41-50, 2000). Thus, there remains a need to identify HIV antigens that can be used to induce a protective immune response.

SUMMARY

Historically, compositions used to produce an immune response against viral antigens included live-attenuated or chemically inactivated forms of the virus. However, this approach has limited utility when used for human immunodeficiency virus. Disclosed herein is the use of the immunogenic hepatitis B surface antigen (HBsAg) platform to array epitopes from the conserved, neutralization-sensitive membrane proximal region (MPR) of HIV-1, and the use of this platform to induce an immune response to HIV-1.

In one embodiment, isolated immunogens including variant HBsAgs are disclosed. In an example, a variant HBsAg includes an HBsAg with one or more transmembrane domains of the HBsAg replaced with a gp41 transmembrane domain and/or one or more gp41 MPRs. For example, a variant HBsAg can include a gp41 antigenic insert that includes an antigenic polypeptide fragment of gp41 including the MPR of gp41 and a transmembrane domain of gp41. The replacement of a membrane spanning domain of HBsAg with a membrane spanning domain of gp41 anchors gp41 into HBsAg in virtually the identical orientation as on HIV virions and correctly orients the nearby MPR on the lipid layer. Thus, the disclosed variant HBsAgs display the neutralization-sensitive MPR in association with a lipid layer, while presenting it at the most immunogenic site on HBsAg. Also disclosed are uses of these variant HBsAgs, and nucleic acids encoding variant HBsAgs, such as to induce an immune response to HIV-1.

In some embodiments, an isolated immunogen includes a variant HBsAg with one or more transmembrane domains of the HBsAg replaced with a gp41 antigenic insert. The gp41 antigenic insert includes (a) an antigenic polypeptide fragment of gp41, such as an antigenic polypeptide gp41 fragment with the amino acid sequence of SEQ ID NO: 1, and (b) a transmembrane domain of gp41, such as a transmembrane spanning gp41 region with the amino acid sequence set forth in SEQ ID NO: 25 (in which $X_1, X_2, X_3,$ and $X_4$ are any amino acid and $X_5, X_6,$ and $X_7$ are any hydrophobic amino acid). In one example, the antigenic polypeptide fragment of gp41 is between 28 and 150 amino acids in length and the membrane spanning region of gp41 is between 22 and 40 amino acids in length.

In one particular embodiment, an isolated immunogen includes a variant HBsAg in which the first transmembrane spanning domain of the HBsAg is replaced by a gp41 antigenic insert. For example, the gp41 antigenic insert replaces amino acid residues 1-35 of SEQ ID NO: 31. In another example, the gp41 antigenic insert replaces amino acid residues 1-32 of SEQ ID NO: 31. In yet another example, the gp41 antigenic insert replaces amino acid residues 1-29 of SEQ ID NO: 31. In a particular example, an isolated immunogen including a variant HBsAg in which the first transmembrane spanning domain of the HBsAg is replaced by a gp41 antigenic insert has the amino acid sequence set forth as SEQ ID NO: 29.

In another particular embodiment, an isolated immunogen includes a variant HBsAg in which the third transmembrane spanning domain of the HBsAg is replaced by a gp41 antigenic insert. For example, the gp41 antigenic insert replaces amino acid residues 150-190 of SEQ ID NO: 31. In another example, the gp41 antigenic insert replaces amino acid residues 153-187 of SEQ ID NO: 31. In yet another example, the gp41 antigenic insert replaces amino acid residues 156-185 of SEQ ID NO: 31. In a particular example, an isolated immunogen including a variant HBsAg in which the third transmembrane spanning domain of the HBsAg is replaced by a gp41 antigenic insert has the amino acid sequence set forth as SEQ ID NO: 57.

In an even more particular embodiment, an isolated immunogen includes a variant HBsAg in which the first and the third transmembrane spanning domains of the HBsAg are replaced by a gp41 antigenic insert. For example, the gp41 antigenic insert replaces amino acid residues 1-35 and 150-190 of SEQ ID NO: 31. In another example, the gp41 antigenic insert replaces amino acid residues 1-32 and 153-187 of SEQ ID NO: 31. In yet another example, the gp41 antigenic insert replaces amino acid residues 1-29 and 156-185 of SEQ ID NO: 31. In a particular example, an isolated immunogen includes a variant HBsAg in which the third transmembrane spanning domain of the HBsAg is replaced by a gp41 antigenic insert that has the amino acid sequence set forth as SEQ ID NO: 58.

Isolated nucleic acid molecules encoding the variant HBsAgs are also provided, as well as host cells transformed with the nucleic acid molecules and viral-like particles produced by the transformed host cells. The variant HBsAgs may further include elements, such as one or more HIV-specific T-helper cell epitopes. Viral-like particles including the variant HBsAgs are also provided herein. Compositions comprising the viral-like particles are also provided.

The disclosed isolated immunogen including a variant HBsAg can be used to induce an immune response, such as a protective immune response, when introduced into a subject. The isolated immunogen can also be used in assays to diagnose an HIV infection. Thus, methods are provided for inhibiting HIV infection in a subject, for inducing an immune response to HIV in a subject, for diagnosing HIV infection in a subject, and for identifying a B cell that produces antibodies that bind to gp41.

The foregoing and other features of the disclosure will become more apparent from the following detailed description, which proceeds with reference to the accompanying figures.

BRIEF DESCRIPTION OF SEQUENCES

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. All sequence database accession numbers referenced herein are understood to refer to the version of the sequence identified by that accession number as it was available on the designated date. In the accompanying sequence listing:

SEQ ID NO: 1 is a consensus amino acid sequence for the membrane proximal region (MPR) of gp41 of HIV-1. An X represents specific amino acids where alterations can be tolerated.

SEQ ID NO: 2 is a consensus amino acid sequence based on each clade consensus sequence of the MPR region from HIV-1.

SEQ ID NO: 3 is the ancestral amino acid sequence of the MPR region from HIV-1 clade M. This sequence is also the consensus amino acid sequence of the MPR region from HIV-1 clade AG.

SEQ ID NO: 4 is the consensus amino acid sequence of the MPR region from HIV-1 clade A1. This sequence is also the ancestral amino acid sequence of the MPR region from HIV-1 clade A1.

SEQ ID NO: 5 is the consensus amino acid sequence of the MPR region from HIV-1 clade A2.

SEQ ID NO: 6 is the consensus amino acid sequence of the MPR region from HIV-1 clade B. This sequence is also the ancestral amino acid sequence of the MPR region from HIV-1 clade B.

SEQ ID NO: 7 is the consensus amino acid sequence of the MPR region from HIV-1 clade C.

SEQ ID NO: 8 is the ancestral amino acid sequence of the MPR region from HIV-1 clade C.

SEQ ID NO: 9 is the consensus amino acid sequence of the MPR region from HIV-1 clade D.

SEQ ID NO: 10 is the consensus amino acid sequence of the MPR region from HIV-1 clade F1.

SEQ ID NO: 11 is the consensus amino acid sequence of the MPR region from HIV-1 clade F2.

SEQ ID NO: 12 is the consensus amino acid sequence of the MPR region from HIV-1 clade G.

SEQ ID NO: 13 is the consensus amino acid sequence of the MPR region from HIV-1 clade H.

SEQ ID NO: 14 is the consensus amino acid sequence of the MPR region from HIV-1 clade AE.

SEQ ID NO: 15 is the consensus amino acid sequence of the MPR region from HIV-1 clade AB.

SEQ ID NO: 16 is the consensus amino acid sequence of the MPR region from HIV-1 clade 04CPX.

SEQ ID NO: 17 is the consensus amino acid sequence of the MPR region from HIV-1 clade 06CPX.

SEQ ID NO: 18 is the consensus amino acid sequence of the MPR region from HIV-1 clade 08BC.

SEQ ID NO: 19 is the consensus amino acid sequence of the MPR region from HIV-1 clade 10CD.

SEQ ID NO: 20 is the consensus amino acid sequence of the MPR region from HIV-1 clade 11CPX.

SEQ ID NO: 21 is the consensus amino acid sequence of the MPR region from HIV-1 clade 12BF.

SEQ ID NO: 22 is the consensus amino acid sequence of the MPR region from HIV-1 clade 14BG.

SEQ ID NO: 23 is an exemplary amino acid sequence of an MPR region inserted into a disclosed HBsAg construct (TM12).

SEQ ID NO: 24 an exemplary amino acid sequence of an MPR region inserted into a disclosed HBsAg construct (TM14, TM16 or TM20)

SEQ ID NO: 25 is a consensus amino acid sequence for the transmembrane region of gp41. An X represents any hydrophobic amino acid.

SEQ ID NOs: 26-28 are amino acid sequences for a transmembrane domain of gp41.

SEQ ID NO: 29 is an amino acid sequence for a disclosed isolated immunogen in which the first transmembrane domain of hepatitis B surface antigen is replaced with the MPR and transmembrane domain of gp41.

SEQ ID NO: 30 is a leader sequence from influenza hemagglutinin MKTIIALSYIFCLVFAQDLPGNDNNS.

SEQ ID NO: 31 is an amino acid sequence of an exemplary wildtype HBsAg.

SEQ ID NO: 32 is an example of a nucleotide sequence for a T helper cell epitope.

SEQ ID NO: 33 is an example of an amino acid sequence for a T helper cell epitope.

SEQ ID NO: 34 is the CAAX amino acid sequence, where C is cystein, A is an aliphatic amino acid and X is any amino acid.

SEQ ID NO: 35 is the core amino acid sequence of the 2F5 epitope.

SEQ ID NO: 36 is the core amino acid sequence of the 4E10 epitope.

SEQ ID NO: 37 is the linker sequence GPGP.

SEQ ID NO: 38 is a forward primer for amplification of the HBsAg.

SEQ ID NO: 39 is a reverse primer for amplification of the HBsAg.

SEQ ID NO: 40 is a forward primer for amplification of MPR.

SEQ ID NO: 41 is a reverse primer for amplification of MPR.

SEQ ID NO: 42 is a reverse primer for amplification of MPR-Foldon.

SEQ ID NO: 43 is a forward primer for amplification of C-heptad.

SEQ ID NO: 44 is a reverse primer for amplification of MPR-Tm5.

SEQ ID NO: 45 is a reverse primer for amplification of MPR-Tm10.

SEQ ID NO: 46 is a reverse primer for amplification of MPR-Tm15.

SEQ ID NO: 47 is a reverse primer for amplification of MPR-Tm23.

SEQ ID NO: 48 is a forward primer for amplification of the MPR region with AgeI.

SEQ ID NO: 49 is a reverse primer for amplification of the MPR region with AgeI.

SEQ ID NO: 50 is a forward primer for amplification of the MPR region with AgeI.

SEQ ID NO: 51 is a reverse primer for amplification of the MPR region with AgeI.

SEQ ID NO: 52 is a forward primer for amplification of the MPR region with HBsAg (MPRSAG or MPR-N-term).

SEQ ID NO: 53 is a reverse primer for amplification of the MPR region with HBsAg (MPRSAG or MPR-N-term).

SEQ ID NO: 54 is a forward primer for amplification of SAGMPR-R1 (HBsAg at the N-terminus of MPR).

SEQ ID NO: 55 is a reverse primer for amplification of SAGMPR-R1 (HBsAg at the N-terminus of MPR).

SEQ ID NO: 56 is an amino acid sequence of a disclosed variant HbsAg construct (34) in which an MPR is inserted between a second and third domain in the variant HBsAg.

SEQ ID NO: 57 is an amino acid sequence for a disclosed isolated immunogen in which the third transmembrane domain of hepatitis B surface antigen is replaced with the MPR and transmembrane domain of gp41.

SEQ ID NO: 58 is an amino acid sequence for a disclosed isolated immunogen in which the first and third transmembrane domains of hepatitis B surface antigen are each replaced with the MPR and transmembrane domain of gp41.

SEQ ID NO: 59 is a nucleic acid sequence for a disclosed isolated immunogen in which the third transmembrane domain of HBsAg is replaced with the MPR and transmembrane domain of gp41.

SEQ ID NO: 60 is an amino acid sequence of the MPR region in the TM32 or TM32F constructs.

SEQ ID NO: 61 is an amino acid sequence of the MPR region in the TM34 construct.

SEQ ID NO: 62 is an amino acid sequence of a disclosed variant HbsAg construct (TM16+34) in which the first domain is replaced with a MPR and transmembrane domain of gp41 and an additional MPR is inserted between a second and third domain in the variant HBsAg.

SEQ ID NO: 63 is an amino acid sequence of a disclosed variant HbsAg construct (32F) in which four MPRs are inserted between a second and third domain in the variant HBsAg.

SEQ ID NO: 64 is an amino acid sequence of a disclosed variant HbsAg construct (TM16+32F) in which the first domain is replaced with a MPR and transmembrane domain of gp41 and four additional MPRs are inserted between a second and third domain in the variant HBsAg.

BRIEF DESCRIPTION OF THE DRAWINGS

FIG. 1 is a schematic representation of virus-like particles expressing the MPR of gp41 demonstrating the MPR anchored to a lipid membrane.

FIG. 6 is a pair of digital images of particles detected by electron microscopy illustrating the size of variant HBsAgs in which the first transmembrane domain is substituted with a gp41 membrane spanning domain and that such variants are capable of particle formation.

FIG. 7 is a pair of graphs illustrating successful HBsAg particle assembly for variant HBsAgs in which the third transmembrane domain is substituted with a gp41 membrane spanning domain as demonstrated by size exclusion chromatography and cesium chloride gradient.

FIG. 8 is digital image of gel illustrating purification of a variant HBsAg (MPRS) by a methyl HIC column in which the variant HBsAg includes a gp41 insert following the fourth domain of the HBsAg (MPRS).

FIG. 14 is a pair of bar graphs illustrating the immunogenicity of the disclosed multivalent MPR particles.

DETAILED DESCRIPTION

Figure 2A:
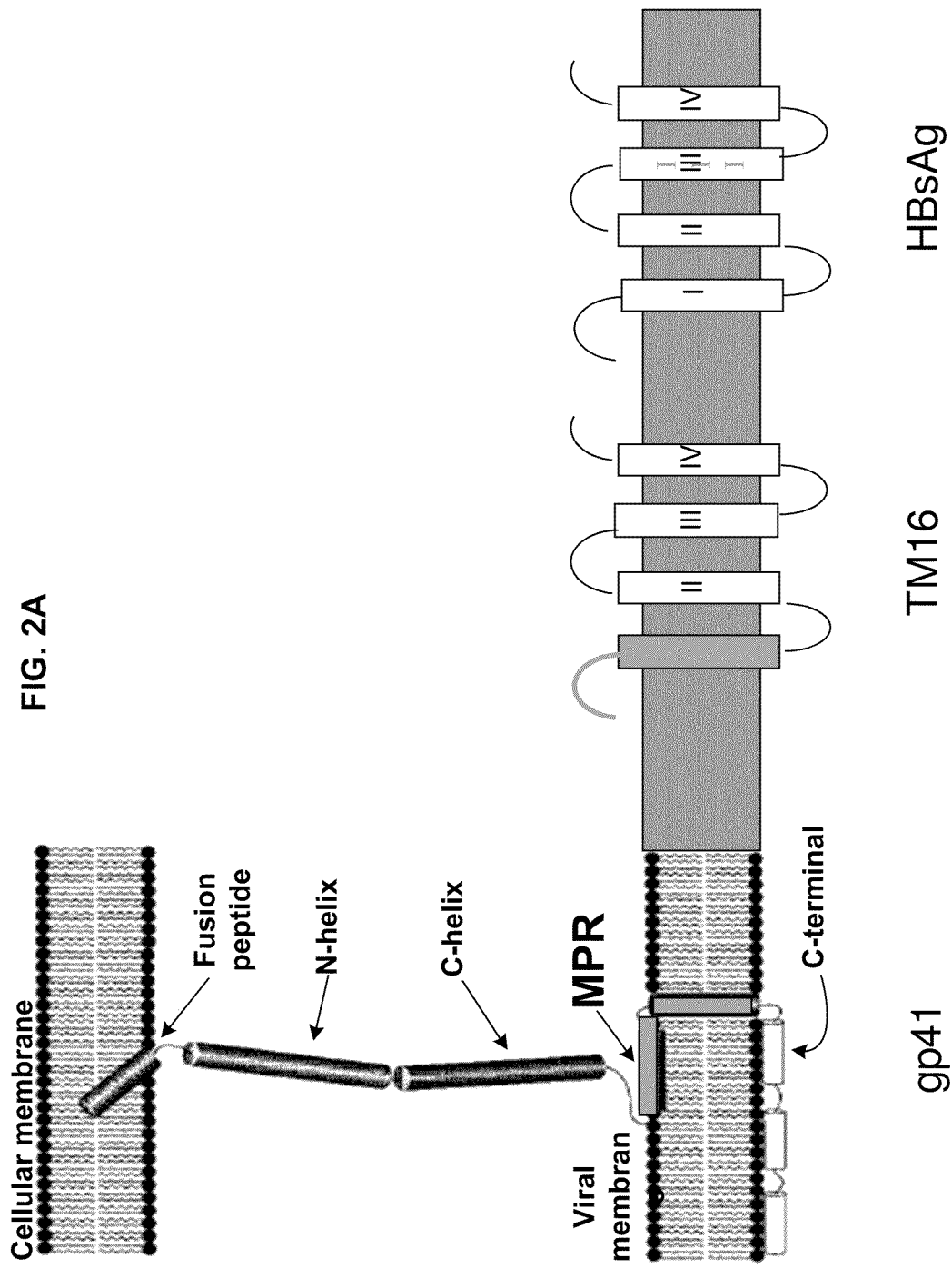
FIG. 2A is a schematic illustrating the location of MPR in gp41 and a variant HBsAg in which the first domain of HBsAg was replaced with the membrane spanning domain of gp41 that allows the MPR to be correctly oriented in relation to the lipid and anchors the MPR from gp41 within HBsAg.

I. Abbreviations and Terms
AIDS: acquired immune deficiency syndrome
Gp41: glycoprotein 41
HBsAg: hepatitis B surface antigen
HIV: human immunodeficiency virus
MPR: membrane proximal region Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting To facilitate review of the various embodiments of this disclosure, the following explanations of specific terms are provided:

Adjuvant: A vehicle used to enhance antigenicity; such as a suspension of minerals (alum, aluminum hydroxide, or phosphate) on which antigen is adsorbed; or water-in-oil emulsion in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages) Immunstimulatory oligonucleotides (such as those including a CpG motif) can also be used as adjuvants (for example see U.S. Pat. No. 6,194,388; U.S. Pat. No. 6,207,646; U.S. Pat. No. 6,214,806; U.S. Pat. No. 6,218,371; U.S. Pat. No. 6,239,116; U.S. Pat. No. 6,339,068; U.S. Pat. No. 6,406,705; and U.S. Pat. No. 6,429,199).

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term is used interchangeably with the term "immunogen." The term "antigen" includes all related antigenic epitopes. An "antigenic polypeptide" is a polypeptide to which an immune response, such as a T cell response or an antibody response, can be stimulated. "Epitope" or "antigenic determinant" refers to a site on an antigen to which B and/or T cells respond. In one embodiment, T cells respond to the epitope when the epitope is presented in conjunction with an MHC molecule. Epitopes can be formed both from contiguous amino acids (linear) or noncontiguous amino acids juxtaposed by tertiary folding of an antigenic polypeptide (conformational). Epitopes formed from contiguous amino acids are typically retained on exposure to denaturing solvents whereas epitopes formed by tertiary folding are typically lost on treatment with denaturing solvents. Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 5 and 15 amino acids, such as, 9, 10, 12 or 15 amino acids. The amino acids are in a unique spatial conformation. Methods of determining spatial conformation of epitopes include, for example, x-ray crystallography and multi-dimensional nuclear magnetic resonance spectroscopy. The term "antigen" denotes both subunit antigens, (for example, antigens which are separate and discrete from a whole organism with which the antigen is associated in nature), as well as killed, attenuated or inactivated bacteria, viruses, fungi, parasites or other microbes. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses an antigen or antigenic determinant in vivo, such as in gene therapy and DNA immunization applications, is also included in the definition of antigen herein.

An "antigen," when referring to a protein, includes a protein with modifications, such as deletions, additions and substitutions (generally conservative in nature) to the native sequence, so long as the protein maintains the ability to elicit an immunological response, as defined herein. These modifications may be deliberate, as through site-directed mutagenesis, or may be accidental, such as through mutations of hosts which produce the antigens.

Antigen Delivery Platform or Epitope Mounting Platform: In the context of the present disclosure, the terms "antigen delivery platform" and "epitope mounting platform" refer to a macromolecular complex including one or more antigenic epitopes. Delivery of an antigen (including one or more epitopes) in the context of an epitope mounting platform enhances, increases, ameliorates or otherwise improves a desired antigen-specific immune response to the antigenic epitope(s). The molecular constituents of the antigen delivery platform may be antigenically neutral or may be immunologically active, that is, capable of generating a specific immune response. Nonetheless, the term antigen delivery platform is utilized to indicate that a desired immune response is generated against a selected antigen that is a component of the macromolecular complex other than the platform polypeptide to which the antigen is attached. Accordingly, the epitope mounting platform is useful for delivering a wide variety of antigenic epitopes, including antigenic epitopes of pathogenic organisms such as bacteria and viruses. The antigen delivery platform of the present disclosure is particularly useful for the delivery of complex peptide or polypeptide antigens, which may include one or many distinct epitopes.

Amplification: A technique that increase the number of molecules in a specimen. Amplification of a nucleic acid molecule (e.g., a DNA or RNA molecule) refers to use of a technique that increases the number of copies of a nucleic acid molecule in a specimen. An example of amplification is the polymerase chain reaction (PCR), in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification may be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Antibody: Immunoglobulin molecules and immunologically active portions of immunoglobulin molecules, that is, molecules that contain an antigen binding site that specifically binds (immunoreacts with) an antigen.

A naturally occurring antibody (e.g., IgG, IgM, IgD) includes four polypeptide chains, two heavy (H) chains and two light (L) chains interconnected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) a Fab fragment consisting of the $V_L$, $V_H$, $C_L$ and $C_{H1}$ domains; (ii) an $F_d$ fragment consisting of the $V_H$ and $C_{H1}$ domains; (iii) an Fv fragment consisting of the $V_L$ and $V_H$ domains of a single arm of an antibody, (iv) a dAb fragment (Ward et al., Nature 341:544-546, 1989) which consists of a $V_H$ domain; (v) an isolated complimentarity determining region (CDR); and (vi) a F(ab')$_2$ fragment, a bivalent fragment comprising two Fab fragments linked by a disulfide bridge at the hinge region.

Methods of producing polyclonal and monoclonal antibodies are known to those of ordinary skill in the art, and many antibodies are available. See, e.g., Coligan, *Current Protocols in Immunology* Wiley/Greene, NY, 1991; and Harlow and Lane, *Antibodies: A Laboratory Manual* Cold Spring Harbor Press, NY, 1989; Stites et al., (eds.) *Basic and Clinical Immunology* (4th ed.) Lange Medical Publications, Los Altos, Calif., and references cited therein; Goding, *Monoclonal Antibodies: Principles and Practice* (2d ed.) Academic Press, New York, N.Y. 1986; and Kohler and Milstein, *Nature* 256: 495-497, 1975. Other suitable techniques for antibody preparation include selection of libraries of recombinant antibodies in phage or similar vectors. See, Huse et al., *Science* 246: 1275-1281, 1989; and Ward et al., *Nature* 341: 544-546, 1989. "Specific" monoclonal and polyclonal antibodies and antisera (or antiserum) will usually bind with a $K_D$ of at least about 0.1 µM, preferably at least about 0.01 µM or better, and most typically and preferably, 0.001 µM or better.

Immunoglobulins and certain variants thereof are known and many have been prepared in recombinant cell culture (e.g., see U.S. Pat. No. 4,745,055; U.S. Pat. No. 4,444,487; WO 88/03565; EP 256,654; EP 120,694; EP 125,023; Faoulkner et al., *Nature* 298:286, 1982; Morrison, *J. Immunol.* 123:793, 1979; Morrison et al., *Ann Rev. Immunol* 2:239, 1984). Detailed methods for preparation of chimeric (humanized) antibodies can be found in U.S. Pat. No. 5,482,856. Additional details on humanization and other antibody production and engineering techniques can be found in Borrebaeck (ed), *Antibody Engineering*, 2$^{nd}$ *Edition* Freeman and Company, NY, 1995; McCafferty et al., *Antibody Engineering, A Practical Approach*, IRL at Oxford Press, Oxford, England, 1996, and Paul *Antibody Engineering Protocols* Humana Press, Towata, N.J., 1995.

Animal: Living multi-cellular vertebrate organisms, a category that includes, for example, mammals and birds. The term mammal includes both human and non-human mammals. Similarly, the term "subject" includes both human and veterinary subjects.

Antigenic polypeptide fragment: A polypeptide that is antigenic. In an example, an antigenic polypeptide fragment includes a MPR of gp41, such as a MPR with an amino acid sequence set forth in SEQ ID NO: 1.

Conservative variants: "Conservative" amino acid substitutions are those substitutions that do not substantially affect or decrease a desired activity of a protein or polypeptide. For example, in the context of the present disclosure, a conservative amino acid substitution does not substantially alter or decrease the immunogenicity of an antigenic epitope. Similarly, a conservative amino acid substitution does not substantially affect the structure or, for example, the stability of a protein or polypeptide. Specific, non-limiting examples of a conservative substitution include the following examples:

| Original Residue Substitutions | Conservative |
| --- | --- |
| Ala | Ser |
| Arg | Lys |
| Asn | Gln; His |
| Asp | Glu |
| Cys | Ser |
| Gln | Asn |
| Glu | Asp |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variation also includes the use of a substituted amino acid in place of an unsubstituted parent amino acid, provided that antibodies raised to the substituted polypeptide also immunoreact with the unsubstituted polypeptide. Non-conservative substitutions are those that reduce an activity or antigenicity or substantially alter a structure, such as a secondary or tertiary structure, of a protein or polypeptide.

cDNA (complementary DNA): A piece of DNA lacking internal, non-coding segments (introns) and regulatory sequences that determine transcription. cDNA is typically synthesized in the laboratory by reverse transcription from messenger RNA extracted from cells.

Diagnostic: Identifying the presence or nature of a pathologic condition, such as, but not limited to a condition induced by a viral or other pathogen. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (or for example, the probability of severity) of a pathologic condition, such as a symptom induced by a viral infection or other pathogenic organism, or resulting indirectly from such an infection.

Epitope: An antigenic determinant. These are particular chemical groups or peptide sequences on a molecule that are antigenic, that is, that elicit a specific immune response. An antibody specifically binds a particular antigenic epitope on a polypeptide. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or 8-10 amino acids in a unique spatial conformation. Methods of determining spatial conformation of epitopes include, for example, x-ray crystallography and multi-dimensional nuclear magnetic resonance spectroscopy. See, e.g., "Epitope Mapping Protocols" in *Methods in Molecular Biology*, Vol. 66, Glenn E. Morris, Ed (1996). In one embodiment, an epitope binds an MHC molecule, e.g., an HLA molecule or a DR molecule. These molecules bind polypeptides having the correct anchor amino acids separated by about eight or nine amino acids Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (typically, ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences.

Glycoprotein 41 (gp41): An HIV-1 envelope glycoprotein that mediates receptor binding and HIV entry into a cell. Gp41 includes a MPR and a transmembrane spanning domain. Gp41 is immunogenic and induces a variety of neutralizing antibodies, such as neutralizing antibodies directed to 2F5, 4E10 and Z13. These three gp41 neutralizing antibodies recognize the MPR of the HIV-1 gp41 glycoprotein.

Gp41 antigenic insert: A peptide fragment that includes a membrane proximal region of gp41 and a transmembrane domain of gp41. In an example, the membrane proximal region (also referred to as the antigenic polypeptide fragment) of gp41 includes the amino acid sequence of SEQ ID NO: 1 and a transmembrane domain of gp41 including the amino acid sequence set forth as SEQ ID NO: 25. For example, the antigenic polypeptide fragment of gp41 is between 28 and 150 amino acids in length and the transmembrane domain of gp41 is between 22 and 40 amino acids in length and wherein the transmembrane domain of gp41 is C-terminal to the antigenic polypeptide fragment of gp41.

Hepatitis B Surface Antigen (HBsAg): HBsAg is composed of 3 polypeptides, preS1, preS2 and S that are produced from alternative translation start sites. The surface proteins have many functions, including attachment and penetration of the virus into hepatocytes at the beginning of the infection process. The surface antigen is a principal component of the hepatitis B envelope. HBsAg has four membrane spanning domains. As used herein, a variant HBsAg is a HBsAg that includes a MPR from gp41. In a particular example, a variant HBsAg includes a MPR and a membrane spanning domain from gp41. In certain examples, a variant HBsAg has an amino acid sequence set forth by SEQ ID NOs: 29, 56-58, 62-64 or an amino acid sequence that is at least 80%, at least 85%, at least 90%, at least 95%, or at least 98% sequence similarity, such as 80%, 82%, 85%, 87%, 90%, 93%, 95% or 98% sequence similarity with such sequences.

Host cells: Cells in which a polynucleotide, for example, a polynucleotide vector or a viral vector, can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Human Immunodeficiency Virus (HIV): A virus, known to cause AIDS, that includes HIV-1 and HIV-2. HIV-1 is composed of two copies of single-stranded RNA enclosed by a conical capsid including the viral protein p24, typical of lentiviruses. The capsid is surrounded by a plasma membrane of host-cell origin.

The envelope protein of HIV-1 is made up of a glycoprotein called gp160. The mature, virion associated envelope protein is a trimeric molecule composed of three gp120 and three gp41 subunits held together by weak noncovalent interactions. This structure is highly flexible and undergoes substantial conformational changes upon gp120 binding with CD4 and chemokine coreceptors, which leads to exposure of the fusion peptides of gp41 that insert into the target cell membrane and mediate viral entry. Following oligomerization in the endoplasmic reticulum, the gp160 precursor protein is cleaved by cellular proteases and is transported to the cell surface. During the course of HIV-1 infection, the gp120 and gp41 subunits are shed from virions and virus-infected cells due to the noncovalent interactions between gp 120 and gp41 and between gp41 subunits.

Immune response: A response of a cell of the immune system, such as a B cell, T cell, or monocyte, to a stimulus. In some cases, the response is specific for a particular antigen (that is, an "antigen-specific response"). In some cases, an immune response is a T cell response, such as a CD4+ response or a CD8+ response. Alternatively, the response is a B cell response, and results in the production of specific antibodies. For purposes of the present invention, a "humoral immune response" refers to an immune response mediated by antibody molecules, while a "cellular immune response" is one mediated by T-lymphocytes and/or other white blood cells. A "protective immune response" is an immune response that inhibits a detrimental function or activity (such as a detrimental effect of a pathogenic organism such as a virus), reduces infection by a pathogenic organism (such as, a virus), or decreases symptoms that result from infection by the pathogenic organism. A protective immune response can be measured, for example, by the inhibition of viral replication or plaque formation in a plaque reduction assay or ELISA-neutralization assay (NELISA), or by measuring resistance to viral challenge in vivo.

An immunogenic composition can induce a B cell response. The ability of a particular antigen to stimulate a B cell response can be measured by determining if antibodies are present that bind the antigen. In one example, neurtralizing antibodies are produced.

One aspect of cellular immunity involves an antigen-specific response by cytolytic T-cells ("CTL"s). CTLs have specificity for peptide antigens that are presented in association with proteins encoded by the major histocompatibility complex (MHC) and expressed on the surface of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, for example, Erickson et al. (1993) *J. Immunol.* 151:4189-4199; Doe et al. (1994) *Eur. J. Immunol.* 24:2369-2376. Recent methods of measuring cell-mediated immune response include measurement of intracellular cytokines or cytokine secretion by T-cell populations, or by measurement of epitope specific T-cells (for example, by the tetramer technique) (reviewed by McMichael and O'Callaghan (1998) *J. Exp. Med.* 187(9)1367-1371; Mcheyzer-Williams et al. (1996) *Immunol. Rev.* 150:5-21; Lalvani et al. (1997) *J. Exp. Med.* 186: 859-865).

Thus, an immunological response as used herein may be one which stimulates the production of CTLs, and/or the production or activation of helper T-cells. The antigen of interest may also elicit an antibody-mediated immune response. Hence, an immunological response may include one or more of the following effects: the production of antibodies by B-cells; and/or the activation of suppressor T-cells and/or gamma-delta T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

Immunogenic peptide: A peptide which comprises an allele-specific motif or other sequence such that the peptide will bind an MHC molecule and induce a cytotoxic T lymphocyte ("CTL") response, or a B cell response (e.g. antibody production) against the antigen from which the immunogenic peptide is derived.

Immunogenic composition: A composition comprising at least one epitope of a virus, or other pathogenic organism, that induces a measurable CTL response, or induces a measurable B cell response (for example, production of antibodies that specifically bind the epitope). It further refers to isolated nucleic acids encoding an immunogenic epitope of virus or other pathogen that can be used to express the epitope (and thus be used to elicit an immune response against this polypeptide or a related polypeptide expressed by the pathogen). For in vitro use, the immunogenic composition may consist of the isolated nucleic acid, protein or peptide. For in vivo use, the immunogenic composition will typically include the nucleic acid, protein or peptide in pharmaceutically acceptable carriers or excipients, and/or other agents, for example, adjuvants. An immunogenic polypeptide (such as an antigenic polyeptide), or nucleic acid encoding the polypeptide, can be readily tested for its ability to induce a CTL or antibody response by art-recognized assays.

Isolated: An "isolated" biological component (such as a nucleic acid or protein or organelle) has been substantially separated or purified away from other biological components in the cell of the organism in which the component naturally occurs, for example, other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule to facilitate detection of that molecule. Specific, non-limiting examples of labels include fluorescent tags, affinity tags, enzymatic linkages, and radioactive isotopes. An affinity tag is a peptide or polypeptide sequence capable of specifically binding to a specified substrate, for example, an organic, non-organic or enzymatic substrate or cofactor. A polypeptide including a peptide or polypeptide affinity tag can typically be recovered, for example, purified or isolated, by means of the specific interaction between the affinity tag and its substrate. An exemplary affinity tag is a poly-histidine (e.g., six-histidine) affinity tag which can specifically bind to non-organic metals such as nickel and/or cobalt. Additional affinity tags are well known in the art.

Linking peptide: A linking peptide (or linker sequence) is an amino acid sequence that covalently links two polypeptide domains. Linking peptides can be included between the rotavirus NSP2 polypeptide and an antigenic epitope to provide rotational freedom to the linked polypeptide domains and thereby to promote proper domain folding. Linking peptides, which are generally between 2 and 25 amino acids in length, are well known in the art and include, but are not limited to the amino acid sequences glycine-proline-glycine-proline (GPGP)(SEQ ID NO: 37) and glycine-glycine-serine (GGS), as well as the glycine(4)-serine spacer described by Chaudhary et al., *Nature* 339:394-397, 1989. In some cases multiple repeats of a linking peptide are present.

Lymphocytes: A type of white blood cell that is involved in the immune defenses of the body. There are two main types of lymphocytes: B cells and T cells. "T lymphocytes" or "T cells" are non-antibody producing lymphocytes that constitute a part of the cell-mediated arm of the immune system. T cells arise from immature lymphocytes that migrate from the bone marrow to the thymus, where they undergo a maturation process under the direction of thymic hormones. Here, the mature lymphocytes rapidly divide increasing to very large numbers. The maturing T cells become immunocompetent based on their ability to recognize and bind a specific antigen. Activation of immunocompetent T cells is triggered when an antigen binds to the lymphocyte's surface receptors. T cells include, but are not limited to, $CD4^+$ T cells and $CD8^+$ T cells. A $CD4^+$ T lymphocyte is an immune cell that carries a marker on its surface known as "cluster of differentiation 4" (CD4).

These cells, also known as helper T cells, help orchestrate the immune response, including antibody responses as well as killer T cell responses. CD8+ T cells carry the "cluster of differentiation 8" (CD8) marker. In one embodiment, a CD8 T cell is a cytotoxic T lymphocyte. In another embodiment, a CD8 cell is a suppressor T cell.

Mammal: This term includes both human and non-human mammals unless otherwise specified. Similarly, the term "subject" includes both human and veterinary subjects.

Membrane proximal region (MPR) or membrane proximal external region (MPER) of gp41: A region that is immediately N-terminal of the transmembrane region of gp41. The MPR is highly hydrophobic (50% of residues are hydrophobic) and is highly conserved across many HIV clades (Zwick, M. B., et al., *J Virol*, 75 (22): p. 10892-905, 2001). The conserved MPR of HIV-1 gp41 is a target of two broadly neutralizing human monoclonal antibodies, 2F5 and 4E10. The core of the 2F5 epitope has been shown to be ELDKWAS (SEQ ID NO: 35). With this epitope, the residues D, K, and W were found to be most critical for recognition by 2F5. The core of the 4E10 epitope, NWFDIT (SEQ ID NO: 36), maps just C-terminal to the 2F5 epitope on the gp41 ectodomain.

Oligonucleotide: A linear polynucleotide sequence of up to about 100 nucleotide bases in length.

Open reading frame ("ORF"): A series of nucleotide triplets (codons) coding for amino acids without any internal termination codons. These sequences are usually translatable into a polypeptide (peptide or protein).

Operatively linked: A first nucleic acid sequence is operatively linked with a second nucleic acid sequence when the first nucleic acid sequence is placed in a functional relationship with the second nucleic acid sequence. For instance, a promoter is operatively linked to a coding sequence if the promoter affects the transcription or expression of the coding sequence. Generally, operatively linked DNA sequences are contiguous and, where necessary to join two protein-coding regions, in the same reading frame, for example, two polypeptide domains or components of a fusion protein.

Pharmaceutically acceptable carriers and/or pharmaceutically acceptable excipients: The pharmaceutically acceptable carriers or excipients of use are conventional. *Remington's Pharmaceutical Sciences*, by E. W. Martin, Mack Publishing Co., Easton, Pa., 15th Edition (1975), describes compositions and formulations suitable for pharmaceutical delivery of the polypeptides and polynucleotides disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

A "therapeutically effective amount" is a quantity of a composition used to achieve a desired effect in a subject. For instance, this can be the amount of the composition necessary to inhibit viral (or other pathogen) replication or to prevent or measurably alter outward symptoms of viral (or other pathogenic) infection. When administered to a subject, a dosage will generally be used that will achieve target tissue concentrations (for example, in lymphocytes) that has been shown to achieve an in vitro effect.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Polypeptide: Any chain of amino acids, regardless of length or post-translational modification (for example, glycosylation or phosphorylation), such as a protein or a fragment or subsequence of a protein. The term "peptide" is typically used to refer to a chain of amino acids of between 3 and 30 amino acids in length. For example an immunologically relevant peptide may be between about 7 and about 25 amino acids in length, e.g., between about 8 and about 10 amino acids.

In the context of the present disclosure, a polypeptide can be a fusion protein comprising a plurality of constituent polypeptide (or peptide) elements. Typically, the constituents of the fusion protein are genetically distinct, that is, they originate from distinct genetic elements, such as genetic elements of different organisms or from different genetic elements (genomic components) or from different locations on a single genetic element, or in a different relationship than found in their natural environment. Nonetheless, in the context of a fusion protein the distinct elements are translated as a single polypeptide. The term monomeric fusion protein (or monomeric fusion protein subunit) is used synonymously with such a single fusion protein polypeptide to clarify reference to a single constituent subunit where the translated fusion proteins assume a multimeric tertiary structure.

Specifically, in an embodiment, a monomeric fusion protein subunit includes in an N-terminal to C-terminal direction: a viral NSP2 polypeptide; a linear linking peptide; and an antigenic polypeptide or epitope translated into a single polypeptide monomer. A plurality (for example, 4, 8, 12 or 16) of monomeric fusion protein subunits self-assembles into a multimeric ring structure.

Preventing or treating an infection: Inhibiting infection by a pathogen such as a virus, such as a lentivirus, or other virus, refers to inhibiting the full development of a disease either by avoiding initial infection or inhibiting development of the disease process once it is initiated. For example, inhibiting a viral infection refers to lessening symptoms resulting from infection by the virus, such as preventing the development of symptoms in a person who is known to have been exposed to the virus, or to lessening virus number or infectivity of a virus in a subject exposed to the virus. "Treatment" refers to a therapeutic or prophylactic intervention that ameliorates or prevents a sign or symptom of a disease or pathological condition related to infection of a subject with a virus or other pathogen.

Probes and primers: A probe comprises an isolated nucleic acid attached to a detectable label or reporter molecule. Primers are short nucleic acids, preferably DNA oligonucleotides, for example, a nucleotide sequence of about 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, for example, by the polymerase chain reaction (PCR) or other nucleic-acid amplification methods known in the art. One of skill in the art will appreciate that the specificity of a particular probe or primer increases with its length. Thus, for example, a primer comprising 20 consecutive nucleotides will anneal to a target with a higher specificity than a corresponding primer of only about 15 nucleotides. Thus, in order to obtain greater specificity, probes and primers may be selected that comprise 20, 25, 30, 35, 40, 50 or more consecutive nucleotides.

Promoter: A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see e.g., Bitter et al., *Methods in Enzymology* 153:516-544, 1987). For example, when cloning in bacterial systems, inducible promoters such as pL of bacteriophage lambda, plac, pap, ptac (ptrp-lac hybrid promoter) and the like may be used. In one embodiment, when cloning in mammalian cell systems, promoters derived from the genome of mammalian cells (for example, metallothionein promoter) or from mammalian viruses (for example, the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

Protein purification: the fusion polypeptides disclosed herein can be purified (and/or synthesized) by any of the means known in the art (see, e.g., *Guide to Protein Purification*, ed. Deutscher, *Meth. Enzymol.* 185, Academic Press, San Diego (1990); and Scopes, *Protein Purification: Principles and Practice*, Springer Verlag, New York (1982). Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Purified: The term "purified" does not require absolute purity; rather, it is intended as a relative term. Thus, for example, a purified nucleic acid is one in which the nucleic acid is more enriched than the nucleic acid in its natural environment within a cell. Similarly, a purified peptide preparation is one in which the peptide or protein is more enriched than the peptide or protein is in its natural environment within a cell. In one embodiment, a preparation is purified such that the protein or peptide represents at least 50% (such as, but not limited to, 70%, 80%, 90%, 95%, 98% or 99%) of the total peptide or protein content of the preparation.

Recombinant: A recombinant nucleic acid is one that has a sequence that is not naturally occurring or has a sequence that is made by an artificial combination of two otherwise separated segments of sequence, for example, a polynucleotide encoding a fusion protein. This artificial combination is often accomplished by chemical synthesis or, more commonly, by the artificial manipulation of isolated segments of nucleic acids, e.g., by genetic engineering techniques.

Sequence identity: The similarity between amino acid (and polynucleotide) sequences is expressed in terms of the similarity between the sequences, otherwise referred to as sequence identity. Sequence identity is frequently measured in terms of percentage identity (or similarity); the higher the percentage, the more similar are the primary structures of the two sequences. In general, the more similar the primary structures of two amino acid sequences, the more similar are the higher order structures resulting from folding and assembly. However, the converse is not necessarily true, and polypeptides with low sequence identity at the amino acid level can nonetheless have highly similar tertiary and quaternary structures. For example, NSP2 homologs with little sequence identity (for example, less than 50% sequence identity, or even less than 30%, or less than 20% sequence identity) share similar higher order structure and assembly properties, such that even distantly related NSP2 proteins assemble into multimeric ring structures as described herein.

Methods of determining sequence identity are well known in the art. Various programs and alignment algorithms are described in: Smith and Waterman, *Adv. Appl. Math.* 2:482, 1981; Needleman and Wunsch, *J. Mol. Biol.* 48:443, 1970; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. USA* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Another indicia of sequence similarity between two nucleic acids is the ability to hybridize. The more similar are the sequences of the two nucleic acids, the more stringent the conditions at which they will hybridize. The stringency of hybridization conditions are sequence-dependent and are different under different environmental parameters. Thus, hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found, for example, in Sambrook et al., *Molecular Cloning: A Laboratory Manual*, Cold Spring Harbor Laboratory Press, Cold Spring Harbor, N.Y., 2001; Tijssen, *Hybridization With Nucleic Acid Probes, Part I: Theory and Nucleic Acid Preparation*, Laboratory Techniques in Biochemistry and Molecular Biology, Elsevier Science Ltd., NY, N.Y., 1993. and Ausubel et al. *Short Protocols in Molecular Biology*, 4th ed., John Wiley & Sons, Inc., 1999.

For purposes of the present disclosure, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize. In contrast nucleic acids that hybridize under "low stringency conditions include those with much less sequence identity, or with sequence identity over only short subsequences of the nucleic acid.

For example, a specific example of progressively higher stringency conditions is as follows: 2×SSC/0.1% SDS at about room temperature (hybridization conditions); 0.2× SSC/0.1% SDS at about room temperature (low stringency conditions); 0.2×SSC/0.1% SDS at about 42° C. (moderate stringency conditions); and 0.1×SSC at about 68° C. (high stringency conditions). One of skill in the art can readily determine variations on these conditions (e.g., *Molecular Cloning: A Laboratory Manual,* 2nd ed., vol. 1-3, ed. Sambrook et al., Cold Spring Harbor Laboratory Press, Cold Spring Harbor, N.Y., 1989). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Subject: Living multi-cellular vertebrate organisms, a category that includes both human and veterinary subjects, including human and non-human mammals.

Therapeutically active polypeptide: An agent, such as an epitope of a virus or other pathogen that causes induction of an immune response, as measured by clinical response (for example increase in a population of immune cells, increased cytolytic activity against the epitope). Therapeutically active molecules can also be made from nucleic acids. Examples of a nucleic acid based therapeutically active molecule is a nucleic acid sequence that encodes an epitope of a protein of a virus or other pathogen, wherein the nucleic acid sequence is operatively linked to a control element such as a promoter.

Therapeutically Effective Amount: An amount of a composition that alone, or together with an additional therapeutic agent(s) (for example nucleoside/nucleotide reverse transcriptase inhibitors, a non-nucleoside reverse transcriptase inhibitors, protease inhibitors, fusion/entry inhibitors or integrase inhibitors) induces the desired response (e.g., inhibition of HIV infection or replication). In one example, a desired response is to inhibit HIV replication in a cell to which the therapy is administered. HIV replication does not need to be completely eliminated for the composition to be effective. For example, a composition can decrease HIV replication by a desired amount, for example by at least 10%, at least 20%, at least 50%, at least 60%, at least 70%, at least 80%, at least 90%, at least 95%, at least 98%, or even at least 100% (elimination of HIV), as compared to HIV replication in the absence of the composition.

In another example, a desired response is to inhibit HIV infection. The HIV infected cells do not need to be completely eliminated for the composition to be effective. For example, a composition can decrease the number of HIV infected cells by a desired amount, for example by at least 10%, at least 20%, at least 50%, at least 60%, at least 70%, at least 80%, at least 90%, at least 95%, at least 98%, or even at least 100% (elimination of detectable HIV infected cells), as compared to the number of HIV infected cells in the absence of the composition.

A therapeutically effective amount of a composition including variant HBsAgs, can be administered in a single dose, or in several doses, for example daily, during a course of treatment. However, the therapeutically effective amount can depend on the subject being treated, the severity and type of the condition being treated, and the manner of administration. For example, a therapeutically effective amount of such agent can vary from about 1 μg-10 mg per 70 kg body weight if administered intravenously.

Tissue: A plurality of functionally related cells. A tissue can be a suspension, a semi-solid, or solid. Tissue includes cells collected from a subject.

Transformed or Transfected: A transformed cell is a cell into which a nucleic acid molecule has been introduced by molecular biology techniques. As used herein, the term introduction or transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Transmembrane domain or region of gp41: A region or domain of gp41 that is immediately C-terminal to the membrane proximal region of gp41. An example of a transmembrane domain is provided in SEQ ID NO: 25.

Treating a disease: "Treatment" refers to a therapeutic intervention that ameliorates a sign or symptom of a disease or pathological condition, such as a sign or symptom of HIV. Treatment can also induce remission or cure of a condition, such as elimination of detectable HIV infected cells. In particular examples, treatment includes preventing a disease, for example by inhibiting the full development of a disease, such as HIV, by inhibiting HIV replication or infection or the development of AIDS. Prevention of a disease does not require a total absence of disease. For example, a decrease of at least 50% can be sufficient.

Vaccine: A vaccine is a pharmaceutical composition that elicits a prophylactic or therapeutic immune response in a subject. In some cases, the immune response is a protective immune response. Typically, a vaccine elicits an antigen-specific immune response to an antigen of a pathogen, for example, a bacterial or viral pathogen, or to a cellular constituent correlated with a pathological condition. A vaccine may include a polynucleotide, a peptide or polypeptide, a virus, a bacteria, a cell or one or more cellular constituents. In some cases, the virus, bacteria or cell may be inactivated or attenuated to prevent or reduce the likelihood of infection, while maintaining the immunogenicity of the vaccine constituent.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker gene and other genetic elements known in the art.

Virus: Microscopic infectious organism that reproduces inside living cells. A virus consists essentially of a core of a single nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so.

"Retroviruses" are RNA viruses wherein the viral genome is RNA. When a host cell is infected with a retrovirus, the genomic RNA is reverse transcribed into a DNA intermediate which is integrated very efficiently into the chromosomal DNA of infected cells. The integrated DNA intermediate is referred to as a provirus. The term "lentivirus" is used in its conventional sense to describe a genus of viruses containing reverse transcriptase. The lentiviruses include the "immunodeficiency viruses" which include human immunodeficiency virus (HIV) type 1 and type 2 (HIV-1 and HIV-2), simian immunodeficiency virus (SIV), and feline immunodeficiency virus (FIV). HIV-1 is a retrovirus that causes immunosuppression in humans (HIV disease), and leads to a disease complex known as AIDS. "HIV infection" refers to the process in which HIV enters macrophages and CD4+ T cells by the adsorption of glycoproteins on its surface to receptors on the target cell followed by fusion of the viral envelope with the cell membrane and the release of the HIV capsid into the cell. "HIV disease" refers to a well-recognized constellation of signs and symptoms (including the development of opportunistic infections) in persons who are infected by an HIV virus, as determined by antibody or western blot studies. Laboratory findings associated with this disease are a progressive decline in T cells.

Virus-like particle or VLP: A nonreplicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art. The presence of VLPs following recombinant expression of viral proteins can be detected using conventional techniques known in the art, such as by electron microscopy, biophysical characterization, and the like. See, for example, Baker et al. (1991) *Biophys. J.* 60:1445-1456; Hagensee et al. (1994) *J. Virol.* 68:4503-4505. For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions.

II. Description of Several Embodiments

Historically, viral vaccines have been live-attenuated or chemically inactivated forms of the virus. However, this approach has limited utility when used for HIV. Recombinant HBsAg-gp120 has been used to present approximately amino acids 1-500 of gp120. However, the presentation of gp120 in this form has not successfully been used to produce neutralizing antibodies.

Human monoclonal antibodies to the MPR of gp41 can neutralize very broadly, including virtually all HIV isolates in North America and Western Europe. Therefore, many researchers have tried to express the MPR determinant in ways that could elicit neutralizing antibodies similar to the two monoclonals specific for this site which were obtained from infected humans. However, immunization has failed to elicit these antibodies. Without being bound by a particular theory, the inability to elicit neutralizing antibodies may be due to improper orientation of the MPR on the lipid surface.

The inventors have developed isolated immunogens including a variant HBsAg. HBsAg was selected as a carrier protein because it spontaneously assembles into virus-like particles. These particles have a lipid layer, and HBsAg embeds itself in the lipid layer, which it spans four times. The disclosed variant HBsAgs include a HBsAg with one or more transmembrane domains of the HBsAg replaced with a gp41 antigenic insert. The gp41 antigenic insert includes the MPR of gp41 and a transmembrane region of gp41. The replacement of a membrane spanning domain of HBsAg, such as the first and/or third transmembrane domains, with a membrane spanning domain of gp41 anchors gp41 into HBsAg particles in virtually the identical orientation as on HIV virions and correctly orients the nearby MPR on the lipid layer. The disclosed HBsAg variants are readily recognized by human monoclonal antibodies, 2F5, 4E10, and Z13e, which bind and neutralize a broad spectrum of HIV isolates. Thus, the disclosed particles display the neutralization-sensitive MPR in association with a lipid layer, while presenting it at the most immunogenic site on HBsAg. The results show that HBsAg is remarkably flexible in particle formation, and it can assemble particles, even with the new membrane spanning domain in place.

Disclosed herein is the use of the immunogenic HBsAg particulate platform to array epitopes from the conserved, neutralization-sensitive MPR of HIV-1, and the use of this platform to induce an immune response to HIV-1 using specific antigenic epitopes of gp41. Specifically, it is disclosed herein that the HBsAg can be used as a carrier, for example in a multi-array presentation of the antigenic components of the HIV envelope protein (env), such as to induce an immune response to highly conserved, hydrophobic 2F5 and 4E10 neutralizing determinants from gp41. In addition, the use of the HBsAg platform allows presentation of the MPR as an immunogen in an appropriate lipid context.

A. Isolated Immunogens with Variant HBsAgs

Isolated immunogens including variant HBsAgs are disclosed. In an example, a variant HBsAg includes an HBsAg with one or more transmembrane domains of the HBsAg replaced with a gp41 transmembrane spanning domain and/or one or more gp41 MPRs. The replacement of a membrane spanning domain of HBsAg with a membrane spanning domain of gp41 anchors gp41 into HBsAg in virtually the identical orientation as on HIV virions and correctly orients the nearby MPR on the lipid layer. Thus, the disclosed variant HBsAgs display the neutralization-sensitive MPR in association with a lipid layer, while presenting it at the most immunogenic site on HBsAg.

Suitable amino acid sequences for HBsAg are known in the art, and are disclosed, for example, in PCT Publication No. WO 2002/079217, which is incorporated herein by reference. Additional sequences for hepatitis B surface antigen can be found, for example, in PCT Publication No. 2004/113369 and PCT Publication No. WO 2004/09849. An exemplary HBsAg amino acid sequence, and the sequence of a nucleic acid encoding HBsAg, is shown in Berkower et al., *Virology* 321: 74-86, 2004, which is incorporated herein by reference in its entirety. An amino acid sequence of an exemplary HBsAg is set forth as follows:

(SEQ ID NO: 31)
EFITSGFLGPLLVLQAGFFLLTRILTIPQSLDSWWTSLNFLGGSPVCLGQ

NSQSPTSNHSPTSCPPICPGYRWMCLRRFIIFLFILLLCLIFLLVLLDYQ

GMLPVCPLIPGSTTTSTGPCKTCTTPAQGNSKFPSCCCTKPTDGNCTCIS

IPSSWAFAKYLWEWASVRFSWLSLLVPFVQWFVGLSPTVWLSAIWMMWYW

GPSLYSIVSPFIPLLPIFFCLWVYIG.

By itself, HBsAg assembles into approximately 22 nm virus-like particles. When expressed together with an HIV-1 antigenic epitope, the HBsAg fusion proteins assemble spontaneously and efficiently into virus-like particles (see Berkower et al., *Virology* 321: 75-86, 2004, which is incorporated herein by reference). Without being bound by theory, the multimeric form expresses the one or more antigenic epitopes at the lipid-water interface. These epitopes can be used to induce an immune response, such as to induce the production of neutralizing antibodies.

The preparation of hepatitis B surface antigen (HBsAg) is well documented. See, for example, Harford et al. (1983) *Develop. Biol. Standard* 54:125; Greg et al. (1987) *Biotechnology* 5:479; EP-A-0 226 846; and EP-A-0 299 108.

Fragments and variants of HBsAgs as disclosed herein are fragments and variants that retain the ability to spontaneously assemble into virus-like particles. By "fragment" of a HBsAg is intended a portion of a nucleotide sequence encoding a HBsAg, or a portion of the amino acid sequence of the protein. By "homologue" or "variant" is intended a nucleotide or amino acid sequence sufficiently identical to the reference nucleotide or amino acid sequence, respectively.

It is recognized that the gene or cDNA encoding a polypeptide can be considerably mutated without materially altering one or more of the polypeptide's functions. The genetic code is well known to be degenerate, and thus different codons encode the same amino acids. Even where an amino acid substitution is introduced, the mutation can be conservative and have no material impact on the essential functions of a protein (see Stryer, Biochemistry 4th Ed., W. Freeman & Co., New York, N.Y., 1995). Part of a polypeptide chain can be deleted without impairing or eliminating all of its functions. Sequence variants of a protein, such as a 5' or 3' variant, can retain the full function of an entire protein. Moreover, insertions or additions can be made in the polypeptide chain for example, adding epitope tags, without impairing or eliminating its functions (Ausubel et al., Current Protocols in Molecular Biology, Greene Publ. Assoc. and Wiley-Intersciences, 1998). Specific substitutions include replacing one or more transmembrane spanning domains of HBsAg with a gp41 transmembrane spanning domain, such replacing the first domain and/or third domain of HBsAg with a gp41 transmembrane spaning domain. Other modifications that can be made without materially impairing one or more functions of a polypeptide include, for example, in vivo or in vitro chemical and biochemical modifications or the incorporation of unusual amino acids. Such modifications include, for example, acetylation, carboxylation, phosphorylation, glycosylation, ubiquination, labeling, such as with radionucleides, and various enzymatic modifications, as will be readily appreciated by those well skilled in the art. A variety of methods for labeling polypeptides and labels useful for such purposes is well known in the art, and includes radioactive isotopes such as $^{32}P$, ligands that bind to or are bound by labeled specific binding partners (such as antibodies), fluorophores, chemiluminescent agents, enzymes, and antiligands.

Functional fragments and variants of HBsAg include those fragments and variants that are encoded by nucleotide sequences that retain the ability to spontaneously assemble into virus-like particles. Functional fragments and variants can be of varying length. For example, a fragment may consist of 10 or more, 25 or more, 50 or more, 75 or more, 100 or more, or 200 or more amino acid residues of a HBsAg amino acid sequence.

A functional fragment or variant of HBsAg is defined herein as a polypeptide that is capable of spontaneously assembling into virus-like particles and/or self-aggregating into stable multimers. This includes, for example, any polypeptide six or more amino acid residues in length that is capable of spontaneously assembling into virus-like particles. Methods to assay for virus-like particle formation are well known in the art (see, for example, Berkower et al. (2004) *Virology* 321:75-86, herein incorporated by reference in its entirety).

"Homologues" or "variants" of a hepatitis B surface antigen are encoded by a nucleotide sequence sufficiently identical to a nucleotide sequence of hepatitis B surface antigen, examples of which are described above. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98% or 99% sequence identity over its full length as compared to a reference sequence, for example using the NCBI Blast 2.0 gapped BLAST set to default parameters. Alignment may also be performed manually by inspection. For comparisons of amino acid sequences of greater than about 30 amino acids, the Blast 2 sequences function is employed using the default BLOSUM62 matrix set to default parameters (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). In one embodiment, the HBsAg protein is at least about 85%, at least about 90%, at least about 95%, at least about 96%, at least about 97%, at least about 98%, at least about 99% identical to the polypeptide of SEQ ID NO: 31.

One or more conservative amino acid modifications can be made in the HBsAg amino acid sequence, whether an addition, deletion or modification, that does not substantially alter the 3-dimensional structure of the polypeptide. For example, a conservative amino acid substitution does not affect the ability of the HBsAg polypeptide to self-aggregate into stable multimers. HBsAg proteins having deletions of a small number of amino acids, for example, less than about 10% (such as less than about 8%, or less than about 5%, or less than about 2%, or less than about 1%) of the total number of amino acids in the wild type HBsAg protein can also be included in the fusion proteins described herein. The deletion may be a terminal deletion, or an internal deletion, so long as the deletion does not substantially affect the structure or aggregation of the fusion protein.

In certain embodiments, a variant HBsAg can include a linker sequence. This peptide is a short amino acid sequence providing a flexible linker that permits attachment of an antigenic polypeptide without disruption of the structure, aggregation (multimerization) or activity of the self-aggregating polypeptide component. Typically, a linear linking peptide consists of between two and 25 amino acids. Usually, the linear linking peptide is between two and 15 amino acids in length. In one example, the linker polypeptide is two to three amino acids in length, such as a serine and an arginine, or two serine residues and an arginine residue, or two arginine residues and a serine residue.

In other examples, the linear linking peptide can be a short sequence of alternating glycines and prolines, such as the amino acid sequence glycine-proline-glycine-proline. A linking peptide can also consist of one or more repeats of the sequence glycine-glycine-serine. Alternatively, the linear linking peptide can be somewhat longer, such as the glycine (4)-serine spacer described by Chaudhary et al., *Nature* 339: 394-397,1989.

Directly or indirectly adjacent to the remaining end of the linear linking peptide (that is, the end of the linear linking peptide not attached to the self-aggregating polypeptide component of the fusion protein) is a polypeptide sequence including at least one antigenic epitope of HIV-1, such as an epitope of gp41, such as at least one antigenic epitope of the membrane proximal region. The antigenic polypeptide can be a short peptide sequence including a single epitope. For example the antigenic polypeptide can be a sequence of amino acids as short as eight or nine amino acids, sufficient in length to provide an antigenic epitope in the context of presentation by a cellular antigen presenting complex, such as the major histocompatibility complex (MHC). The antigenic polypeptide can also be of sufficient in length to induce antibodies, such as neutralizing antibodies. Larger peptides, in excess of 10 amino acids, 20 amino acids or 30 amino acids are also suitable antigenic polypeptides, as are much larger polypeptides provided that the antigenic polypeptide does not disrupt the structure or aggregation of the HBsAg polypeptide component.

In some examples, the variant HBsAg includes one or more epitopes of the envelope protein of HIV-1, and is about 20 to about 200 amino acids in length, such as about 25 to about 150 amino acids in length, such as about 25 to about 100 amino acids in length. In several additional examples, the antigenic polypeptide includes one or more antigenic epitopes of HIV-1 gp41, such as the membrane proximal region (MPR) of gp41.

Exemplary sequences for HIV-1, as well as the amino acid sequence for full-length gp41 can be found on Genbank, EMBL and SwissProt websites. Exemplary non-limiting sequence information can be found for example, as SwissProt Accession No. P04578, (includes gp41 and gp120, initial entry Aug. 13, 1987, last modified on Jul. 15, 1999); Genbank Accession No. HIVHXB2CG (full length HIV-1, including RNA sequence and encoded proteins, Oct. 21, 2002); Genbank Accession No. CAD23678 (gp41, Apr. 15, 2005); Genbank Accession No. AAF69493 (Oct. 2, 2000, gp120); Genbank Accession No. CAA65369 (Apr. 18, 2005); all of which are incorporated herein by reference. Similar information is available for HIV-2.

Suitable Env proteins are known in the art and include, for example, gp160, gp120, gp41, and gp140. Any clade of HIV is appropriate for antigen selection, including HIV clades A, B, C, and the like. HIV Gag, Pol, Nef and/or Env proteins from HIV clades A, B, C, as well as nucleic acid sequences encoding such proteins and methods for the manipulation and insertion of such nucleic acid sequences into vectors, are known (see, for example, HIV Sequence Compendium, Division of AIDS, National Institute of Allergy and Infectious Diseases, 2003, HIV Sequence Database (on the world wide web at hiv-web.lanl.gov/content/hiv-db/mainpage.html), Sambrook et al., *Molecular Cloning, a Laboratory Manual*, 2d edition, Cold Spring Harbor Press, Cold Spring Harbor, N.Y., 1989, and Ausubel et al., *Current Protocols in Molecular Biology*, Greene Publishing Association. Exemplary Env polypeptides, for example, corresponding to clades A, B and C are represented by the sequences of Genbank® Accession Nos. U08794, K03455 and AF286227, respectively.

Variant HBsAgs can form a self-aggregating multimeric ring structure upon expression in a host cell. Similarly, the variant HBsAgs can assemble spontaneously (self-aggregate) when placed in suspension in a solution of physiological pH (for example, a pH of about 7.0 to 7.6). Thus, in the present disclosure, wherever a single or monomeric variant HBsAg is disclosed, polymeric forms are also considered to be described.

In some embodiments, an isolated immunogen includes a variant HBsAg with one or more transmembrane domains of the HBsAg replaced with a gp41 antigenic insert. The gp41 antigenic insert can include (a) an antigenic polypeptide fragment of gp41 and (b) a transmembrane domain of gp41. In an example, the gp41 antigenic insert includes (a) an antigenic polypeptide fragment, such as an antigenic polypeptide fragment with the amino acid sequence set forth in SEQ ID NO:1 and is between 28 and 150 amino acids in length and (b) a transmembrane spanning gp41 region, such as a transmembrane spanning gp41 region with the amino acid sequence set forth in SEQ ID NO: 25 (in which wherein $X_1$, $X_2$, $X_3$, and $X_4$ are any amino acid and $X_5$, $X_6$, and $X_7$ are any hydrophobic amino acid) and is between 22 and 40 amino acids in length.

In one example, the antigenic polypeptide includes the amino acid sequence of NEX$_1$X$_2$LLX$_3$LDKWASLWNWFDITNWLWYIX$_4$ (SEQ ID NO: 1). In this sequence, $X_1$, $X_2$ $X_3$, and $X_4$ are any amino acid. The antigenic epitope can include repeats of this sequence, such as one to five copies of SEQ ID NO: 1. As noted above, the antigenic peptide includes one or more epitopes of the envelope protein of HIV-1, and, including SEQ ID NO: 1, can be from about 28 to about 200 amino acids in length, such from about 28 to about 150 amino acids in length, such as from about 28 to about 140 amino acids in length.

In several examples, the antigenic polypeptide includes one or more of the amino acid sequences set forth below:

a) (NEQELLALDKWASLWNWFDITNWLWYIK); SEQ ID NO: 2
b) (NEQDLLALDKWASLWNWFDITNWLWYIK); SEQ ID NO: 3
c) (NEQDLLALDKWANLWNWFDISNWLWYIK); SEQ ID NO: 4
d) (NEQDLLALDKWANLWNWFNITNWLWYIR); SEQ ID NO: 5
e) (NEQELLELDKWASLWNWFDITNWLWYIK); SEQ ID NO: 6
f) (NEKDLLALDSWKNLWNWFDITNWLWYIK); SEQ ID NO: 7
g) (NEQDLLALDSWENLWNWFDITNWLWYIK); SEQ ID NO: 8
h) (NEQELLELDKWASLWNWFSITQWLWYIK); SEQ ID NO: 9
i) (NEQELLALDKWASLWNWFDISNWLWYIK); SEQ ID NO: 10
j) (NEQDLLALDKWDNLWSWFTITNWLWYIK); SEQ ID NO: 11
k) (NEQDLLALDKWASLWNWFDITKWLWYIK); SEQ ID NO: 12
l) (NEQDLLALDKWASLWNWFSITNWLWYIK); SEQ ID NO: 13
m) (NEKDLLELDKWASLWNWFDITNWLWYIK); SEQ ID NO: 14
n) (NEQEILALDKWASLWNWFDISKWLWYIK); SEQ ID NO: 15
o) (NEQDLLALDKWANLWNWFNISNWLWYIK); SEQ ID NO: 16
p) (NEQDLLALDKWASLWSWFDISNWLWYIK); SEQ ID NO: 17
q) (NEKDLLALDSWKNLWSWFDITNWLWYIK); SEQ ID NO: 18
r) (NEQELLQLDKWASLWNWFSITNWLWYIK); SEQ ID NO: 19
s) (NEQDLLALDKWASLWNWFDISNWLWYIK); SEQ ID NO: 20
t) (NEQELLALDKWASLWNWFDISNWLWYIR); SEQ ID NO: 21
u) (NEQELLELDKWASLWNWFNITNWLWYIK); SEQ ID NO: 22
v) (NEKELLELDKWASLWNWFDITNWLWYI) as in the TM 12 construct; SEQ ID NO: 23
w) (NEKELLELDKWASLWNWFDITNWLWYIR) as in the TM14, TM16 or TM20 construct; SEQ ID NO: 24
x) (NEKELLELDKWASLW) as repeated four times in the TM32F construct; or SEQ ID NO: 60
y) (NEKELLELDKWASLWNWFDITNWLW) as in the TM34 constuct. SEQ ID NO: 61

The antigenic polypeptide can include one of the amino acid sequences set forth as SEQ ID NOs: 2-24 or 60, 61. A single copy of one of SEQ ID NOs: 2-24 or 60, 61 can be included as the antigenic polypeptide. Alternatively, multiple copies of one of SEQ ID NOs: 2-24, 60 or 61 can be included as the antigenic polypeptide. Thus, one, two, three, four or five copies or more of one of the amino acid sequences set forth as SEQ ID NOs: 2-24, 60 or 61 can be included as the antigenic polypeptide.

In additional embodiments, more than one of these sequences can be included in the antigenic polypeptide. Thus, in several examples, two, three, four, five or more of the amino acid sequences set forth as SEQ ID NOs: 2-24, 60 or 61 can be included as the antigenic polypeptide. Each amino acid sequence included in the antigenic polypeptide can be present only a single time, or can be repeated.

In some embodiments, the transmembrane spanning gp41 region includes the amino acid sequence set forth in SEQ ID NO: 25. In this sequence, $X_1$, $X_2$, $X_3$, and $X_4$ are any amino acid and $X_5$, $X_6$, and $X_7$ and the transmembrane spanning gp41 region is between 22 and 40 amino acids in length. In several examples, the antigenic polypeptide includes one or more of the amino acid sequences set forth below:

```
a)  (IFIMIVGGLIGLRIVFTVLSIV)    SEQ ID NO: 26 b)  (LFIMIVGGLIGLRIVFTALSIV);   SEQ ID NO: 27
or c)  (IFIMIVGGLVGLRIVFTALSIV)    SEQ ID NO: 28
```

The HBsAg variants can include one or more transmembrane spanning domains that include one of the amino acid sequences set forth as SEQ ID NOs: 26-28. A single gp41 transmembrane can be included in the variant HBsAg. Alternatively, multiple gp41 transmembrane domains with amino acid sequences set forth as SEQ ID NOs: 26-28 can be included within the variant HBsAg. Thus, one, two, three, four or five gp41 transmembrane domains with one of the amino acid sequences set forth as SEQ ID NOs: 26-28 can be included in the variant HBsAg.

In one particular embodiment, an isolated immunogen includes a variant HBsAg in which the first transmembrane spanning domain of the HBsAg is replaced by a gp41 antigenic insert. For example, the gp41 antigenic insert replaces at least the first 29 amino acid residues of SEQ ID NO:31, for example amino acid residues 1-35 of SEQ ID NO: 31. In another example, the gp41 antigenic insert replaces amino acid residues 1-32 of SEQ ID NO: 31. In yet another example, the gp41 antigenic insert replaces amino acid residues 1-29 of SEQ ID NO: 31. In a particular example, an isolated immunogen includes a variant HBsAg in which the first transmembrane spanning domain of the HBsAg is replaced by a gp41 antigenic insert that has the amino acid sequence set forth as SEQ ID NO: 29.

In another particular embodiment, an isolated immunogen includes a variant HBsAg in which the third transmembrane spanning domain of the HBsAg is replaced by a gp41 antigenic insert. For example, the gp41 antigenic insert replaces at least 29 amino acids residues of SEQ ID NO: 31, for example amino acid residues 150-190 of SEQ ID NO: 31. In another example, the gp41 antigenic insert replaces amino acid residues 153-187 of SEQ ID NO: 31. In yet another example, the gp41 antigenic insert replaces amino acid residues 156-185 of SEQ ID NO: 31. In a particular example, an isolated immunogen including a variant HBsAg in which the third transmembrane spanning domain of the HBsAg is replaced by a gp41 antigenic insert has the amino acid sequence set forth as SEQ ID NO: 57 or an amino acid sequence that is at least 80%, at least 85%, at least 90%, at least 95%, or at least 98% sequence similarity, such as 80%, 82%, 85%, 87%, 90%, 93%, 95% or 98% sequence similarity with such sequence.

In an even more particular embodiment, an isolated immunogen includes a variant HBsAg in which more than one transmembrane spanning domain of HBsAg has been replaced with an antigenic insert. In one example, an isolated immunogen includes a varaint HBsAg in which the first and the third transmembrane spanning domains of the HBsAg are replaced by a gp41 antigenic insert. For example, the gp41 antigenic insert replaces amino acid residues 1-35 and 150-190 of SEQ ID NO: 31. In another example, the gp41 antigenic insert replaces amino acid residues 1-32 and 153-187 of SEQ ID NO: 31. In yet another example, the gp41 antigenic insert replaces amino acid residues 1-29 and 156-185 of SEQ ID NO: 31.

In one example of an isolated immunogen, the first transmembrane domain of HBsAg is replaced with the MPR and transmembrane domain of gp41 and has the amino acid sequence set forth as:

```
                              (SEQ ID NO: 29; TM16)
MKTIIALSYIFCLVFAQDLPGNDNNSEFNEKELLELDKWASLWNWFDITN

WLWYIRLFIMIVGGLIGLRIVFAVLSIPQSLDSWWTSLNFLGGSPVCLGQ

NSQSPTSNHSPTSCPPICPGYRWMCLRRFIIFLFILLLCLIFLLVLLDYQ

GMLPVCPLIPGSTTTSTGPCKTCTTPAQGNSKFPSCCCTKPTDGNCTCIP

IPSSWAFAKYLWEWASVRFSWLSLLVPFVQWFVGLSPTVWLSAIWMMWYW

GPSLYSIVSPFIPLLPIFFCLWVYIG.
```

In one example of an isolated immunogen, the third transmembrane domain of HBsAg is replaced with the MPR and transmembrane domain of gp41 and such immunogen has the amino acid sequence set forth as:

```
                              (SEQ ID NO: 57; TM20)
MKTIIALSYIFCLVFAQDLPGNDNNSEFITSGFLGPLLVLQAGFFLLTRI

LTIPQSLDSWWTSLNFLGGSPVCLGQNSQSPTSNHSPTSCPPICPGYRWM

CLRRFIIFLFILLLCLIFLLVLLDYQGMLPVCPLIPGSTTTSTGPCKTCT

TPAQGNSKFPSCCCTKPTDGNCTCININEKELLELDKWASLWNWFDITNW

LWYIRLFIMIVGGLIGLRIVFAVLSIVVGLSPTVWLSAIWMMWYWGPSLY

SIVSPFIPLLPIFFCLWVYIG.
```

In an example, an isolated immunogen is provided in which the first transmembrane domain and third domain of HBsAg is each replaced with the MPR and transmembrane domain of gp41 and has the amino acid sequence set forth as:

```
                              (SEQ ID NO: 58; TM16 + TM20)
••••••••••••••••••••••••••••••••••••••••••••••
MKTIIALSYIFCLVFAQDLPGNDNNSEFNEKELLELDKWASLWNWFDITN

••••••••••••••••••••••••••••••••••••••••••••••
WLWYIRLFIMIVGGLIGLRIVFAVLSIPQSLDSWWTSLNFLGGSPVCLGQ

••••••••••••••••••••••••••••••••••••••••••••••
NSQSPTSNHSPTSCPPICPGYRWMCLRRFIIFLFILLLCLIFLLVLLDYQ

••••••••••••••••••••••••••••••••••••••••••••••
GMLPVCPLIPGSTTTSTGPCKTCTTPAQGNSKFPSCCCTKPTDGNCTCIP
```

INEKELLELDKWASLWNWFDITNWLWYIRLFIMIVGGLIGLRIVFAVLSI

••••••••••••••••••••••••••••••••••••••••
VVGLSPTVWLSAIWMMWYWGPSLYSIVSPFIPLLPIFFCLWVYIG.

In one example, an isolated immunogen is provided in which the second and third domain of HBsAg is replaced with a MPR and has the amino acid sequence set forth as:

(SEQ ID NO: 56; TM34)
MKTIIALSYIFCLVFAQDLPGNDNNSEFITSGFLGPLLVLQAGFFLLTRI

LTIPQSLDSWWTSLNFLGGSPVCLGQNSQSPTSNHSPTSCPPICPGYRWM

CLRRFIIFLFILLLCLIFLLVLLDYQGMLPVCPLIPGSTTTSTGPCKTCT

TPAQGNSKFPSCCCTKPTDGNCTCISINEKELLELDKWASLWNWFDITNW

LWSSLWAIKYLWEWASVRFSWLSLLVPFVQWFVGLSPTVWLSAIWMMWYW

GPSLYSIVSPFIPLLPIFFCLWVYIG

In one example, an isolated immunogen is provided in which the first domain of HBsAg is replaced with a MPR and transmembrane domain of gp41 and the domain between the second and third domain of HBsAg is replaced with a MPR and has the amino acid sequence set forth as:

(SEQ ID NO: 62; TM16 + TM34)
MKTIIALSYIFCLVFAQDLPGNDNNSEFNEKELLELDKWASLWNWFDITN

WLWYIRLFIMIVGGLIGLRIVFAVLSIPQSLDSWWTSLNFLGGSPVCLGQ

NSQSPTSNHSPTSCPPICPGYRWMCLRRFIIFLFILLLCLIFLLVLLDYQ

GMLPVCPLIPGSTTTSTGPCKTCTTPAQGNSKFPSCCCTKPTDGNCTCIS

INEKELLELDKWASLWNWFDITNWLWSSLWAIKYLWEWASVRFSWLSLLV

PFVQWFVGLSPTVWLSAIWMMWYWGPSLYSIVSPFIPLLPIFFCLWVYIG

In one example, an isolated immunogen is provided in which four MPRs are inserted between a second and third domain in the HBsAg construct and has the amino acid sequence set forth as:

(SEQ ID NO: 63; TM32F)
MKTIIALSYIFCLVFAQDLPGNDNNSEFITSGFLGPLLVLQAGFFLLTRI

LTIPQSLDSWWTSLNFLGGSPVCLGQNSQSPTSNHSPTSCPPICPGYRWM

CLRRFIIFLFILLLCLIFLLVLLDYQGMLPVCPLIPGSTTTSTGPCKTCT

TPAQGNSKFPSCCCTKPTDGNCTCISINEKELLELDKWASLWAINEKELL

ELDKWASLWAINEKELLELDKWASLWAINEKELLELDKWASLWAIKYLWE

WASVRFSWLSLLVPFVQWFVGLSPTVWLSAIWMMWYWGPSLYSIVSPFIP

LLPIFFCLWVYIG

In one example, an isolated immunogen is provided in which the first domain of HBsAg is replaced with a MPR and transmembrane domain of gp41 and four additional MPRs are inserted between a second and third domain in the HBsAg construct and the construct has a sequence set forth as:

(SEQ ID NO: 64; TM16 + TM32F)
MKTIIALSYIFCLVFAQDLPGNDNNSEFNEKELLELDKWASLWNWFDITN

WLWYIRLFIMIVGGLIGLRIVFAVLSIPQSLDSWWTSLNFLGGSPVCLGQ

NSQSPTSNHSPTSCPPICPGYRWMCLRRFIIFLFILLLCLIFLLVLLDYQ

GMLPVCPLIPGSTTTSTGPCKTCTTPAQGNSKFPSCCCTKPTDGNCTCIS

INEKELLELDKWASLWAINEKELLELDKWASLWAINEKELLELDKWASLW

AINEKELLELDKWASLWAIKYLWEWASVRFSWLSLLVPFVQWFVGLSPTV

WLSAIWMMWYWGPSLYSIVSPFIPLLPIFFCLWVYIG.

The variant HBsAg can optionally include additional elements, such as a leader sequence (such as a leader sequence from influenza hemagglutinin, see, for example, SEQ ID NO: 30 as included within variant HBsAgs with amino acid sequences set forth by SEQ ID NOs: 29, 56-58 and 62-64) or a suitable T cell epitope. Generally, a T cell epitope is about eight to about ten amino acids in length, such as about nine amino acid in length, and binds major histocompatibility complex (MHC), such as HLA 2, for example, HLA 2.2. Examples of suitable T cell epitopes include, but are not limited to, ASLWNWFNITNWLWY (SEQ ID NO: 32) and IKLFIMIVGGLVGLR (SEQ ID NO: 33).

The variant HBsAg may also include a CAAX (SEQ ID NO: 34) sequence, for isoprenyl addition in vivo. In this sequence, C is cysteine, A is an aliphatic amino acid and X is any amino acid. The X residue determines which isoprenoid will be added to the cysteine. When X is a methionine or serine, the farnesyl-transferase transfers a farnesyl, and when X is a leucine or isoleucine, the geranygeranyl-transferase I, a geranylgeranyl group. In general, aliphatic amino acids have protein side chains containing only carbon or hydrogen atoms. Aliphatic amino acids include proline (P), glycine (G), alanine (A), valine (V), leucine (L), and isoleucine (I), presented in order from less hydrophobic to more hydrophobic. Although methionine has a sulphur atom in its side-chain, it is largely non-reactive, meaning that methionine effectively substitutes well with the true aliphatic amino acids.

B. Polynucleotides Encoding Variant HBsAgs

Nucleic acids encoding the variant HBsAgs described herein are also provided. These nucleic acids include deoxyribonucleotides (DNA, cDNA) or ribodeoxynucleotides (RNA) sequences, or modified forms of either nucleotide, which encode the variant HBsAgs described herein. The term includes single and double stranded forms of DNA and/or RNA. The nucleic acids can be operably linked to expression control sequences, such as, but not limited to, a promoter.

The nucleic acids that encode the variant HBsAgs disclosed herein include a polynucleotide sequence that encodes a variant HBsAgs including a HBsAg with one or more MPRs and/or one or more transmembrane domains of the HBsAg replaced with a gp41 antigenic insert.

In one example, nucleic acids that encode a variant HBsAg in which a third transmembrane domaine of HBsAg is replaced with a gp41 antigenic insert has the nucleotide sequence set forth as (SEQ ID NO: 59)
GGTACCGTCGACAGCAAAAGCAGGGGATAATTCTATTAACCATGAAGACT

ATCATTGCTTCCATGGCAGCTGTCGTTTTCGTCCCCTATTAAGATAATTG

GTACTTCTGATAGTAACGAATGAGCTACATTTTCTGTCTGGTTTTCGCCC

AAGACCTTCCAGGAAATGACAACAACAGCGACTCGATGTAAAAGACAGAC

CAAAAGCGGGTTCTGGAAGGTCCTTTACTGTTGTTGTCGCAATTCATCAC

-continued
```
CTCCGGCTTCCTGGGCCCCTGCTGGTCCTGCAGGCCGGGTTCTTCCTGC

TTAAGTAGTGGAGGCCGAAGGACCCGGGGGACGACCAGGACGTCCGGCCC

AAGAAGGACGTGACCCGCATCCTCACCATCCCCCAGTCCCTGGACTCGTG

GTGGACCTCCCTCAACTTTCACTGGGCGTAGGAGTGGTAGGGGGTCAGGG

ACCTGAGCACCACCTGGAGGGAGTTGAAAGTGGGGGGCTCCCCGTGTGT

CTGGGCCAGAACTCCCAGTCCCCCACCTCCAACCACTCCCACCCCCGAG

GGGGCACACAGACCCGGTCTTGAGGGTCAGGGGGTGGAGGTTGGTGAGGG

CCACCTCCTGCCCCCCCATCTGCCCCGGCTACCGCTGGATGTGCCTGCGC

CGCTTCATCAGGTGGAGGACGGGGGGGTAGACGGGGCCGATGGCGACCTA

CACGGACGCGGCGAAGTAGTTCTTCCTGTTCATCCTGCTGCTGTGCCTGA

TCTTCCTGCTGGTGCTGCTGGACTACCAGGAGAAGGACAAGTAGGACGAC

GACACGGACTAGAAGGACGACCACGACGACCTGATGGTCCGCATGCTGCC

CGTGTGCCCCCTGATCCCCGGCTCCACCACCACCTCCACCGGCCCCTGCA

CGTACGACGGGCACACGGGGGACTAGGGGCCGAGGTGGTGGTGGAGGTGG

CCGGGGACGTAGACCTGCACCACCCCCGCCCAGGGCAACTCCAAGTTCCC

CTCCTGCTGCTGCACCAAGCTCTGGACGTGGTGGGGCGGGTCCCGTTGA

GGTTCAAGGGGAGGACGACGACGTGGTTCGCCACCGACGGCAACTGCACC

TGCATCAATATTAATGAAAAGAATTATTGGAATTGGATAGGTGGCTGCC

GTTGACGTGGACGTAGTTATAATTACTTTTTCTTAATAACCTTAACCTAT

AATGGGCAAGTTTGTGGAATTGGTTTGACATAACAAACTGGCTGTGGTAT

ATAAGATTATTTACCCGTTCAAACACCTTAACCAAACTGTATTGTTTGAC

CGACACCATATATTCTAATATCATAATGATAGTAGGAGGCTTGATAGGTT

TAAGAATAGTTTTTGCTGTACTTTCTATAGAGTATTACTATCATCCTCCG

AACTATCCAAATTCTTATCAAAAACGACATGAAAGATATCTAGTGGGCCT

GTCCCCCACCGTGTGGCTGTCCGCCATCTGGATGATGTGGTACTGGGGCC

ATCACCCGGACAGGGGGTGGCACACCGACAGGCGGTAGACCTACTACACC

ATGACCCCGGCCTCCCTGTACTCCATCGTGTCCCCCTTCATCCCCCTGCT

GCCCATCTTCTTCTGCCTGTGGAGGGACATGAGGTAGCACAGGGGGAAGT

AGGGGGACGACGGGTAGAAGAAGACGGACAGGGTGTACATCTGACTAGTG

AGCTCCCCACATGTAGACTGATCACTCGAG.
```

The variant HBsAgs and the polynucleotides encoding them described herein can be used to produ ensure its proper splicing and polyadenylation. Vectors containing the promoter and enhancer regions of the SV40 or long terminal repeat (LTR) of the Rous Sarcoma virus and polyadenylation and splicing signal from SV40 are readily available (Mulligan et al., *Proc. Natl. Acad. Sci. USA* 78:1078-2076, 1981; Gorman et al., *Proc. Natl. Acad. Sci USA* 78:6777-6781, 1982). The level of expression of the cDNA can be manipulated with this type of vector, either by using promoters that have different activities (for example, the baculovirus pAC373 can express cDNAs at high levels in *S. frugiperda* cells (Summers and Smith, In *Genetically Altered Viruses and the Environment*, Fields et al. (Eds.) 22:319-328, CSHL Press, Cold Spring Harbor, N.Y., 1985) or by using vectors that contain promoters amenable to modulation, for example, the glucocorticoid-responsive promoter from the mouse mammary tumor virus (Lee et al., *Nature* 294:228, 1982). The expression of the cDNA can be monitored in the recipient cells 24 to 72 hours after introduction (transient expression).

In addition, some vectors contain selectable markers such as the gpt (Mulligan and Berg, *Proc. Natl. Acad. Sci. USA* 78:2072-2076, 1981) or neo (Southern and Berg, *J. Mol. Appl. Genet.* 1:327-341, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses such as papilloma (Sarver et al., *Mol. Cell Biol.* 1:486, 1981) or Epstein-Barr (Sugden et al., *Mol. Cell Biol.* 5:410, 1985). Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product (Alt et al., *J. Biol. Chem.* 253:1357, 1978).

The transfer of DNA into eukaryotic, in particular human or other mammalian cells, is conventional. The vectors are introduced into the recipient cells as pure DNA (transfection) by, for example, precipitation with calcium phosphate (Graham and vander Eb, *Virology* 52:466, 1973) or strontium phosphate (Brash et al., *Mol. Cell Biol.* 7:2013, 1987), electroporation (Neumann et al., *EMBO J* 1:841, 1982), lipofection (Felgner et al., *Proc. Natl. Acad. Sci USA* 84:7413, 1987), DEAE dextran (McCuthan et al., *J. Natl. Cancer Inst.* 41:351, 1968), microinjection (Mueller et al., *Cell* 15:579, 1978), protoplast fusion (Schafner, *Proc. Natl. Acad. Sci. USA* 77:2163-2167, 1980), or pellet guns (Klein et al., *Nature* 327:70, 1987). Alternatively, the cDNA, or fragments thereof, can be introduced by infection with virus vectors. Systems are developed that use, for example, retroviruses (Bernstein et al., *Gen. Engr'g* 7:235, 1985), adenoviruses (Ahmad et al., *J. Virol.* 57:267, 1986), or Herpes virus (Spaete et al., *Cell* 30:295, 1982). Polynucleotides that encode proteins, such as variant HBsAgs, can also be delivered to target cells in vitro via non-infectious systems, for instance liposomes.

Using the above techniques, the expression vectors containing a polynucleotide encoding a variant HBsAgs as described herein or cDNA, or fragments or variants or mutants thereof, can be introduced into human cells, mammalian cells from other species or non-mammalian cells as desired. The choice of cell is determined by the purpose of the treatment. For example, monkey COS cells (Gluzman, *Cell* 23:175-182, 1981) that produce high levels of the SV40 T antigen and permit the replication of vectors containing the SV40 origin of replication may be used. Similarly, Chinese hamster ovary (CHO), mouse NIH 3T3 fibroblasts or human fibroblasts can be used.

The present disclosure, thus, encompasses recombinant vectors that comprise all or part of the polynucleotides encoding self-aggregating variant HBsAgs or cDNA sequences, for expression in a suitable host, either alone or as a labeled or otherwise detectable protein. The DNA is operatively linked in the vector to an expression control sequence in the recombinant DNA molecule so that the variant HBsAgs can be expressed. The expression control sequence may be selected from the group consisting of sequences that control the expression of genes of prokaryotic or eukaryotic cells and their viruses and combinations thereof. The expression control sequence may be specifically selected from the group consisting of the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

Any host cell can be transfected with the vector of this disclosure. Exemplary host cells include, but are not limited to *E. coli, Pseudomonas, Bacillus subtilis, Bacillus stearothermophilus* or other bacilli; other bacteria; yeast; fungi; insect; mouse or other animal; plant hosts; or human tissue cells.

Multimeric forms of a variant HBsAg ring can be recovered (such as for administration to a subject, or for other purposes) using any of a variety of methods known in the art for the purification of recombinant polypeptides. The variant HBsAgs disclosed herein can produced efficiently by transfected cells and can be recovered in quantity using any purification process known to those of skill in the art, such as a nickel (NTA-agarose) affinity chromatography purification procedure.

A variety of common methods of protein purification may be used to purify the disclosed variant HBsAgs. Such methods include, for instance, protein chromatographic methods including ion exchange, gel filtration, HPLC, monoclonal antibody affinity chromatography and isolation of insoluble protein inclusion bodies after over production. In one embodiment one or more purification affinity-tags, for instance a six-histidine sequence, is recombinantly fused to the protein, such as the variant HBsAg, and used to facilitate polypeptide purification (optionally, in addition to another functionalizing portion of the protein, such as a targeting domain or another tag, or a fluorescent protein, peptide, or other marker).

Commercially produced protein expression/purification kits provide tailored protocols for the purification of proteins made using each system. See, for instance, the QIAEXPRESS™ expression system from QIAGEN™ (Chatsworth, Calif.) and various expression systems provided by INVITROGEN™ (Carlsbad, Calif.). Where a commercial kit is employed to produce a protein, such as a variant HBsAg, the manufacturer's purification protocol is a preferred protocol for purification of that protein. For instance, proteins expressed with an amino-terminal hexa-histidine tag can be purified by binding to nickel-nitrilotriacetic acid (Ni-NTA) metal affinity chromatography matrix (*The QIAexpressionist*, QIAGEN, 1997).

C. Therapeutic Methods and Pharmaceutical Compositions

Polynucleotides encoding the variant HBsAgs disclosed herein, and variant HBsAgs, and the stable multimeric ring structures formed by polypeptides expressed from such polynucleotides can be administered to a subject in order to generate an immune response to HIV-1. In one example, the immune response is a protective immune response. Thus, the polynucleotides and polypeptides disclosed herein can be used in a vaccine, such as a vaccine to prevent subsequent infection with HIV.

A therapeutically effective amount of variant HBsAg, a polymeric form thereof, a viral particle including these variant HBsAgs, or a polynucleotide encoding one or more of these polypeptides can be administered to a subject to prevent, inhibit or to treat a condition, symptom or disease, such as acquired immunodeficiency syndrome (AIDS). In one example, polymeric ring structures formed by variant HBsAgs subunits are administered. In another example, one or more polynucleotides encoding at least one variant HBsAgs is administered. As such, the variant HBsAgs and polynucleotides encoding variant HBsAgs can be administered as vaccines to prophylactically or therapeutically induce or enhance an immune response. For example, the pharmaceutical compositions described herein can be administered to stimulate a protective immune response against HIV, such as a HIV-1.

A single administration can be utilized to prevent or treat an HIV infection, or multiple sequential administrations can be performed. In another example, more than one of the variant HBsAgs, multimeric forms of more than one variant HBsAgs, or multiple polynucleotides encoding the variant HBsAgs, are administered to a subject to induce an immune response to HIV-1. These polypeptides or polynucleotides can be administered simultaneously, or sequentially.

In exemplary applications, compositions are administered to a subject infected with HIV, or likely to be exposed to an infection, in an amount sufficient to raise an immune response to HIV. Administration induces a sufficient immune response to reduce viral load, to prevent or lessen a later infection with the virus, or to reduce a sign or a symptom of HIV infection. Amounts effective for this use will depend upon various clinical parameters, including the general state of the subject's health, and the robustness of the subject's immune system, amongst other factors. A therapeutically effective amount of the compound is that which provides either subjective relief of one or more symptom(s) of HIV infection, an objectively identifiable improvement as noted by the clinician or other qualified observer, a decrease in viral load, an increase in lymphocyte count, such as an increase in CD4 cells, or inhibition of development of symptoms associated with infection.

The variant HBsAgs, multimeric forms of the variant HBsAgs and polynucleotides encoding them can be administered by any means known to one of skill in the art (see Banga, A., "Parenteral Controlled Delivery of Therapeutic Peptides and Proteins," in *Therapeutic Peptides and Proteins*, Technomic Publishing Co., Inc., Lancaster, Pa., 1995) such as by intramuscular, subcutaneous, or intravenous injection, but even oral, nasal, or anal administration is contemplated. Variant HBsAgs, polymeric forms thereof, viral particles including the variant HBsAgs, or polynucleotides encoding the variant HBsAgs can be administered in a formulation including a carrier or excipient. A wide variety of suitable excipients are known in the art, including physiological phosphate buffered saline (PBS), and the like. Optionally, the formulation can include additional components, such as aluminum hydroxylphophosulfate, alum, diphtheria $CRM_{197}$, or liposomes. To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle. A particulate carrier based on a synthetic polymer has been shown to act as an adjuvant to enhance the immune response, in addition to providing a controlled release. Aluminum salts may also be used as adjuvants to produce an immune response.

In one embodiment, the variant HBsAgs or multimeric form thereof is mixed with an adjuvant containing two or more of a stabilizing detergent, a micelle-forming agent, and an oil. Suitable stabilizing detergents, micelle-forming agents, and oils are detailed in U.S. Pat. No. 5,585,103; U.S. Pat. No. 5,709,860; U.S. Pat. No. 5,270,202; and U.S. Pat. No. 5,695,770, all of which are incorporated by reference. A stabilizing detergent is any detergent that allows the components of the emulsion to remain as a stable emulsion. Such detergents include polysorbate, 80 (TWEEN) (Sorbitan-mono-9-octadecenoate-poly(oxy-1,2-ethanediyl; manufactured by ICI Americas, Wilmington, Del.), TWEEN 40™, TWEEN 20™, TWEEN 60~, ZWITTERGENT™ 3-12, TEEPOL HB7™, and SPAN 85™. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, for example, Schmolka, *J. Am. Oil. Chem. Soc.* 54:110, 1977; and Hunter et al., *J. Immunol* 129:1244, 1981, PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, *J. Immun.* 133:3167, 1984. The agent can be provided in an effective amount, for example between 0.5 and 10%, or in an amount between 1.25 and 5%.

The oil included in the composition is chosen to promote the retention of the antigen in oil-in-water emulsion, such as to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalene, Squalane, EICOSANE™, tetratetracontane, glycerol, and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse affects, such as granulomas, are evident upon use of the oil.

An adjuvant can be included in the composition. In one example, the adjuvant is a water-in-oil emulsion in which antigen solution is emulsified in mineral oil (such as Freund's incomplete adjuvant or montanide-ISA). In one embodiment, the adjuvant is a mixture of stabilizing detergents, micelle-forming agent, and oil available under the name PROVAX® (IDEC Pharmaceuticals, San Diego, Calif.). Other examples of suitable adjuvants are listed in the terms section of this specification.

In another embodiment, a pharmaceutical composition includes a nucleic acid encoding one or more variant HBsAgs as disclosed herein. A therapeutically effective amount of the immunogenic polynucleotide can be administered to a subject in order to generate an immune response, such as a protective immune response.

One approach to administration of nucleic acids is direct immunization with plasmid DNA, such as with a mammalian expression plasmid. As described above, the nucleotide sequence encoding a variant HBsAg can be placed under the control of a promoter to increase expression of the molecule. Suitable vectors are described, for example, in U.S. Pat. No. 6,562,376.

Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. No. 5,593,972 and U.S. Pat. No. 5,817,637 (which describe operatively linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids, and immune-stimulating constructs, or ISCOMS™, negatively charged cage-like structures of 30-40 nm in size formed spontaneously on mixing cholesterol and QUIL A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 μg encapsulated in ISCOMS™ have been found to produce Class I mediated CTL responses (Takahashi et al., *Nature* 344:873, 1990).

In another approach to using nucleic acids for immunization, a variant HBsAg as disclosed herein can also be expressed by an attenuated viral host or vector, or a bacterial vector. Recombinant adeno-associated virus (AAV), herpes virus, retrovirus, or other viral vectors can be used to express the peptide or protein, thereby eliciting a CTL response.

In one embodiment, a nucleic acid encoding the variant HBsAgs is introduced directly into cells. For example, the nucleic acid may be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites, including tissues subject to or in proximity to a site of infection. Dosages for injection are usually around 0.5 μg/kg to about 50 mg/kg, and typically are about 0.005 mg/kg to about 5 mg/kg (see, e.g., U.S. Pat. No. 5,589,466).

In one specific, non-limiting example, a pharmaceutical composition for intravenous administration, would include about 0.1 μg to 10 mg of a variant HBsAg per subject per day. Dosages from 0.1 pg to about 100 mg per subject per day can be used, particularly if the composition is administered to a secluded site and not into the circulatory or lymph system, such as into a body cavity or into a lumen of an organ. Actual methods for preparing administrable compositions will be known or apparent to those skilled in the art and are described in more detail in such publications as *Remingtons Pharmaceuticals Sciences,* $19^{th}$ Ed., Mack Publishing Company, Easton, Pa. (1995).

The compositions can be administered, either systemically or locally, for therapeutic treatments, such as to treat an HIV infection. In therapeutic applications, a therapeutically effective amount of the composition is administered to a subject infected with HIV, such as, but not limited to, a subject exhibiting signs or symptoms of AIDS. Single or multiple administrations of the compositions can be administered depending on the dosage and frequency as required and tolerated by the subject. In one embodiment, the dosage is administered once as a bolus, but in another embodiment can be applied periodically until a therapeutic result is achieved. Generally, the dose is sufficient to treat or ameliorate symptoms or signs of the HIV infection without producing unacceptable toxicity to the subject.

Controlled release parenteral formulations can be made as implants, oily injections, or as particulate systems. For a broad overview of protein delivery systems, see Banga, *Therapeutic Peptides and Proteins: Formulation, Processing, and Delivery Systems*, Technomic Publishing Company, Inc., Lancaster, Pa. (1995). Particulate systems include microspheres, microparticles, microcapsules, nanocapsules, nanospheres, and nanoparticles. Microcapsules contain the therapeutic protein as a central core. In microspheres, the therapeutic agent is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly (see Kreuter, *Colloidal Drug Delivery Systems*, J. Kreuter, ed., Marcel Dekker, Inc., New York, N.Y., pp. 219-342 (1994); Tice & Tabibi, *Treatise on Controlled Drug Delivery*, A. Kydonieus, ed., Marcel Dekker, Inc. New York, N.Y., pp. 315-339 (1992)).

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (e.g., U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; and U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342; and U.S. Pat. No. 5,534,496).

D. Immunodiagnostic Reagents and Kits

In addition to the therapeutic methods provided above, any of the variant HBsAgs disclosed herein can be utilized to produce antigen specific immunodiagnostic reagents, for example, for serosurveillance Immunodiagnostic reagents can be designed from any of the antigenic polypeptide described herein. For example, the presence of serum antibodies to HIV can be monitored using the isolated immunogens disclosed herein, such as to detect an HIV infection.

Generally, the method includes contacting a sample from a subject, such as, but not limited to a blood, serum, plama, urine or sputum sample from the subject with one or more of the variant HBsAgs disclosed herein (or a polymeric form thereof) and detecting binding of antibodies in the sample to the variant HBsAgs. The binding can be detected by any means known to one of skill in the art, including the use of labeled secondary antibodies that specifically bind the antibodies from the sample. Labels include radiolabels, enzymatic labels, and fluorescent labels.

Any such immunodiagnostic reagents can be provided as components of a kit. Optionally, such a kit includes additional components including packaging, instructions and various other reagents, such as buffers, substrates, antibodies or ligands, such as control antibodies or ligands, and detection reagents.

The disclosure is illustrated by the following non-limiting Examples.

EXAMPLES

Example 1

Variant HBsAg Including gp41 MPR Form Virus Like Particles

This example illustrates variant HBsAg constructs that are capable of forming virus like particles.

Figure 2B:
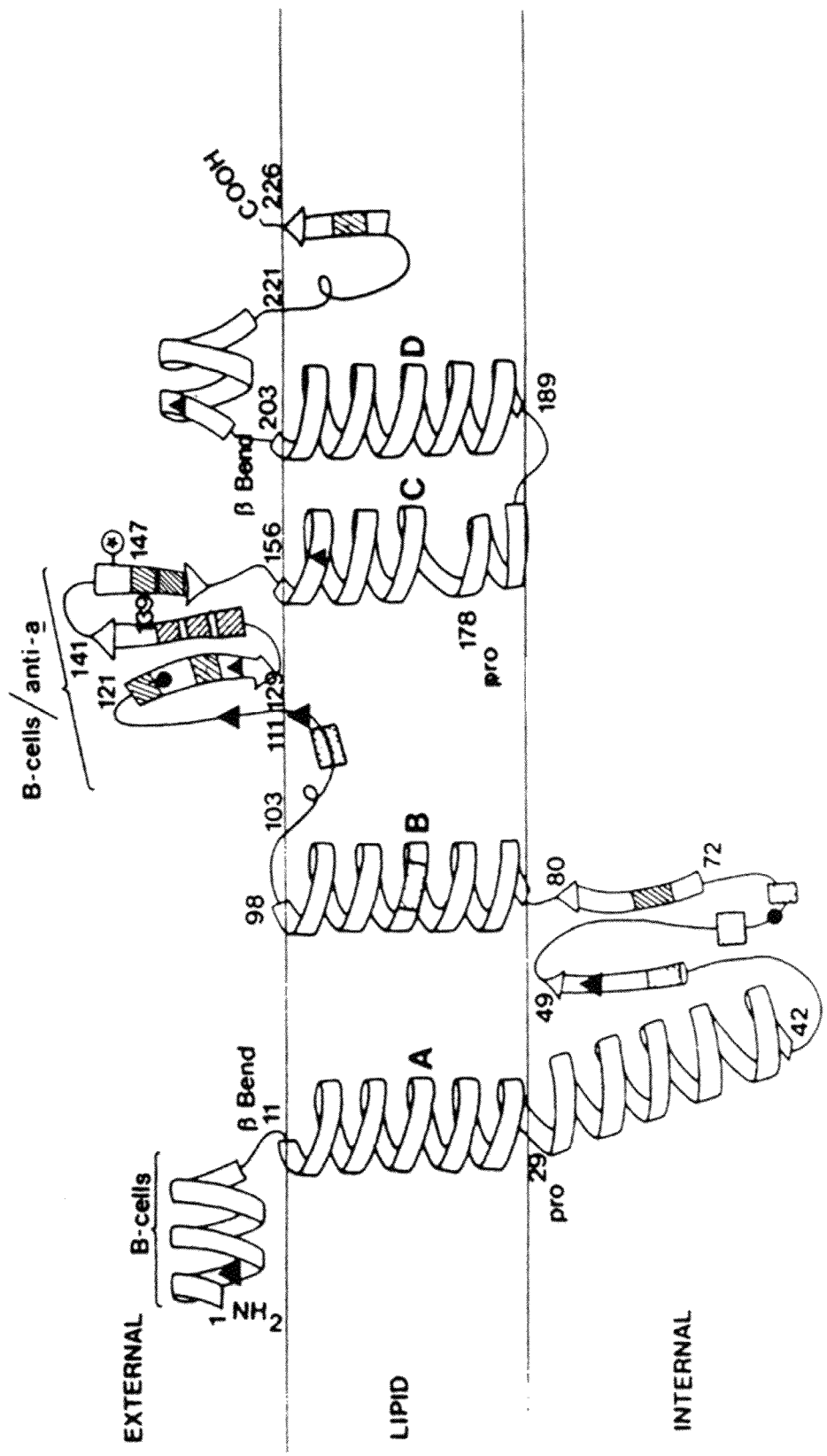
FIG. 2B is a schematic illustrating HBsAg including four transmembrane domains.
Figure 3A:
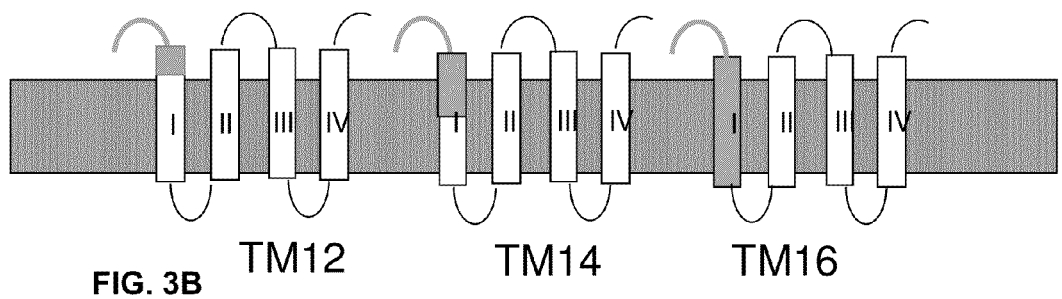
FIG. 3A is a diagram illustrating the insertion of various gp41 membrane spanning domains into the first membrane spanning domain of HBsAg.
Figure 9A:
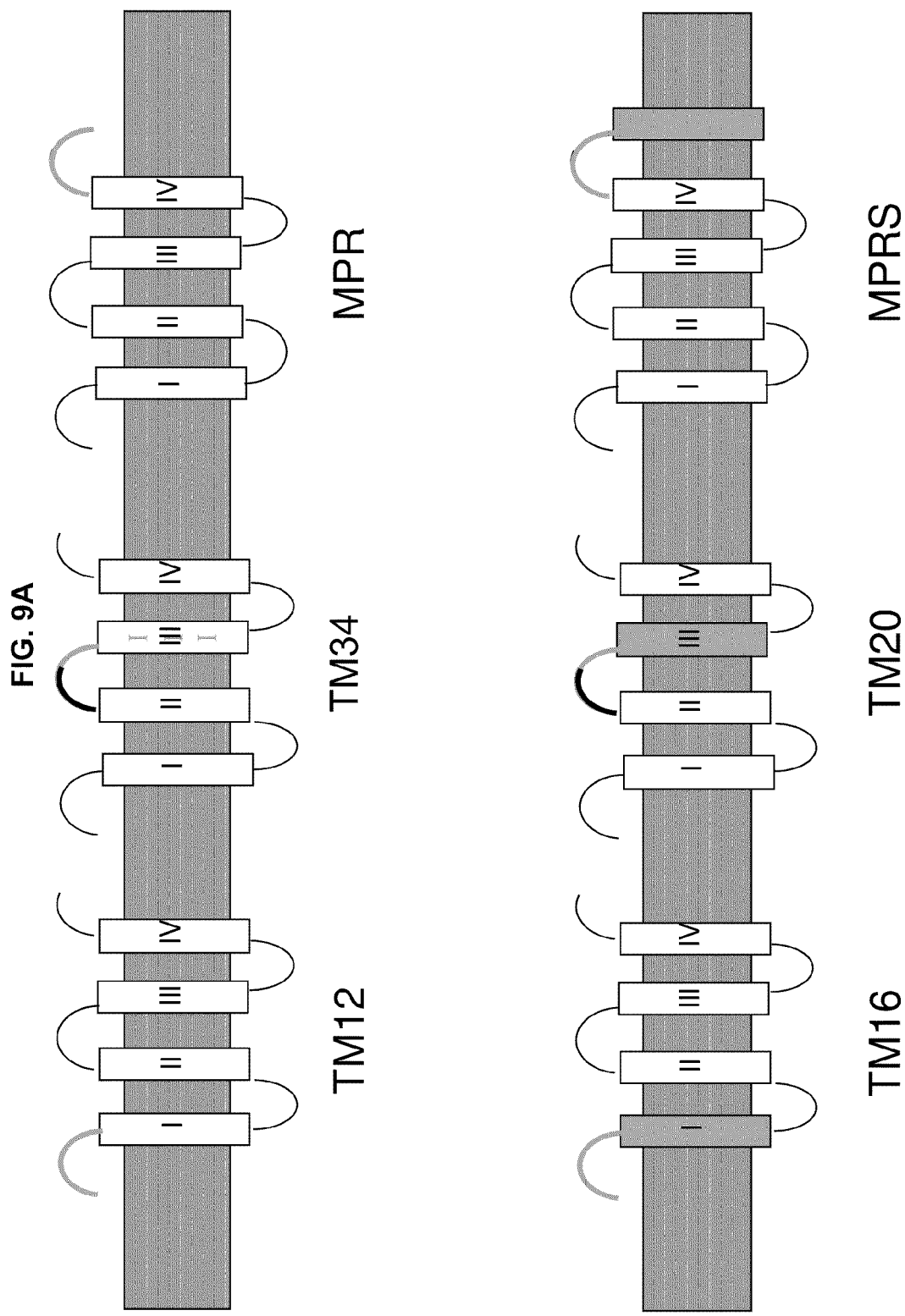
FIG. 9A is a series of schematics illustrating exemplary variant HBsAg constructs that assemble particles based on sedimentation studies (TM12, DA31-34, MPR, TM16, TM20 and MPRS) and electron microscopy (TM16).
Figure 10:
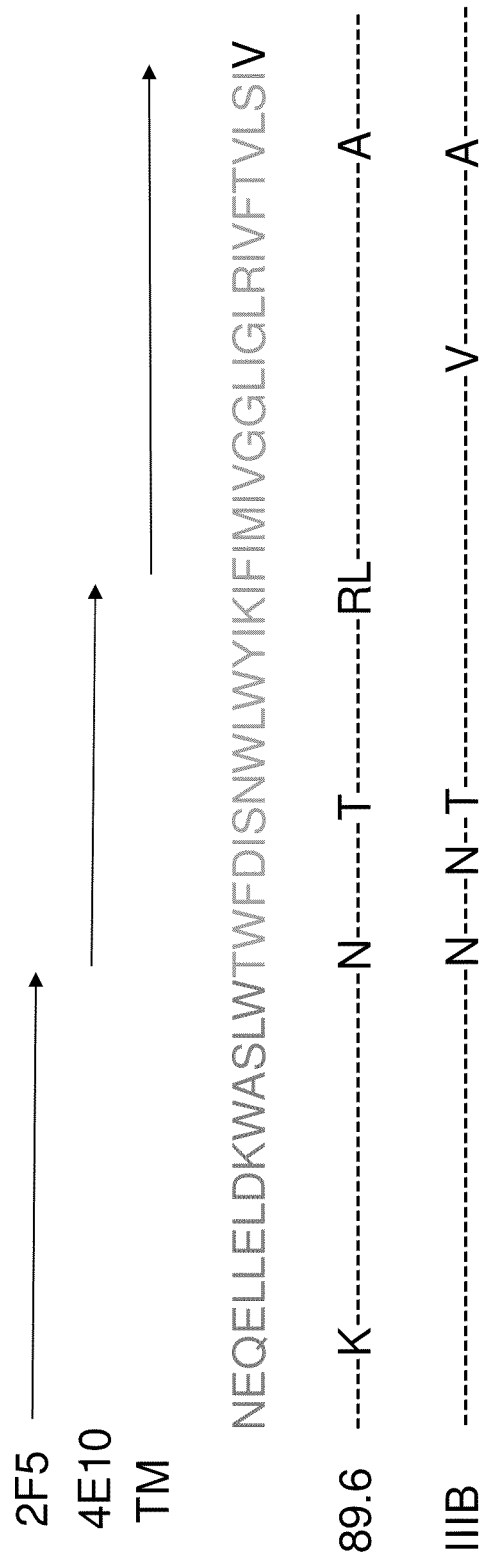
FIG. 10 is an illustration of an exemplary gp41 antigenic insert illustrating the MPR (SEQ ID NO: 1) and membrane spanning domain (SEQ ID NO: 25) of various inserts.

Variant HBsAg were prepared by substituting the MPR and/or membrane spanning domain of gp41 for various regions of the HBsAg (as illustrated in FIG. 2B), so that a gp41 MPR would be closely associated with the lipid layer of the particles (as illustrated in FIG. 1). For example, at the amino end of HBsAg, the first construct (TM12) included the external MPR domain of gp41 linked to the complete membrane spanning domain of HBsAg (FIG. 3A). The second construct (TM14) linked a MPR to HBsAg at a junction within the membrane spanning domain: it included six amino acids from the TM domain of gp41 and up to 14 amino acids from the membrane spanning domain of HBsAg (FIG. 3A). The third construct (TM16) linked MPR plus the entire TM domain of gp41 to HBsAg without any of its membrane spanning domain (FIGS. 2A and 3A). All three constructs contain antigenic determinants recognized by two monoclonal antibodies to gp41 (see, for example, FIG. 10), although they may differ in their contacts with the lipid surface. In the exposed middle loop of variant HBsAg constucts, the constructs expressed either the 2F5 epitope alone (TM32) or both the 2F5 and 4E10 epitopes (TM34). A third construct (TM32F) expressed four copies of the 2F5 epitope in tandem. In construct TM20 (FIG. 9A), the entire third membrane spanning domain of HBsAg was replaced with the transmembrane domain of gp41, while including the epitopes for 2F5 and 4E10.

Figure 3B:
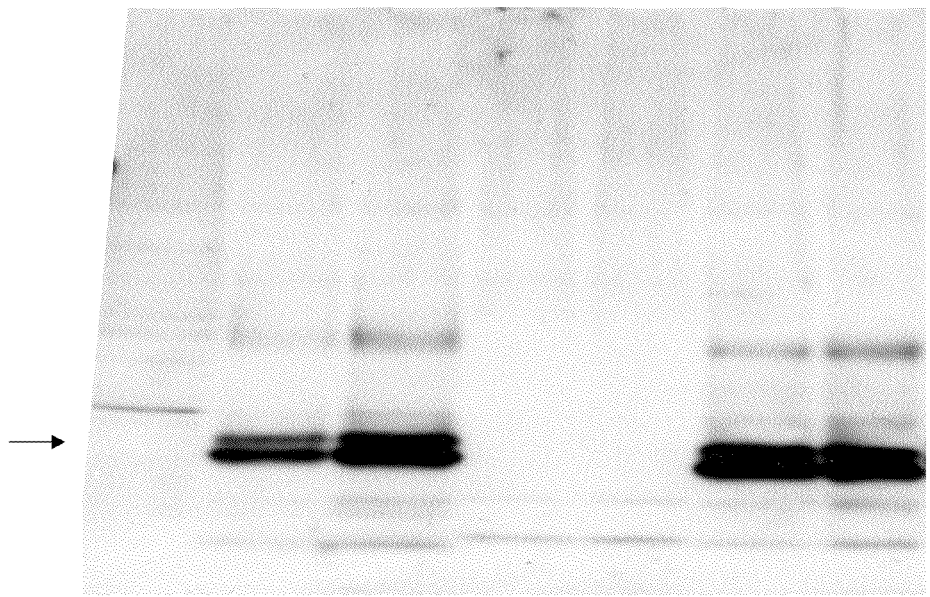
FIG. 3B is a digital image of a gel illustrating MPR expression in HBsAg when gp41 is substituted for the beginning of the first transmembrane domain of HBsAg (TM12) or substituted for the entire first transmembrane domain of HBsAg (TM16). Substitution for approximately half of the first transmembrane domain of HBsAg (TM14) did not result in detectable MPR expression.
Figure 4:
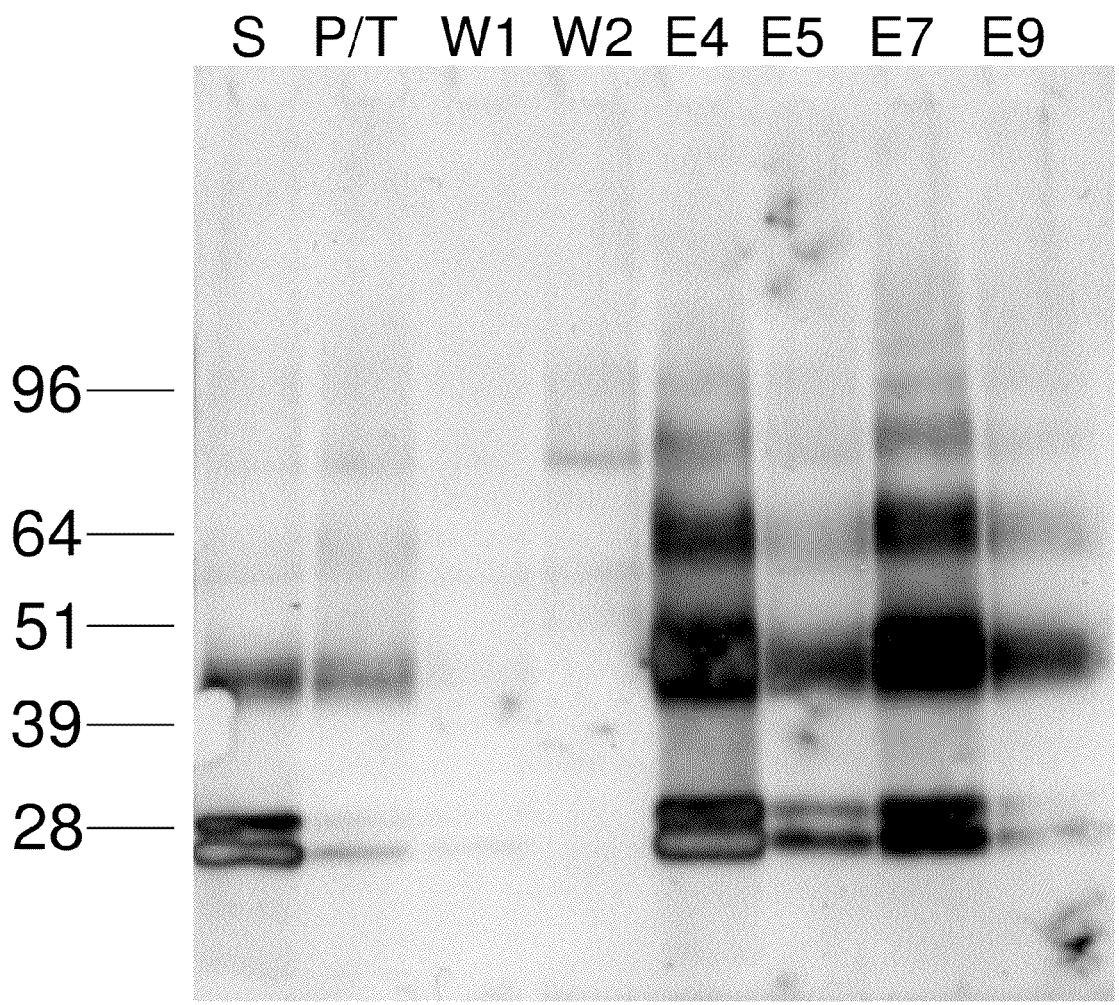
FIG. 4 is a digital image of a gel showing purification of MPR particles by hydrophobic interaction chromatography.
Figure 5:
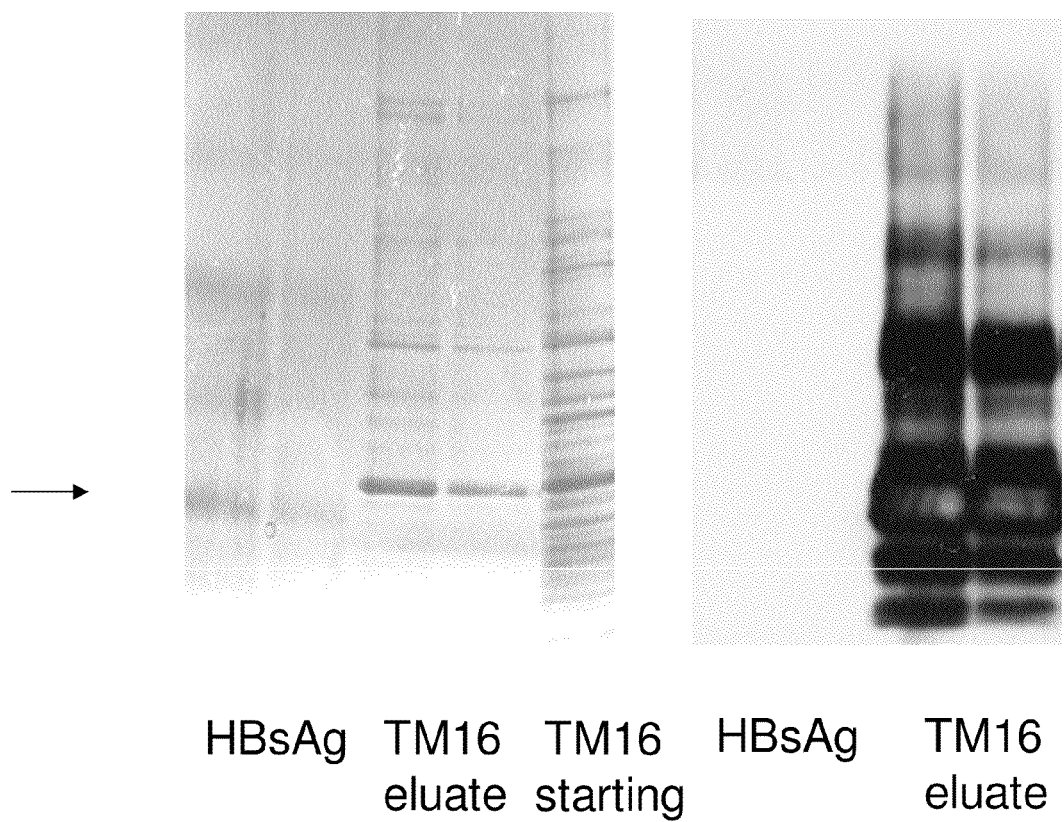
FIG. 5 is a pair of digital images of gels illustrating the purity of HBsAg when a gp41 membrane spanning domain is substituted for the first transmembrane domain of HBsAg (TM16).

In one example, a variant HBsAg construct (TM16) was prepared by substituting the membrane spanning domain of gp41 for the entire first membrane spanning domain of HBsAg (see FIG. 2A). This construct was predicted to anchor the MPR in the lipid membrane so that it would be oriented in a manner similar to its native orientation in gp41. Studies were then performed to determine if MPR particles could be expressed with different gp41 sequences substituted for the first membrane spanning domain of HBsAg. FIG. 3A provides a schematic illustrating the insertion of various gp41 membrane spanning domains into the first membrane spanning domain of HBsAg. FIG. 3B is a digital image of a gel illustrating MPR expression in HBsAg when gp41 is substituted for the beginning of the first transmembrane domain of HBsAg (TM12) or substituted for the entire first transmembrane domain of HBsAg (TM16). However, substitution for approximately half of the first transmembrane domain of HBsAg (TM14) did not result in detectable MPR expression. Studies were then performed to determine the purity of TM16 (see FIG. 5) and if TM16 could form virus-like particles (see FIG. 6). TM16 was purified by sedimentation in sucrose gradients, followed by hydrophobic interaction chromatography, and the product was examined by electron microscopy (FIG. 6). TM16 particles are polymorphic in size, with a range 30+/−3 nm. This is similar to the size and heterogeneity of native HBsAg particles. Alternatively, TM16 was purified by banding in CsCl density gradients, and this also demonstrated particles.

The HBsAg variant TM20 was generated in which the third transmembrane domain of HBsAg was substituted with a gp41 membrane spanning domain. The entire gene for the TM20 construct was synthesized and then inserted into pFastbac cloning vector (commercially available from Invitrogen). Cells containing the complete baculovirus genome as a "bacmid" were transfected and the TM20 coding sequence entering the bacmid via a transposon. Bacmid DNA was then transfected into Sf9 cells, resulting in the production of baculovirus expressing the TM20 gene. Cell pellets were screened for protein expression by Western blot analysis. The high expressing baculovirus was grown to 200 ml stock and titered for PFU/ml. To express the protein, two to four large flasks of Hi 5 insect cells (200 ml each) were grown, at $1.5 \times 10^6$/ml, and infect them at an moi of 4:1. The cells were then incubated at 27° C. on a shaker, and harvested at 28 to 30 hours. The cells were spun down, and the virus-like particles remained in the cells. The pellet from each flask was frozen in 10 ml phosphate buffered saline (PBS). The cells were lysed by freezing and thawed followed by sonication for 1 min. The lysate (10 to 20 ml) was layered onto a step gradient consisting of 10, 20 and 50% sucrose. Sedimentation was for 2 hrs and 20 min at 27,000 rpm in a Beckman SW28 rotor.

Fractions (0.5 ml each) were dripped from the bottom, and each fraction was assayed for antigen content by ELISA. Active fractions were pooled, and the sample was stored frozen at −80° C. Further purification is done by hydrophobic interaction chromatography. Briefly, 20 ml of pooled sucrose fractions were diluted to 30 ml with PBS, and ammonium sulfate was added to make 0.7 M. Triton X100 was added to 0.025%, close to the CMC. The sample was passed twice through a 4 to 5 ml column of Macro-Prep Methyl HIC support from Bio-Rad. Pass through fractions were collected, followed by three wash fractions of one column volume each. Elution was performed in 2× PBS, and 8 fractions of 0.5 column volume were collected. Each fraction is assayed by ELISA, and the peak elution usually occurred in the second elution fraction. Antigen content was determined by Western blot. Antigen quantity was then determined by comparing antigen test sample to a known standard or by use of a digital reader based on fluorescence.

TM20 particles were banded in CsCl and examined by electron microscopy. The particles were somewhat larger than TM16 particles, with a diameter of 45+/−5 nm (FIG. 6). Size exclusion chromatography and cesium chloride gradient studies (FIG. 7) demonstrated that TM20 particles assembled correctly (e.g., similar to native HBsAgs) despite replacing the third transmembrane domain of HBsAg with a gp41 antigenic insert (such as the antigenic insert provided in FIG. 10).

Figure 9B:
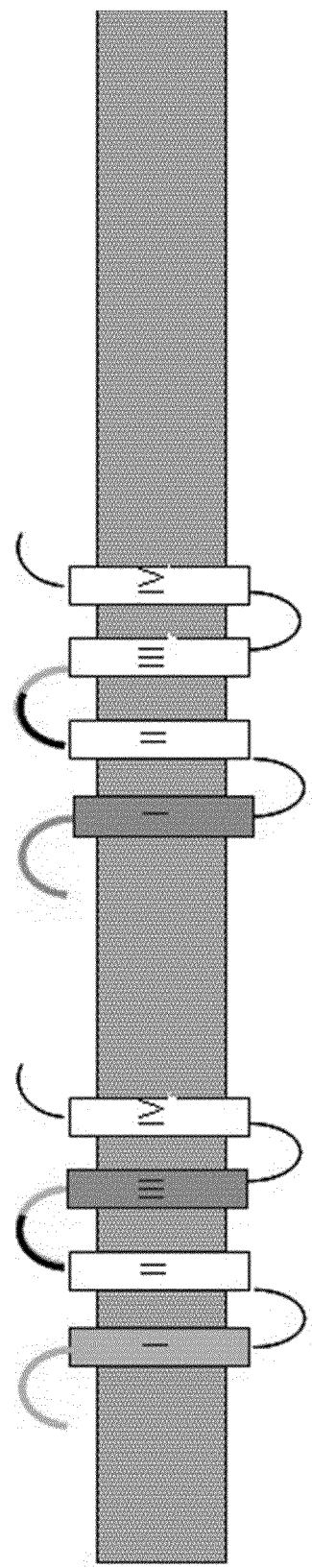
FIG. 9B is a pair of schematics illustrating additional exemplary variant HBsAg constructs that assemble particles.

FIG. 8 illustrates purification of an additional variant HBsAg (MPRS) by a methyl HIC column in which the variant HBsAg includes a gp41 insert following the fourth domain of the HBsAg. The following additional variant HBsAgs were constructed and determined to be form virus-like particles: TM34, TM32F, TM16+20 and TM16+34 (see FIGS. 9A and 9B). TM32F HBsAg variant includes four MPRs in a row in the middle loop of HBsAg (FIG. 9B). TM16+20 HBsAg variant has a gp41 spanning membrane domain in the first and third domain and two MPRs. TM16+34 has a MPR anchored to a gp41 spanning membrane domain in the first domain of HBsAg and a MPR in the middle loop of HBsAg (in between the second and third domain of HBsAg), as illustrated in FIG. 9B. The constructs with two MPRs were determined to be more antigenic than any of tested single constructs.

These studies demonstrate that HBsAg particles allow various substitutions within HBsAgs, such as within HBsAg membrane spanning domains while still forming antigenic particles.

Figure 11:
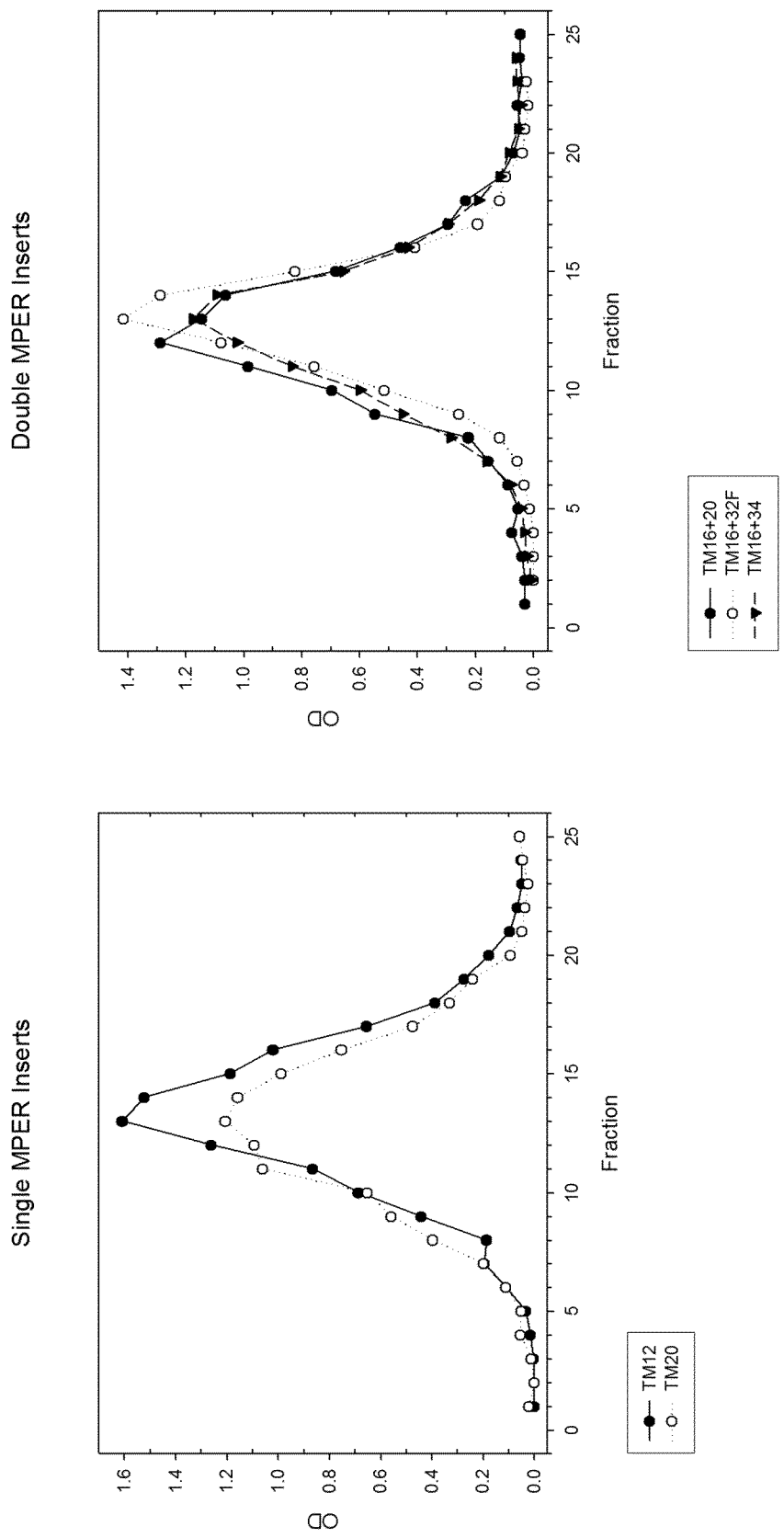
FIG. 11 is a pair of graphs illustrating the size and expression of HBsAg constructs with either single or double inserts as tested by sedimentation in sucrose gradients.

Expression of the three HBsAg hybrids with a MPR linked to the amino end was tested by western blot (FIG. 3B), for two DNA constructs of each type. TM12 was expressed well, while TM14 was not expressed at all. In contrast, TM16 was expressed as well as TM12, even though the entire first membrane spanning domain of HBsAg was replaced by the transmembrane domain of gp41. A strong band on western blot generally indicates particle assembly, since unassembled HBsAg is quickly degraded. To evaluate this, each particle was sedimented in sucrose gradients and the peaks were detected with a monoclonal antibody to the MPR. As shown in FIG. 11 (left panel), TM12 and TM16 sedimented at large size, comparable to native HBsAg particles. These results indicate that HBsAg particles could assemble normally, even when the entire first membrane spanning domain was replaced by another transmembrane sequence.

The size and expression of HBsAg hybrids with a MPR linked to the exposed middle domain was tested by sedimentation in sucrose gradients (FIG. 11, right panel). These particles, TM32, TM34, and TM32F, sedimented at large size, similar to native HBsAg. This indicates that the MPR determinant could be expressed close to the major antigenic determinant of HBsAg, without disrupting particle formation. Extension of TM34 to include the entire third membrane spanning domain produced TM20. This construct also formed particles, as shown by sedimentation at large size (FIG. 11, right side).

Figure 12:
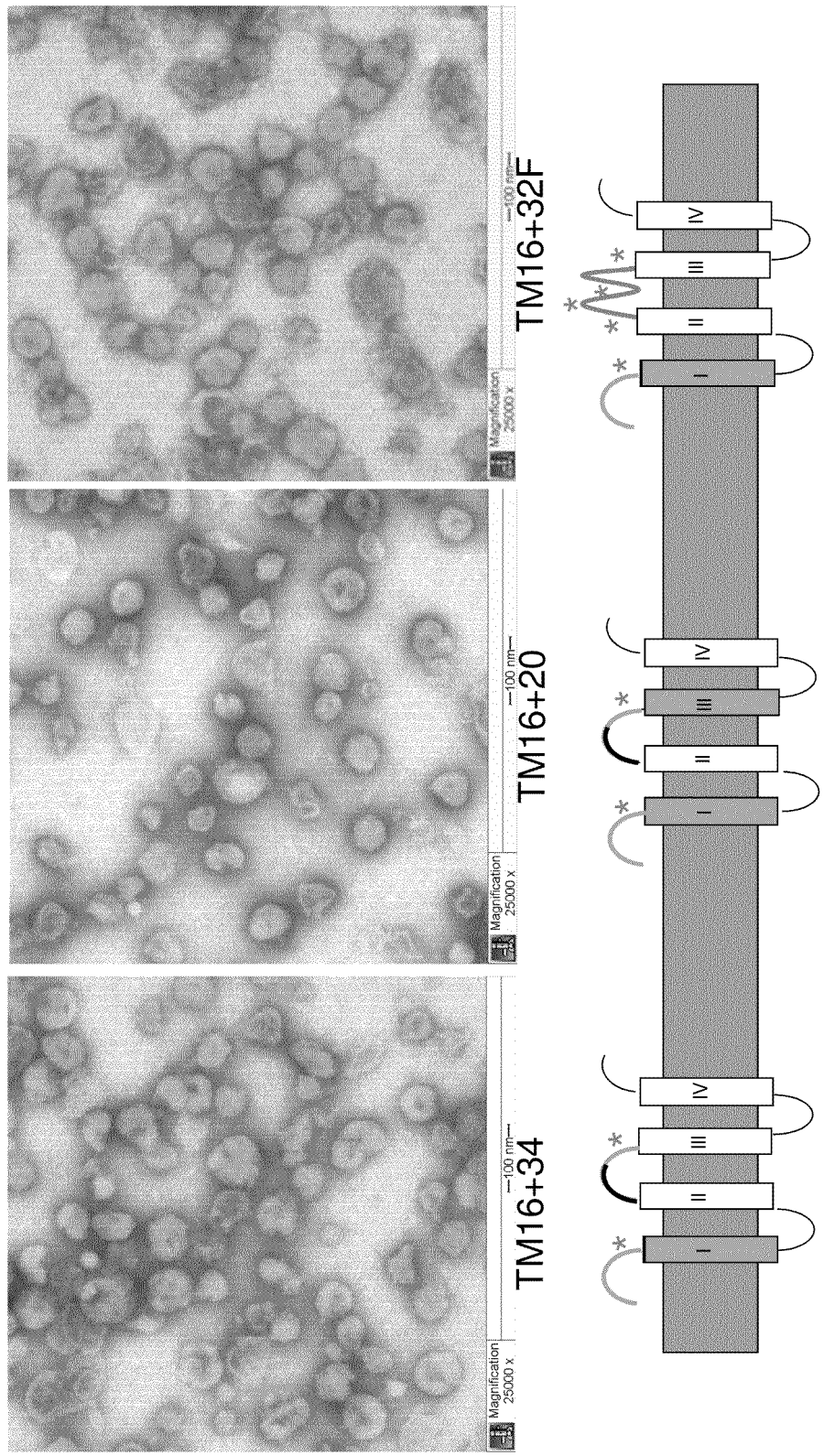
FIG. 12 is a series of digital images illustrating successful particle formation of variant HBsAgs in which two domains with the HBsAg are substituted (each specific construct is illustrated by a schematic below each representative image).

Next, the ability to form particles when two MPR substitutions in the same construct was tested. Two of these, TM16+32F and TM16+34, combined a substitution at the first membrane spanning domain with one in the exposed middle loop (FIG. 9B). This left three membrane spanning domains of HBsAg, and they all formed particles, as shown by sedimentation at large size in sucrose gradients. After purification by banding in CsCl, these particles were significantly larger by EM than native HBsAg particles, with diameters ranging from 54+/−8 nm for TM16+32F to 55+/−7 nm for TM16+34 (FIG. 12).

The construct most challenging for particle formation combined TM16 and TM20 in the same hybrid protein, called TM16+20. Despite the absence of the first and third membrane spanning domains of HBsAg, this construct sedimented at large size and formed particles, as shown by electron microscopy (FIG. 12). The two remaining HBsAg domains (domains 2 and 4) were sufficient for particle formation, and this was not blocked by two copies of the transmembrane domain of gp41. After banding in CsCl, TM16+20 particles were studied by electron microscopy; they gave large particles, with a diameter of 52+/−8 nm (FIG. 12).

The HBsAg variant particles allowed the immunological properties of the MPR determinant to function when displayed on a lipid surface to be evaluated. By comparing antibody binding to homologous constructs, the effect of MPR valency on antigenicity and immunogenicity were determined. For example, the initial constructs, such as TM12, TM16, TM20, and TM34, were monovalent in MPR, but the combined constructs, TM16+20 and TM16+34, were divalent in MPR, and TM16+32F was pentavalent.

Figure 13:
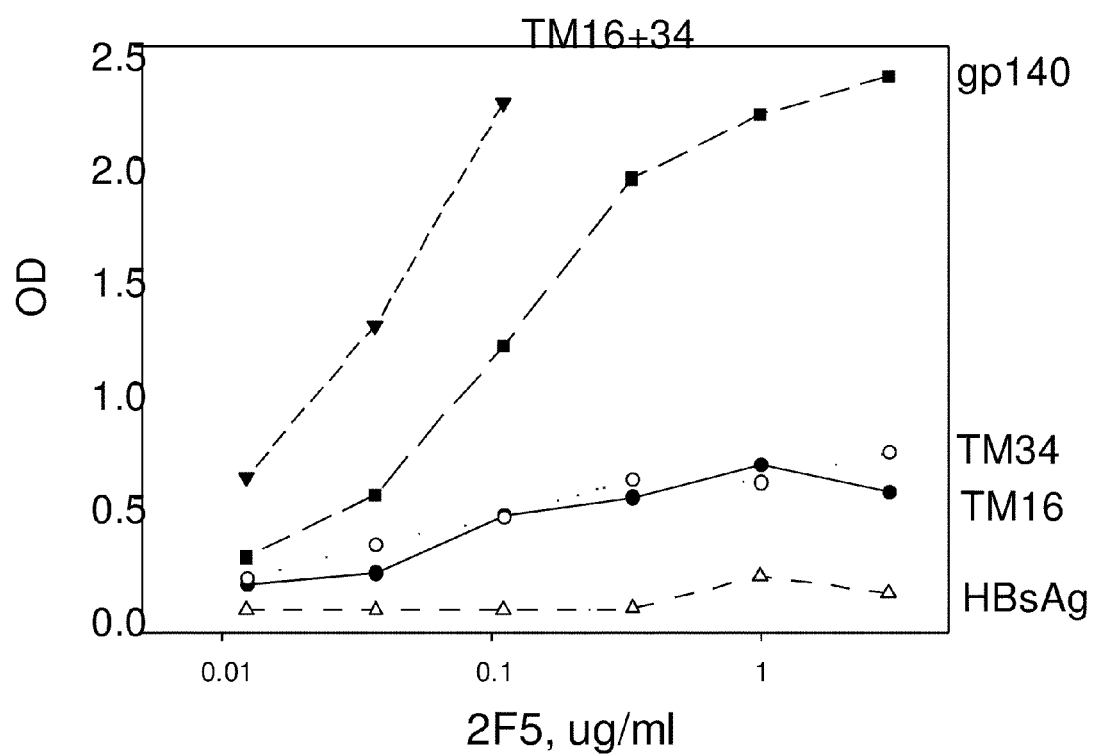
FIG. 13 is a graph illustrating antigenicity of various disclosed variant HBsAg constructs is dependent upon the valency of the constructs wherein divalent insertion of MPR determinants into TM16+31/34 had a synergistic effect on antibody binding.

Two monovalent MPR particles, TM16 and TM34, were combined to produce divalent TM16+34 particles. The binding of monoclonal 2F5 to the divalent construct was compared to the monovalent parent constructs TM16 and 34 or to a negative control of HBsAg (FIG. 13). Divalent insertion of MPR determinants into TM16+34 had a synergistic effect on antibody binding: it was drastically greater than to the monovalent parental forms, and it was greater than the sum of the monovalent antigens. It was also greater than binding to a recombinant gp140 control. These results suggest cooperative binding of 2F5 to divalent MPR antigens, possibly by allowing both arms of the antibody to bind the same antigen.

Two additional MPR constructs, monovalent TM16 and MPR tetravalent TM32F, were combined to form the pentavalent construct, called TM16+32F. As before, antibody binding to the pentavalent MPR was greater than either of the parental forms or to the HBsAg negative control (FIG. 13). It was also greater than the sum of the parental forms. These results suggest cooperative binding of divalent antibodies to multivalent MPR particles.

To determine the immunogenicity of the disclosed constructs, pairs of rabbits were immunized with each of the multivalent particles (FIG. 14). The resulting antibodies were titered on ELISA plates coated with AT-2 inactivated virions of the MN strain (FIG. 14, left panel). TM16+32F was more immunogenic than any other construct and 2/2 rabbits (B9 and B10) gave antibodies to MPR after the second dose. These antibodies were specific for viral antigens, since there was no binding to a microvessicle control. The greater immunogenicity of the TM16+32F construct may be due to its greater valency, five versus two for the others. AT-2 inactivated virions were employed in the ELISA assay because it contains native MPR antigen on a viral surface.

The rabbit sera were tested for cross reactivity on other HIV strains (aldrithiol-2 inactivated), or on a microvessicle control (FIG. 14, right panel). Strain 89.6 was the immunizing strain, but rabbit B9 showed better cross reactive binding on all other strains tested. Its cross reactivity was comparable to that of monoclonal 2F5. In contrast, rabbit B 10, with a lower antibody titer after two doses of antigen, bound only to the MN strain. Monoclonal 2F5 also bound MN better than the other strains, suggesting that MN virions may expose MPR better than the other strains. Pentavalent TM16+32F particles can elicit antibodies to a membrane proximal region determinant that is shared among a variety of HIV isolates.

Therefore, these studies demonstrate that the transmembrane domain of gp41 could be substituted for the entire first membrane spanning domain of HBsAg, while producing a hybrid protein that still formed particles. Particles could also be formed when the transmembrane domain of gp41 was swapped for the third membrane spanning domain of HBsAg, and when it was substituted for both the first and third domains in the same construct. These particles demonstrated the plasticity and tenacity of particle formation by HBsAg. They also displayed the MPR determinant of HIV in a way that closely resembles its natural form on the surface of virions. These determinants were displayed on a lipid surface, where they are anchored via their own transmembrane domain. They elicited antibodies capable of binding HIV virions in a broadly crossreactive pattern. As such, these studies suggest that immunizing with a MPR determinant that mimics its natural form on the surface of virions can elicit antibodies that bind this potent and cross reactive neutralizing determinant on the virus.

It is believed that these particles express neutralizing determinants of gp41 in a more exposed form, thereby providing support for use of these particles to produce new vaccine antigens with the potential to improve the quantity and quality of the antibody response to HIV proteins.

Example 2

Treatment of HIV in a Human Subject

This example describes a particular method that can be used to treat HIV in a human subject by administration of one or more compositions that includes an effective amount of any of the disclosed isolated immunogens. Although particular methods, dosages, and modes of administrations are provided, one skilled in the art will appreciate that variations can be made without substantially affecting the treatment.

Based upon the teaching disclosed herein, HIV, such as HIV type 1, can be treated by administering a therapeutically effective amount of a composition that includes variant HBsAgs to reduce or eliminate HIV infection, replication or a combination thereof. The method can include screening subjects to determine if they have HIV, such as HIV-1. Subjects having HIV are selected. In one example, subjects having increased levels of HIV antibodies in their blood (as detected with an enzyme-linked immunosorbent assay, Western blot, immunofluorescence assay, or nucleic acid testing, including viral RNA or proviral DNA amplification methods are selected. In one example, a clinical trial would include half of the subjects following the established protocol for treatment of HIV (such as a highly active antiretroviral therapy). The other half would follow the established protocol for treatment of HIV (such as treatment with highly active antiretroviral compounds) in combination with administration of the compositions including variant HBsAgs (as described above). In another example, a clinical trial would include half of the subjects following the established protocol for treatment of HIV (such as a highly active antiretroviral therapy). The other half would receive a composition including variant HBsAgs (such as virus-like particles including any of the disclosed variant HBsAgs, such as variant HBsAg TM16, variant HBsAg TM20, variant HBsAg MPRS, variant DA31-34, variant DA31-32F, variant TM16+20, variant TM16+31/34 or any combination thereof).

Screening Subjects

In particular examples, the subject is first screened to determine if they have HIV. Examples of methods that can be used to screen for HIV include a combination of measuring a subject's CD4+ T cell count and the level of HIV in serum blood levels.

In some examples, HIV testing consists of initial screening with an enzyme-linked immunosorbent assay (ELISA) to detect antibodies to HIV, such as to HIV-1. Specimens with a nonreactive result from the initial ELISA are considered HIV-negative unless new exposure to an infected partner or partner of unknown HIV status has occurred. Specimens with a reactive ELISA result are retested in duplicate. If the result of either duplicate test is reactive, the specimen is reported as repeatedly reactive and undergoes confirmatory testing with a more specific supplemental test (e.g., Western blot or an immunofluorescence assay (IFA)). Specimens that are repeatedly reactive by ELISA and positive by IFA or reactive by Western blot are considered HIV-positive and indicative of HIV infection. Specimens that are repeatedly ELISA-reactive and occasionally provide an indeterminate Western blot result, which may be either an incomplete antibody response to HIV in an infected subject, or nonspecific reactions in an uninfected subject. IFA can be used to confirm infection in these ambiguous cases. In some instances, a second specimen will be collected more than a month later and retested for subjects with indeterminate Western blot results. In additional examples, nucleic acid testing (e.g., viral RNA or proviral DNA amplification method) can also help diagnosis in certain situations.

The detection of HIV in a subject's blood is indicative that the subject has HIV and is a candidate for receiving the therapeutic compositions disclosed herein. Moreover, detection of a CD4+ T cell count below 350 per microliter, such as 200 cells per microliter, is also indicative that the subject is likely to have HIV.

Pre-screening is not required prior to administration of the therapeutic compositions disclosed herein.

Pre-Treatment of Subjects

In particular examples, the subject is treated prior to administration of a therapeutic composition that includes one or more of the disclosed variant HBsAgs. However, such pre-treatment is not always required, and can be determined by a skilled clinician. For example, the subject can be treated with an established protocol for treatment of HIV (such as a highly active antiretroviral therapy).

Administration of Therapeutic Compositions

Following subject selection, a therapeutic effective dose of the composition including variant HBsAgs is administered to the subject (such as an adult human or a newborn infant either at risk for contracting HIV or known to be infected with HIV). For example, a therapeutic effective dose of a composition including one or more of the HBsAg variants is administered to the subject to in an amount sufficient to raise an immune response to HIV. Administration induces a sufficient immune response to reduce viral load, to prevent or lessen a later infection with the virus, or to reduce a sign or a symptom of HIV infection. Additional agents, such as anti-viral agents, can also be administered to the subject simultaneously or prior to or following administration of the disclosed compositions. Administration can be achieved by any method known in the art, such as oral administration, inhalation, intravenous, intramuscular, intraperitoneal, or subcutaneous.

In some particular examples, the composition includes variant HBsAgs with one or more transmembrane domains of the HBsAg replaced with a gp41 antigenic insert. The gp41 antigenic insert includes (a) an antigenic polypeptide fragment of gp41, such as an antigenic polypeptide gp41 fragment with the amino acid sequence of SEQ ID NO: 1, and (b) a transmembrane domain of gp41, such as a transmembrane spanning gp41 region with the amino acid sequence set forth in SEQ ID NO: 25 (in which wherein $X_1$, $X_2$, $X_3$ and $X_4$ are any amino acid $X_5$, $X_6$, and $X_7$ are any hydrophobic amino acid). In one example, the antigenic polypeptide fragment of gp41 is between 28 and 150 amino acids in length and the membrane spanning region of gp41 is between 22 and 40 amino acids in length.

In one particular example, the composition includes a variant HBsAg in which the first transmembrane spanning domain of the HBsAg is replaced by a gp41 antigenic insert. For example, the gp41 antigenic insert replaces amino acid residues 1-35 of SEQ ID NO: 31. In another example, the gp41 antigenic insert replaces amino acid residues 1-32 of SEQ ID NO: 31. In yet another example, the gp41 antigenic insert replaces amino acid residues 1-29 of SEQ ID NO: 31. In further examples, the composition includes a variant HBsAg in which the first transmembrane spanning domain of the HBsAg is replaced by a gp41 antigenic insert and the variant HBsAg has the amino acid sequence set forth as SEQ ID NO: 29.

In another particular example, the composition includes includes a variant HBsAg in which the third transmembrane spanning domain of the HBsAg is replaced by a gp41 antigenic insert. For example, the gp41 antigenic insert replaces amino acid residues 150-190 of SEQ ID NO: 31. In another example, the gp41 antigenic insert replaces amino acid residues 153-187 of SEQ ID NO: 31. In yet another example, the gp41 antigenic insert replaces amino acid residues 156-185 of SEQ ID NO: 31. In a further example, the composition includes a variant HBsAg in which the third transmembrane spanning domain of the HBsAg is replaced by a gp41 antigenic insert and the variant HBsAg has the amino acid sequence set forth as SEQ ID NO: 57.

In an even more particular example, the composition includes a variant HBsAg in which the first and the third transmembrane spanning domains of the HBsAg are replaced by a gp41 antigenic insert. For example, the gp41 antigenic insert replaces amino acid residues 1-35 and 150-190 of SEQ ID NO: 31. In another example, the gp41 antigenic insert replaces amino acid residues 1-32 and 153-187 of SEQ ID NO: 31. In yet another example, the gp41 antigenic insert replaces amino acid residues 1-29 and 156-185 of SEQ ID NO: 31. In a particular example, the the composition includes a variant HBsAg in which the third transmembrane spanning domain of the HBsAg is replaced by a gp41 antigenic insert and the variant HBsAg has the amino acid sequence set forth as SEQ ID NO: 58.

In additional examples, the composition includes variant HBsAgs with a gp41 transmembrane spanning domain inserted into the first domain and third domain of the HBsAgs. In another example, the composition includes variant HBsAgs with at least one MPR inserted into the HBsAg in between the second domain and third domain. In additional examples, the composition includes a combination of the disclosed variant HBsAgs, such as variant HBsAgs with a gp41 antigenic insert (including a gp41 transmembrane domain and MPR) replacing the first and third domain of the HBsAg (variant HBsAg TM16+TM20) and variant HBsAgs with a gp41 antigenic insert (a gp41 transmembrane domain and MPR) replacing the first domain of the HBsAg and a MPR in between the second and third transmembrane domains (TM16+34). In other examples, the composition includes isolated nucleic acid molecules encoding the variant HBsAgs or viral-like particles including the varianat HBsAgs. In particular examples, the composition includes variant HBsAgs with an amino acid sequence set forth by SEQ ID NOs: 56 and 62-64.

The amount of the composition administered to prevent, reduce, inhibit, and/or treat HIV or a condition associated with it depends on the subject being treated, the severity of the disorder, and the manner of administration of the therapeutic composition. Ideally, a therapeutically effective amount of an agent is the amount sufficient to prevent, reduce, and/or inhibit, and/or treat the condition (e.g., HIV) in a subject without causing a substantial cytotoxic effect in the subject. An effective amount can be readily determined by one skilled in the art, for example using routine trials establishing dose response curves. In addition, particular exemplary dosages are provided above. The therapeutic compositions can be administered in a single dose delivery, via continuous delivery over an extended time period, in a repeated administration protocol (for example, by a daily, weekly, or monthly repeated administration protocol). In one example, therapeutic compositions that include variant HBsAgs are administered intravenously to a human. As such, these compositions may be formulated with an inert diluent or with an pharmaceutically acceptable carrier.

In one specific example, a composition including variant HBsAgs is administered intravenously from 0.1 pg to about 100 mg per kg per day. In an example, the composition is administered continuously. In another example, the composition is administered at 50 μg per kg given twice a week for 2 to 3 weeks. Administration of the therapeutic compositions can be taken long term (for example over a period of months or years).

Assessment

Following the administration of one or more therapies, subjects having HIV (for example, HIV-1 or HIV-2) can be monitored for reductions in HIV levels, increases in a subjects CD4+ T cell count, or reductions in one or more clinical symptoms associated with HIV. In particular examples, subjects are analyzed one or more times, starting 7 days following treatment. Subjects can be monitored using any method known in the art. For example, biological samples from the subject, including blood, can be obtained and alterations in HIV or CD4+ T cell levels evaluated.

Additional Treatments

In particular examples, if subjects are stable or have a minor, mixed or partial response to treatment, they can be re-treated after re-evaluation with the same schedule and preparation of agents that they previously received for the desired amount of time, including the duration of a subject's lifetime. A partial response is a reduction, such as at least a 10%, at least 20%, at least 30%, at least 40%, at least 50%, or at least 70% in HIV infection, HIV replication or combination thereof. A partial response may also be an increase in CD4+ T cell count such as at least 350 T cells per microliter.

Example 3

Method of Monitoring Serum Antibodies to HIV

This example illustrates the methods of monitoring serum antibodies to HIV.

Based upon the teachings disclosed herein, the presence of serum antibodies to HIV can be monitored using the isolated immunogens disclosed herein, such as to detect an HIV infection. Generally, the method includes contacting a sample from a subject, such as, but not limited to a blood, serum, plama, urine or sputum sample from the subject with one or more of the variant HBsAgs disclosed herein (or a polymeric form thereof) and detecting binding of antibodies in the sample to the variant HBsAgs. The binding can be detected by any means known to one of skill in the art, including the use of labeled secondary antibodies that specifically bind the antibodies from the sample. Labels include radiolabels, enzymatic labels, and fluorescent labels.

The results can be used to distinguish a subpopulation of patients that make MPER antibodies in response to infection. This population may have a different clinical outcome, based on production of MPER-specific antibodies. They can also be used to detect a patient's immune response to another vaccine antigen that elicits antibodies specific for the MPER determinant. The high responder patients detected in this way may be the ones protected against HIV infection.

Example 4

Screening of Test Agents to Treat HIV

This example describes methods that can be used to identify agents to treat HIV.

According to the teachings herein, one or more agents for treating HIV, such as HIV-1, can be identified by contacting a cell, such as a cell expressing a variant HBsAg, with one or more test agents under conditions sufficient for the one or more test agents to alter the activity of the variant HBsAg. The method can include detecting alterations in HIV or CD4+ T cell levels. Various types of in vitro assays may be employed to identify agents to treat HIV including, but not limited to, HIV-infection assays, LFA-activity assays, binding assays, standard Western blot or immunoassay techniques and other well known assays to those of skill in the art. However, the disclosure is not limited to particular methods of detection.

Regardless of the assay technique, agents that cause at least a 2-fold decrease, such as a 3-fold decrease, a 4-fold decrease, or 5-fold decrease in detectable HIV or at least a 2-fold increase, such as a 3-fold increase, a 4-fold increase, or 5-fold increase in CD4+ T cell levels, are selected for further evaluation.

Potential therapeutic agents identified with these or other approaches, including the specific assays and screening systems described herein, are used as lead compounds to identify other agents having even greater modulatory effects on HIV. Candidate agents also can be tested in additional cell lines and animal models of HIV to determine their therapeutic value. The agents also can be tested for safety in animals, and then used for clinical trials in animals or humans. In one example, genetically engineered mouse models of HIV are employed to determine therapeutic value of test agents. In another example, simian immunodeficiency virus (SIV)-macaque or a chimeric simian-human immunodeficiency virus (SHIV)-macaque model are utilized. SHIV strains have the viral envelope of HIV but the gag/pol genes of SIV. Pathogenesis is similar with respect to macrophage and T lymphocyte cell tropism, histopathologic changes, CD4-cell depletion and clinical signs of AIDS in virulent strains. For example, a monkey is immunized with neutralizing antibodies and then challenged with a SHIV strain that is the same as that used to vaccinate the animal. In another example, a monkey immunized with neutralizing antibodies and then challenged with a SHIV strain that is different from the strain used to vaccinate the animal. Such studies could be used to identify agents that would protect subjects, such as humans, from HIV or reduce one or more symptoms associated with HIV.

The results can be used to distinguish a subpopulation of patients that make MPER antibodies in response to infection. This population may have a different clinical outcome, based on production of MPER-specific antibodies. They can also be used to detect a patient's immune response to another vaccine antigen that elicits antibodies specific for the MPER determinant. The high responder patients detected in this way may be the ones protected against HIV infection.

Example 5

Binding of HIVIgG and Human Sera from HIV-1 Positive Patients to Disclosed Variant HBsAg and Variant HBsAg Particles Based upon the teaching herein, the utility of variant HBsAg particles to identify sera that contain neutralizing antibodies against MPR can be determined by screening a set of weakly and broadly neutralizing human HIV-1 positive sera and HIV-IgG for binding to variant HBsAg particles. Human sera from HIV-1 positive patients and antibody 2F5 can be serially diluted and analyzed for binding to variant HBsAg and variant HBsAg particles in ELISA format. The results can be used to distinguish a subpopulation of patients that make MPER antibodies in response to infection. This population may have a different clinical outcome, based on production of MPER-specific antibodies. They can also be used to detect a patient's immune response to another vaccine antigen that elicits antibodies specific for the MPER determinant. The high responder patients detected in this way may be the ones protected against HIV infection.

Example 6

Immunization of Rabbits with Variant HBsAg Particles

Based upon the teaching herein, rabbits are immunized with 5, 20, 50 and 100 µg of the disclosed variant HBsAg particles in ALUM and CpG as adjuvant by intramuscular route. The rabbit sera is analyzed for binding to HBsAg and 2F5 epitope-containing peptide by ELISA. In addition, the sera can be checked for their neutralizing ability in a viral neutralization assay using sensitive HIV-1 strains and chimeric HIV-2 strains containing HIV-1 2F5 epitope. If the rabbits are immunized to variant HBsAg particles, then a high titer of antibodies will be raised to HBsAg and a 2F5 epitope.

TABLE 1

Various Oligonucleotide Primers

| Primer Name | Primer Sequence |
|---|---|
| SAg-Forward | 5' GGAGCTCGTCGA CAGCAA 3' (SEQ ID NO: 38) |
| SAg-Reverse | 5' GC TCT AGA CCC GA T GTA CAC CCA 3' (SEQ ID NO: 39) |
| MPR Forward | 5' GC TCT AGA AAC GAG CAG GAG CTG CTG 3' (SEQ ID NO: 40) |
| MPR Reverse | 5' CGC GGA TCC TCA CCC CTT GAT GTA CCA CAG CCA CTT 3' (SEQ ID NO: 41) |
| MPR-Foldon Rev | 5' CGC GGA TCC TCA ATG GTG ATG GTG ATG GTG GGG 3' (SEQ ID NO: 42) |
| C-heptad-MPR Forward | 5' GC TCT AGA GCC GTG GAG CGG TAC CTG 3' (SEQ ID NO: 43) |
| MPR-Tm5 Reverse | 5' CTCGGATCCTCAAATCATGATGAAAATCTTGAT 3' (SEQ ID NO: 44) |
| MPR-Tm10 Reverse | 5' CTCGGATCCTCACACCAGGCCACCAACAAT 3' (SEQ ID NO: 45) |
| MPR-Tm15 Reverse | 5' CTCGGATCCTCACACCAGCCTCAGGCCCAC 3' (SEQ ID NO: 46) |
| MPR-Tm23-C9 Reverse | 5' CTCGGATCCTCAGGCGGGCGC 3' (SEQ ID NO: 47) |
| AgeI Forward | 5' CCCTGCAAGACCTGCACC ACCACCGGTCAGGGCAACTCCAAGTTCCCC 3' (SEQ ID NO: 48) |
| AgeI reverse | 5' GGGGAACTTG GAGTTGCCCT GACCGGTGGT GGTGCAGGTC TTGCAGGG 3' (SEQ ID NO: 49) |
| MPR AgeI Forward | 5' GGC ACC GGT AAC GAG CAG GAG CTG CTG 3' (SEQ ID NO: 50) |
| MPR AgeI Reverse | 5' GGC ACC GGT CCC CTT GAT GTA CCA CAG CCA CTT 3' (SEQ ID NO: 51) |

TABLE 1-continued

Various Oligonucleotide Primers

| Primer Name | Primer Sequence |
|---|---|
| MPRSAG Forward | 5' AGC GAA TTC AAC GAG CAG GAG CTG CTG 3' (SEQ ID NO: 52) |
| MPR SAG Reverse | 5' CGC GGA TCC TCA CCC GA T GTA CAC-CCA 3' (SEQ ID NO: 53) |
| SAGMPR RI forward | 5' CAG GAA GCC GGA GGT GATGAA CCC CTT GAT GTA CCA CAG CCA CTT 3' (SEQ ID NO: 54) |
| SAG MPR RI Reverse | 5' AAG TGG CTG TGG TAC ATC AAG GGG TTC ATC ACC TCC GGC TTC CTG 3' (SEQ ID NO: 55) |

In view of the many possible embodiments to which the principles of the disclosed invention may be applied, it should be recognized that the illustrated embodiments are only examples of the invention and should not be taken as limiting the scope of the invention. Rather, the scope of the invention is defined by the following claims. We therefore claim as my invention all that comes within the scope and spirit of these claims.

I claim:

1. A viral-like particle comprising an isolated immunogen comprising the amino acid sequence set forth as SEQ ID NO: 29.

2. The viral-like particle of claim 1, further comprising at least one TLR ligand.

3. A composition comprising the viral-like particle of claim 1.

4. The composition of claim 3, further comprising an adjuvant.

5. A viral-like particle comprising an isolated immunogen of comprising the amino acid sequence set forth as SEQ ID NO: 57.

6. The viral-like particle of claim 5, further comprising at least one TLR ligand.

7. A composition comprising the viral-like particle of claim 5.

8. The composition of claim 7, further comprising an adjuvant.

9. A viral-like particle comprising an isolated immunogen of comprising the amino acid sequence set forth as SEQ ID NO: 58.

10. The viral-like particle of claim 9, further comprising at least one TLR ligand.

11. A composition comprising the viral-like particle of claim 9.

12. The composition of claim 11, further comprising an adjuvant.

* * * * *

SEQUENCE LISTING

```
<160> NUMBER OF SEQ ID NOS: 64

<210> SEQ ID NO 1
<211> LENGTH: 28
<212> TYPE: PRT
<213> ORGANISM: Artificial Sequence
<220> FEATURE:
<223> OTHER INFORMATION: Recombinantly produced peptide
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid

<400> SEQUENCE: 1

Asn Glu Xaa Xaa Leu Leu Xaa Leu Asp Lys Trp Ala Ser Leu Trp Asn
1               5                   10                  15

Trp Phe Asp Ile Thr Asn Trp Leu Trp Tyr Ile Xaa
            20                  25

<210> SEQ ID NO 2
<211> LENGTH: 28
<212> TYPE: PRT
<213> ORGANISM: Artificial Sequence
<220> FEATURE:
<223> OTHER INFORMATION: Recombinantly produced peptide

<400> SEQUENCE: 2

Asn Glu Gln Glu Leu Leu Ala Leu Asp Lys Trp Ala Ser Leu Trp Asn
1               5                   10                  15

Trp Phe Asp Ile Thr Asn Trp Leu Trp Tyr Ile Lys
            20                  25

<210> SEQ ID NO 3
<211> LENGTH: 28
<212> TYPE: PRT
<213> ORGANISM: Artificial Sequence
<220> FEATURE:
<223> OTHER INFORMATION: Recombinantly produced peptide

<400> SEQUENCE: 3
```

```
Asn Glu Gln Asp Leu Leu Ala Leu Asp Lys Trp Ala Ser Leu Trp Asn
1               5                   10                  15

Trp Phe Asp Ile Thr Asn Trp Leu Trp Tyr Ile Lys
            20                  25
```

<210> SEQ ID NO 4
<211> LENGTH: 28
<212> TYPE: PRT
<213> ORGANISM: Artificial Sequence
<220> FEATURE:
<223> OTHER INFORMATION: Recombinantly produced peptide

<400> SEQUENCE: 4

```
Asn Glu Gln Asp Leu Leu Ala Leu Asp Lys Trp Ala Asn Leu Trp Asn
1               5                   10                  15

Trp Phe Asp Ile Ser Asn Trp Leu Trp Tyr Ile Lys
            20                  25
```

<210> SEQ ID NO 5
<211> LENGTH: 28
<212> TYPE: PRT
<213> ORGANISM: Artificial Sequence
<220> FEATURE:
<223> OTHER INFORMATION: Recombinantly produced peptide

<400> SEQUENCE: 5

```
Asn Glu Gln Asp Leu Leu Ala Leu Asp Lys Trp Ala Asn Leu Trp Asn
1               5                   10                  15

Trp Phe Asn Ile Thr Asn Trp Leu Trp Tyr Ile Arg
            20                  25
```

<210> SEQ ID NO 6
<211> LENGTH: 28
<212> TYPE: PRT
<213> ORGANISM: Artificial Sequence
<220> FEATURE:
<223> OTHER INFORMATION: Recombinantly produced peptide

<400> SEQUENCE: 6

```
Asn Glu Gln Glu Leu Leu Glu Leu Asp Lys Trp Ala Ser Leu Trp Asn
1               5                   10                  15

Trp Phe Asp Ile Thr Asn Trp Leu Trp Tyr Ile Lys
            20                  25
```

<210> SEQ ID NO 7
<211> LENGTH: 28
<212> TYPE: PRT
<213> ORGANISM: Artificial Sequence
<220> FEATURE:
<223> OTHER INFORMATION: Recombinantly produced peptide

<400> SEQUENCE: 7

```
Asn Glu Lys Asp Leu Leu Ala Leu Asp Ser Trp Lys Asn Leu Trp Asn
1               5                   10                  15

Trp Phe Asp Ile Thr Asn Trp Leu Trp Tyr Ile Lys
            20                  25
```

<210> SEQ ID NO 8
<211> LENGTH: 28
<212> TYPE: PRT
<213> ORGANISM: Artificial Sequence
<220> FEATURE:
<223> OTHER INFORMATION: Recombinantly produced peptide

<400> SEQUENCE: 8

Asn Glu Gln Asp Leu Leu Ala Leu Asp Ser Trp Glu Asn Leu Trp Asn
1               5                   10                  15

Trp Phe Asp Ile Thr Asn Trp Leu Trp Tyr Ile Lys
            20                  25

<210> SEQ ID NO 9
<211> LENGTH: 28
<212> TYPE: PRT
<213> ORGANISM: Artificial Sequence
<220> FEATURE:
<223> OTHER INFORMATION: Recombinantly produced peptide

<400> SEQUENCE: 9

Asn Glu Gln Glu Leu Leu Glu Leu Asp Lys Trp Ala Ser Leu Trp Asn
1               5                   10                  15

Trp Phe Ser Ile Thr Gln Trp Leu Trp Tyr Ile Lys
            20                  25

<210> SEQ ID NO 10
<211> LENGTH: 28
<212> TYPE: PRT
<213> ORGANISM: Artificial Sequence
<220> FEATURE:
<223> OTHER INFORMATION: Recombinantly produced peptide

<400> SEQUENCE: 10

Asn Glu Gln Glu Leu Leu Ala Leu Asp Lys Trp Ala Ser Leu Trp Asn
1               5                   10                  15

Trp Phe Asp Ile Ser Asn Trp Leu Trp Tyr Ile Lys
            20                  25

<210> SEQ ID NO 11
<211> LENGTH: 28
<212> TYPE: PRT
<213> ORGANISM: Artificial Sequence
<220> FEATURE:
<223> OTHER INFORMATION: Recombinantly produced peptide

<400> SEQUENCE: 11

Asn Glu Gln Asp Leu Leu Ala Leu Asp Lys Trp Asp Asn Leu Trp Ser
1               5                   10                  15

Trp Phe Thr Ile Thr Asn Trp Leu Trp Tyr Ile Lys
            20                  25

<210> SEQ ID NO 12
<211> LENGTH: 28
<212> TYPE: PRT
<213> ORGANISM: Artificial Sequence
<220> FEATURE:
<223> OTHER INFORMATION: Recombinantly produced peptide

<400> SEQUENCE: 12

Asn Glu Gln Asp Leu Leu Ala Leu Asp Lys Trp Ala Ser Leu Trp Asn
1               5                   10                  15

Trp Phe Asp Ile Thr Lys Trp Leu Trp Tyr Ile Lys
            20                  25

<210> SEQ ID NO 13
<211> LENGTH: 28
<212> TYPE: PRT
<213> ORGANISM: Artificial Sequence
<220> FEATURE:
<223> OTHER INFORMATION: Recombinantly produced peptide

```
<400> SEQUENCE: 13

Asn Glu Gln Asp Leu Leu Ala Leu Asp Lys Trp Ala Ser Leu Trp Asn
1               5                   10                  15

Trp Phe Ser Ile Thr Asn Trp Leu Trp Tyr Ile Lys
            20                  25

<210> SEQ ID NO 14
<211> LENGTH: 28
<212> TYPE: PRT
<213> ORGANISM: Artificial Sequence
<220> FEATURE:
<223> OTHER INFORMATION: Recombinantly produced peptide

<400> SEQUENCE: 14

Asn Glu Lys Asp Leu Leu Glu Leu Asp Lys Trp Ala Ser Leu Trp Asn
1               5                   10                  15

Trp Phe Asp Ile Thr Asn Trp Leu Trp Tyr Ile Lys
            20                  25

<210> SEQ ID NO 15
<211> LENGTH: 28
<212> TYPE: PRT
<213> ORGANISM: Artificial Sequence
<220> FEATURE:
<223> OTHER INFORMATION: Recombinantly produced peptide

<400> SEQUENCE: 15

Asn Glu Gln Glu Ile Leu Ala Leu Asp Lys Trp Ala Ser Leu Trp Asn
1               5                   10                  15

Trp Phe Asp Ile Ser Lys Trp Leu Trp Tyr Ile Lys
            20                  25

<210> SEQ ID NO 16
<211> LENGTH: 28
<212> TYPE: PRT
<213> ORGANISM: Artificial Sequence
<220> FEATURE:
<223> OTHER INFORMATION: Recombinantly produced peptide

<400> SEQUENCE: 16

Asn Glu Gln Asp Leu Leu Ala Leu Asp Lys Trp Ala Asn Leu Trp Asn
1               5                   10                  15

Trp Phe Asn Ile Ser Asn Trp Leu Trp Tyr Ile Lys
            20                  25

<210> SEQ ID NO 17
<211> LENGTH: 28
<212> TYPE: PRT
<213> ORGANISM: Artificial Sequence
<220> FEATURE:
<223> OTHER INFORMATION: Recombinantly produced peptide

<400> SEQUENCE: 17

Asn Glu Gln Asp Leu Leu Ala Leu Asp Lys Trp Ala Ser Leu Trp Ser
1               5                   10                  15

Trp Phe Asp Ile Ser Asn Trp Leu Trp Tyr Ile Lys
            20                  25

<210> SEQ ID NO 18
<211> LENGTH: 28
<212> TYPE: PRT
<213> ORGANISM: Artificial Sequence
<220> FEATURE:
<223> OTHER INFORMATION: Recombinantly produced peptide
```

<400> SEQUENCE: 18

Asn Glu Lys Asp Leu Leu Ala Leu Asp Ser Trp Lys Asn Leu Trp Ser
1               5                   10                  15

Trp Phe Asp Ile Thr Asn Trp Leu Trp Tyr Ile Lys
            20                  25

<210> SEQ ID NO 19
<211> LENGTH: 28
<212> TYPE: PRT
<213> ORGANISM: Artificial Sequence
<220> FEATURE:
<223> OTHER INFORMATION: Recombinantly produced peptide

<400> SEQUENCE: 19

Asn Glu Gln Glu Leu Leu Gln Leu Asp Lys Trp Ala Ser Leu Trp Asn
1               5                   10                  15

Trp Phe Ser Ile Thr Asn Trp Leu Trp Tyr Ile Lys
            20                  25

<210> SEQ ID NO 20
<211> LENGTH: 28
<212> TYPE: PRT
<213> ORGANISM: Artificial Sequence
<220> FEATURE:
<223> OTHER INFORMATION: Recombinantly produced peptide

<400> SEQUENCE: 20

Asn Glu Gln Asp Leu Leu Ala Leu Asp Lys Trp Ala Ser Leu Trp Asn
1               5                   10                  15

Trp Phe Asp Ile Ser Asn Trp Leu Trp Tyr Ile Lys
            20                  25

<210> SEQ ID NO 21
<211> LENGTH: 28
<212> TYPE: PRT
<213> ORGANISM: Artificial Sequence
<220> FEATURE:
<223> OTHER INFORMATION: Recombinantly produced peptide

<400> SEQUENCE: 21

Asn Glu Gln Glu Leu Leu Ala Leu Asp Lys Trp Ala Ser Leu Trp Asn
1               5                   10                  15

Trp Phe Asp Ile Ser Asn Trp Leu Trp Tyr Ile Arg
            20                  25

<210> SEQ ID NO 22
<211> LENGTH: 28
<212> TYPE: PRT
<213> ORGANISM: Artificial Sequence
<220> FEATURE:
<223> OTHER INFORMATION: Recombinantly produced peptide

<400> SEQUENCE: 22

Asn Glu Gln Glu Leu Leu Glu Leu Asp Lys Trp Ala Ser Leu Trp Asn
1               5                   10                  15

Trp Phe Asn Ile Thr Asn Trp Leu Trp Tyr Ile Lys
            20                  25

<210> SEQ ID NO 23
<211> LENGTH: 27
<212> TYPE: PRT
<213> ORGANISM: Artificial Sequence
<220> FEATURE:

-continued

<223> OTHER INFORMATION: Recombinantly produced peptide

<400> SEQUENCE: 23

Asn Glu Lys Glu Leu Leu Glu Leu Asp Lys Trp Ala Ser Leu Trp Asn
1               5                   10                  15

Trp Phe Asp Ile Thr Asn Trp Leu Trp Tyr Ile
            20                  25

<210> SEQ ID NO 24
<211> LENGTH: 28
<212> TYPE: PRT
<213> ORGANISM: Artificial Sequence
<220> FEATURE:
<223> OTHER INFORMATION: Recombinantly produced peptide

<400> SEQUENCE: 24

Asn Glu Lys Glu Leu Leu Glu Leu Asp Lys Trp Ala Ser Leu Trp Asn
1               5                   10                  15

Trp Phe Asp Ile Thr Asn Trp Leu Trp Tyr Ile Arg
            20                  25

<210> SEQ ID NO 25
<211> LENGTH: 22
<212> TYPE: PRT
<213> ORGANISM: Artificial Sequence
<220> FEATURE:
<223> OTHER INFORMATION: Recombinantly produced peptide
<220> FEATURE:
<221> NAME/KEY: MISC_FEATURE
<222> LOCATION: (1)..(1)
<223> OTHER INFORMATION: Xaa can be Ala, Ilu, Leu, Val, Phe, Tyr, Trp,
      Met or Pro.
<220> FEATURE:
<221> NAME/KEY: MISC_FEATURE
<222> LOCATION: (10)..(10)
<223> OTHER INFORMATION: Xaa can be Ala, Ilu, Leu, Val, Phe, Tyr, Trp,
      Met or Pro.
<220> FEATURE:
<221> NAME/KEY: MISC_FEATURE
<222> LOCATION: (18)..(18)
<223> OTHER INFORMATION: Xaa can be Ala, Ilu, Leu, Val, Phe, Tyr, Trp,
      Met or Pro.

<400> SEQUENCE: 25

Xaa Phe Ile Met Ile Val Gly Gly Leu Xaa Gly Leu Arg Ile Val Phe
1               5                   10                  15

Thr Xaa Leu Ser Ile Val
            20

<210> SEQ ID NO 26
<211> LENGTH: 22
<212> TYPE: PRT
<213> ORGANISM: Artificial Sequence
<220> FEATURE:
<223> OTHER INFORMATION: Recombinantly produced peptide

<400> SEQUENCE: 26

Ile Phe Ile Met Ile Val Gly Gly Leu Ile Gly Leu Arg Ile Val Phe
1               5                   10                  15

Thr Val Leu Ser Ile Val
            20

<210> SEQ ID NO 27
<211> LENGTH: 22
<212> TYPE: PRT
<213> ORGANISM: Artificial Sequence
<220> FEATURE:

<223> OTHER INFORMATION: Recombinantly produced peptide

<400> SEQUENCE: 27

Leu Phe Ile Met Ile Val Gly Gly Leu Ile Gly Leu Arg Ile Val Phe
1               5                   10                  15

Thr Ala Leu Ser Ile Val
            20

<210> SEQ ID NO 28
<211> LENGTH: 22
<212> TYPE: PRT
<213> ORGANISM: Artificial Sequence
<220> FEATURE:
<223> OTHER INFORMATION: Recombinantly produced peptide

<400> SEQUENCE: 28

Ile Phe Ile Met Ile Val Gly Gly Leu Val Gly Leu Arg Ile Val Phe
1               5                   10                  15

Thr Ala Leu Ser Ile Val
            20

<210> SEQ ID NO 29
<211> LENGTH: 276
<212> TYPE: PRT
<213> ORGANISM: Artificial Sequence
<220> FEATURE:
<223> OTHER INFORMATION: Recombinantly produced peptide

<400> SEQUENCE: 29

Met Lys Thr Ile Ile Ala Leu Ser Tyr Ile Phe Cys Leu Val Phe Ala
1               5                   10                  15

Gln Asp Leu Pro Gly Asn Asp Asn Ser Glu Phe Asn Glu Lys Glu
            20                  25                  30

Leu Leu Glu Leu Asp Lys Trp Ala Ser Leu Trp Asn Trp Phe Asp Ile
        35                  40                  45

Thr Asn Trp Leu Trp Tyr Ile Arg Leu Phe Ile Met Ile Val Gly Gly
    50                  55                  60

Leu Ile Gly Leu Arg Ile Val Phe Ala Val Leu Ser Ile Pro Gln Ser
65                  70                  75                  80

Leu Asp Ser Trp Trp Thr Ser Leu Asn Phe Leu Gly Gly Ser Pro Val
            85                  90                  95

Cys Leu Gly Gln Asn Ser Gln Ser Pro Thr Ser Asn His Ser Pro Thr
            100                 105                 110

Ser Cys Pro Pro Ile Cys Pro Gly Tyr Arg Trp Met Cys Leu Arg Arg
            115                 120                 125

Phe Ile Ile Phe Leu Phe Ile Leu Leu Leu Cys Leu Ile Phe Leu Leu
        130                 135                 140

Val Leu Leu Asp Tyr Gln Gly Met Leu Pro Val Cys Pro Leu Ile Pro
145                 150                 155                 160

Gly Ser Thr Thr Thr Ser Thr Gly Pro Cys Lys Thr Cys Thr Thr Pro
            165                 170                 175

Ala Gln Gly Asn Ser Lys Phe Pro Ser Cys Cys Cys Thr Lys Pro Thr
            180                 185                 190

Asp Gly Asn Cys Thr Cys Ile Pro Ile Pro Ser Ser Trp Ala Phe Ala
            195                 200                 205

Lys Tyr Leu Trp Glu Trp Ala Ser Val Arg Phe Ser Trp Leu Ser Leu
        210                 215                 220

Leu Val Pro Phe Val Gln Trp Phe Val Gly Leu Ser Pro Thr Val Trp

```
                225                 230                 235                 240
Leu Ser Ala Ile Trp Met Met Trp Tyr Trp Gly Pro Ser Leu Tyr Ser
                        245                 250                 255

Ile Val Ser Pro Phe Ile Pro Leu Leu Pro Ile Phe Phe Cys Leu Trp
                    260                 265                 270

Val Tyr Ile Gly
            275

<210> SEQ ID NO 30
<211> LENGTH: 26
<212> TYPE: PRT
<213> ORGANISM: Artificial Sequence
<220> FEATURE:
<223> OTHER INFORMATION: Recombinantly produced peptide

<400> SEQUENCE: 30

Met Lys Thr Ile Ile Ala Leu Ser Tyr Ile Phe Cys Leu Val Phe Ala
1               5                   10                  15

Gln Asp Leu Pro Gly Asn Asp Asn Asn Ser
            20                  25

<210> SEQ ID NO 31
<211> LENGTH: 226
<212> TYPE: PRT
<213> ORGANISM: Artificial Sequence
<220> FEATURE:
<223> OTHER INFORMATION: Recombinantly produced peptide

<400> SEQUENCE: 31

Glu Phe Ile Thr Ser Gly Phe Leu Gly Pro Leu Leu Val Leu Gln Ala
1               5                   10                  15

Gly Phe Phe Leu Leu Thr Arg Ile Leu Thr Ile Pro Gln Ser Leu Asp
                20                  25                  30

Ser Trp Trp Thr Ser Leu Asn Phe Leu Gly Gly Ser Pro Val Cys Leu
            35                  40                  45

Gly Gln Asn Ser Gln Ser Pro Thr Ser Asn His Ser Pro Thr Ser Cys
        50                  55                  60

Pro Pro Ile Cys Pro Gly Tyr Arg Trp Met Cys Leu Arg Arg Phe Ile
65                  70                  75                  80

Ile Phe Leu Phe Ile Leu Leu Cys Leu Ile Phe Leu Leu Val Leu
                85                  90                  95

Leu Asp Tyr Gln Gly Met Leu Pro Val Cys Pro Leu Ile Pro Gly Ser
                100                 105                 110

Thr Thr Thr Ser Thr Gly Pro Cys Lys Thr Cys Thr Thr Pro Ala Gln
            115                 120                 125

Gly Asn Ser Lys Phe Pro Ser Cys Cys Cys Thr Lys Pro Thr Asp Gly
        130                 135                 140

Asn Cys Thr Cys Ile Ser Ile Pro Ser Ser Trp Ala Phe Ala Lys Tyr
145                 150                 155                 160

Leu Trp Glu Trp Ala Ser Val Arg Phe Ser Trp Leu Ser Leu Leu Val
                165                 170                 175

Pro Phe Val Gln Trp Phe Val Gly Leu Ser Pro Thr Val Trp Leu Ser
                180                 185                 190

Ala Ile Trp Met Met Trp Tyr Trp Gly Pro Ser Leu Tyr Ser Ile Val
            195                 200                 205

Ser Pro Phe Ile Pro Leu Leu Pro Ile Phe Phe Cys Leu Trp Val Tyr
        210                 215                 220
```

```
Ile Gly
225

<210> SEQ ID NO 32
<211> LENGTH: 18
<212> TYPE: PRT
<213> ORGANISM: Artificial Sequence
<220> FEATURE:
<223> OTHER INFORMATION: Recombinantly produced peptide

<400> SEQUENCE: 32

Ala Ser Leu Trp Asn Trp Phe Asn Ile Thr Asn Trp Leu Trp Tyr Ala
1               5                   10                  15

Asn Asp

<210> SEQ ID NO 33
<211> LENGTH: 15
<212> TYPE: PRT
<213> ORGANISM: Artificial Sequence
<220> FEATURE:
<223> OTHER INFORMATION: Recombinantly produced peptide

<400> SEQUENCE: 33

Ile Lys Leu Phe Ile Met Ile Val Gly Gly Leu Val Gly Leu Arg
1               5                   10                  15

<210> SEQ ID NO 34
<211> LENGTH: 4
<212> TYPE: PRT
<213> ORGANISM: Artificial Sequence
<220> FEATURE:
<223> OTHER INFORMATION: Recombinantly produced peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 34

Cys Ala Ala Xaa
1

<210> SEQ ID NO 35
<211> LENGTH: 7
<212> TYPE: PRT
<213> ORGANISM: Artificial Sequence
<220> FEATURE:
<223> OTHER INFORMATION: Recombinantly produced peptide

<400> SEQUENCE: 35

Glu Leu Asp Lys Trp Ala Ser
1               5

<210> SEQ ID NO 36
<211> LENGTH: 6
<212> TYPE: PRT
<213> ORGANISM: Artificial Sequence
<220> FEATURE:
<223> OTHER INFORMATION: Recombinantly produced peptide

<400> SEQUENCE: 36

Asn Trp Phe Asp Ile Thr
1               5

<210> SEQ ID NO 37
<211> LENGTH: 4
<212> TYPE: PRT
<213> ORGANISM: Artificial Sequence
```

<220> FEATURE:
<223> OTHER INFORMATION: Recombinantly produced peptide

<400> SEQUENCE: 37

Gly Pro Gly Pro
1

<210> SEQ ID NO 38
<211> LENGTH: 18
<212> TYPE: DNA
<213> ORGANISM: Artificial Sequence
<220> FEATURE:
<223> OTHER INFORMATION: synthetic Oligonucleotide primer

<400> SEQUENCE: 38
ggagctcgtc gacagcaa                                                        18

<210> SEQ ID NO 39
<211> LENGTH: 23
<212> TYPE: DNA
<213> ORGANISM: Artificial Sequence
<220> FEATURE:
<223> OTHER INFORMATION: synthetic Oligonucleotide primer

<400> SEQUENCE: 39
gctctagacc cgatgtacac cca                                                  23

<210> SEQ ID NO 40
<211> LENGTH: 26
<212> TYPE: DNA
<213> ORGANISM: Artificial Sequence
<220> FEATURE:
<223> OTHER INFORMATION: synthetic Oligonucleotide primer

<400> SEQUENCE: 40
gctctagaaa cgagcaggag ctgctg                                               26

<210> SEQ ID NO 41
<211> LENGTH: 36
<212> TYPE: DNA
<213> ORGANISM: Artificial Sequence
<220> FEATURE:
<223> OTHER INFORMATION: synthetic Oligonucleotide primer

<400> SEQUENCE: 41
cgcggatcct caccccttga tgtaccacag ccactt                                    36

<210> SEQ ID NO 42
<211> LENGTH: 33
<212> TYPE: DNA
<213> ORGANISM: Artificial Sequence
<220> FEATURE:
<223> OTHER INFORMATION: synthetic Oligonucleotide primer

<400> SEQUENCE: 42
cgcggatcct caatggtgat ggtgatggtg ggg                                       33

<210> SEQ ID NO 43
<211> LENGTH: 26
<212> TYPE: DNA
<213> ORGANISM: Artificial Sequence
<220> FEATURE:
<223> OTHER INFORMATION: synthetic Oligonucleotide primer

<400> SEQUENCE: 43
gctctagagc cgtggagcgg tacctg                                               26

```
<210> SEQ ID NO 44
<211> LENGTH: 33
<212> TYPE: DNA
<213> ORGANISM: Artificial Sequence
<220> FEATURE:
<223> OTHER INFORMATION: synthetic Oligonucleotide primer

<400> SEQUENCE: 44
ctcggatcct caaatcatga tgaaaatctt gat                           33

<210> SEQ ID NO 45
<211> LENGTH: 30
<212> TYPE: DNA
<213> ORGANISM: Artificial Sequence
<220> FEATURE:
<223> OTHER INFORMATION: synthetic Oligonucleotide primer

<400> SEQUENCE: 45
ctcggatcct cacaccaggc caccaacaat                               30

<210> SEQ ID NO 46
<211> LENGTH: 30
<212> TYPE: DNA
<213> ORGANISM: Artificial Sequence
<220> FEATURE:
<223> OTHER INFORMATION: synthetic Oligonucleotide primer

<400> SEQUENCE: 46
ctcggatcct cacaccagcc tcaggcccac                               30

<210> SEQ ID NO 47
<211> LENGTH: 21
<212> TYPE: DNA
<213> ORGANISM: Artificial Sequence
<220> FEATURE:
<223> OTHER INFORMATION: synthetic Oligonucleotide primer

<400> SEQUENCE: 47
ctcggatcct caggcgggcg c                                        21

<210> SEQ ID NO 48
<211> LENGTH: 48
<212> TYPE: DNA
<213> ORGANISM: Artificial Sequence
<220> FEATURE:
<223> OTHER INFORMATION: synthetic Oligonucleotide primer

<400> SEQUENCE: 48
ccctgcaaga cctgcaccac caccggtcag ggcaactcca agttcccc           48

<210> SEQ ID NO 49
<211> LENGTH: 48
<212> TYPE: DNA
<213> ORGANISM: Artificial Sequence
<220> FEATURE:
<223> OTHER INFORMATION: synthetic Oligonucleotide primer

<400> SEQUENCE: 49
ggggaacttg gagttgccct gaccggtggt ggtgcaggtc ttgcaggg           48

<210> SEQ ID NO 50
<211> LENGTH: 27
<212> TYPE: DNA
<213> ORGANISM: Artificial Sequence
<220> FEATURE:
```

<223> OTHER INFORMATION: synthetic Oligonucleotide primer

<400> SEQUENCE: 50
ggcaccggta acgagcagga gctgctg                                27

<210> SEQ ID NO 51
<211> LENGTH: 33
<212> TYPE: DNA
<213> ORGANISM: Artificial Sequence
<220> FEATURE:
<223> OTHER INFORMATION: synthetic Oligonucleotide primer

<400> SEQUENCE: 51
ggcaccggtc cccttgatgt accacagcca ctt                         33

<210> SEQ ID NO 52
<211> LENGTH: 27
<212> TYPE: DNA
<213> ORGANISM: Artificial Sequence
<220> FEATURE:
<223> OTHER INFORMATION: synthetic Oligonucleotide primer

<400> SEQUENCE: 52
agcgaattca acgagcagga gctgctg                                27

<210> SEQ ID NO 53
<211> LENGTH: 27
<212> TYPE: DNA
<213> ORGANISM: Artificial Sequence
<220> FEATURE:
<223> OTHER INFORMATION: synthetic Oligonucleotide primer

<400> SEQUENCE: 53
cgcggatcct cacccgatgt acaccca                                27

<210> SEQ ID NO 54
<211> LENGTH: 45
<212> TYPE: DNA
<213> ORGANISM: Artificial Sequence
<220> FEATURE:
<223> OTHER INFORMATION: synthetic Oligonucleotide primer

<400> SEQUENCE: 54
caggaagccg gaggtgatga accccttgat gtaccacagc cactt            45

<210> SEQ ID NO 55
<211> LENGTH: 45
<212> TYPE: DNA
<213> ORGANISM: Artificial Sequence
<220> FEATURE:
<223> OTHER INFORMATION: synthetic Oligonucleotide primer

<400> SEQUENCE: 55
aagtggctgt ggtacatcaa ggggttcatc acctccggct cctg             45

<210> SEQ ID NO 56
<211> LENGTH: 276
<212> TYPE: PRT
<213> ORGANISM: Artificial Sequence
<220> FEATURE:
<223> OTHER INFORMATION: Recombinantly produced peptide

<400> SEQUENCE: 56

Met Lys Thr Ile Ile Ala Leu Ser Tyr Ile Phe Cys Leu Val Phe Ala
1               5                   10                  15

```
Gln Asp Leu Pro Gly Asn Asp Asn Asn Ser Glu Phe Ile Thr Ser Gly
             20                  25                  30

Phe Leu Gly Pro Leu Leu Val Leu Gln Ala Gly Phe Phe Leu Leu Thr
         35                  40                  45

Arg Ile Leu Thr Ile Pro Gln Ser Leu Asp Ser Trp Trp Thr Ser Leu
 50                  55                  60

Asn Phe Leu Gly Gly Ser Pro Val Cys Leu Gly Gln Asn Ser Gln Ser
 65                  70                  75                  80

Pro Thr Ser Asn His Ser Pro Thr Ser Cys Pro Pro Ile Cys Pro Gly
             85                  90                  95

Tyr Arg Trp Met Cys Leu Arg Arg Phe Ile Ile Phe Leu Phe Ile Leu
            100                 105                 110

Leu Leu Cys Leu Ile Phe Leu Leu Val Leu Leu Asp Tyr Gln Gly Met
            115                 120                 125

Leu Pro Val Cys Pro Leu Ile Pro Gly Ser Thr Thr Thr Ser Thr Gly
130                 135                 140

Pro Cys Lys Thr Cys Thr Thr Pro Ala Gln Gly Asn Ser Lys Phe Pro
145                 150                 155                 160

Ser Cys Cys Cys Thr Lys Pro Thr Asp Gly Asn Cys Thr Cys Ile Ser
                165                 170                 175

Ile Asn Glu Lys Glu Leu Leu Glu Leu Asp Lys Trp Ala Ser Leu Trp
            180                 185                 190

Asn Trp Phe Asp Ile Thr Asn Trp Leu Trp Ser Ser Leu Trp Ala Ile
                195                 200                 205

Lys Tyr Leu Trp Glu Trp Ala Ser Val Arg Phe Ser Trp Leu Ser Leu
210                 215                 220

Leu Val Pro Phe Val Gln Trp Phe Val Gly Leu Ser Pro Thr Val Trp
225                 230                 235                 240

Leu Ser Ala Ile Trp Met Met Trp Tyr Trp Gly Pro Ser Leu Tyr Ser
                245                 250                 255

Ile Val Ser Pro Phe Ile Pro Leu Leu Pro Ile Phe Phe Cys Leu Trp
                260                 265                 270

Val Tyr Ile Gly
            275

<210> SEQ ID NO 57
<211> LENGTH: 271
<212> TYPE: PRT
<213> ORGANISM: Artificial Sequence
<220> FEATURE:
<223> OTHER INFORMATION: Recombinantly produced peptide

<400> SEQUENCE: 57

Met Lys Thr Ile Ile Ala Leu Ser Tyr Ile Phe Cys Leu Val Phe Ala
 1               5                  10                  15

Gln Asp Leu Pro Gly Asn Asp Asn Ser Glu Phe Ile Thr Ser Gly
             20                  25                  30

Phe Leu Gly Pro Leu Leu Val Leu Gln Ala Gly Phe Phe Leu Leu Thr
         35                  40                  45

Arg Ile Leu Thr Ile Pro Gln Ser Leu Asp Ser Trp Trp Thr Ser Leu
 50                  55                  60

Asn Phe Leu Gly Gly Ser Pro Val Cys Leu Gly Gln Asn Ser Gln Ser
 65                  70                  75                  80

Pro Thr Ser Asn His Ser Pro Thr Ser Cys Pro Pro Ile Cys Pro Gly
             85                  90                  95
```

```
Tyr Arg Trp Met Cys Leu Arg Phe Ile Ile Phe Leu Phe Ile Leu
            100                 105                 110

Leu Leu Cys Leu Ile Phe Leu Leu Val Leu Leu Asp Tyr Gln Gly Met
        115                 120                 125

Leu Pro Val Cys Pro Leu Ile Pro Gly Ser Thr Thr Thr Ser Thr Gly
    130                 135                 140

Pro Cys Lys Thr Cys Thr Thr Pro Ala Gln Gly Asn Ser Lys Phe Pro
145                 150                 155                 160

Ser Cys Cys Cys Thr Lys Pro Thr Asp Gly Asn Cys Thr Cys Ile Asn
                165                 170                 175

Ile Asn Glu Lys Glu Leu Leu Glu Leu Asp Lys Trp Ala Ser Leu Trp
            180                 185                 190

Asn Trp Phe Asp Ile Thr Asn Trp Leu Trp Tyr Ile Arg Leu Phe Ile
        195                 200                 205

Met Ile Val Gly Gly Leu Ile Gly Leu Arg Ile Val Phe Ala Val Leu
    210                 215                 220

Ser Ile Val Val Gly Leu Ser Pro Thr Val Trp Leu Ser Ala Ile Trp
225                 230                 235                 240

Met Met Trp Tyr Trp Gly Pro Ser Leu Tyr Ser Ile Val Ser Pro Phe
                245                 250                 255

Ile Pro Leu Leu Pro Ile Phe Phe Cys Leu Trp Val Tyr Ile Gly
            260                 265                 270

<210> SEQ ID NO 58
<211> LENGTH: 295
<212> TYPE: PRT
<213> ORGANISM: Artificial Sequence
<220> FEATURE:
<223> OTHER INFORMATION: Recombinantly produced peptide

<400> SEQUENCE: 58

Met Lys Thr Ile Ile Ala Leu Ser Tyr Ile Phe Cys Leu Val Phe Ala
1               5                   10                  15

Gln Asp Leu Pro Gly Asn Asp Asn Ser Glu Phe Asn Glu Lys Glu
            20                  25                  30

Leu Leu Glu Leu Asp Lys Trp Ala Ser Leu Trp Asn Trp Phe Asp Ile
        35                  40                  45

Thr Asn Trp Leu Trp Tyr Ile Arg Leu Phe Ile Met Ile Val Gly Gly
    50                  55                  60

Leu Ile Gly Leu Arg Ile Val Phe Ala Val Leu Ser Ile Pro Gln Ser
65                  70                  75                  80

Leu Asp Ser Trp Trp Thr Ser Leu Asn Phe Leu Gly Gly Ser Pro Val
                85                  90                  95

Cys Leu Gly Gln Asn Ser Gln Ser Pro Thr Ser Asn His Ser Pro Thr
            100                 105                 110

Ser Cys Pro Pro Ile Cys Pro Gly Tyr Arg Trp Met Cys Leu Arg Arg
        115                 120                 125

Phe Ile Ile Phe Leu Phe Ile Leu Leu Leu Cys Leu Ile Phe Leu Leu
    130                 135                 140

Val Leu Leu Asp Tyr Gln Gly Met Leu Pro Val Cys Pro Leu Ile Pro
145                 150                 155                 160

Gly Ser Thr Thr Thr Ser Thr Gly Pro Cys Lys Thr Cys Thr Thr Pro
                165                 170                 175

Ala Gln Gly Asn Ser Lys Phe Pro Ser Cys Cys Cys Thr Lys Pro Thr
            180                 185                 190
```

Asp Gly Asn Cys Thr Cys Ile Pro Ile Asn Glu Lys Glu Leu Leu Glu
            195                 200                 205

Leu Asp Lys Trp Ala Ser Leu Trp Asn Trp Phe Asp Ile Thr Asn Trp
        210                 215                 220

Leu Trp Tyr Ile Arg Leu Phe Ile Met Ile Val Gly Gly Leu Ile Gly
225                 230                 235                 240

Leu Arg Ile Val Phe Ala Val Leu Ser Ile Val Val Gly Leu Ser Pro
                245                 250                 255

Thr Val Trp Leu Ser Ala Ile Trp Met Met Trp Tyr Trp Gly Pro Ser
            260                 265                 270

Leu Tyr Ser Ile Val Ser Pro Phe Ile Pro Leu Leu Pro Ile Phe Phe
        275                 280                 285

Cys Leu Trp Val Tyr Ile Gly
        290                 295

<210> SEQ ID NO 59
<211> LENGTH: 1730
<212> TYPE: DNA
<213> ORGANISM: Artificial Sequence
<220> FEATURE:
<223> OTHER INFORMATION: Recombinantly produced nuceic acid sequence

<400> SEQUENCE: 59

```
ggtaccgtcg acagcaaaag caggggataa ttctattaac catgaagact atcattgctt     60
ccatggcagc tgtcgttttc gtcccctatt aagataattg gtacttctga tagtaacgaa    120
tgagctacat tttctgtctg gttttcgccc aagaccttcc aggaaatgac aacaacagcg    180
actcgatgta aaagacagac caaaagcggg ttctggaagg tcctttactg ttgttgtcgc    240
aattcatcac ctccggcttc ctgggccccc tgctggtcct gcaggccggg ttcttcctgc    300
ttaagtagtg gaggccgaag gacccggggg acgaccagga cgtccggccc aagaaggacg    360
tgacccgcat cctcaccatc ccccagtccc tggactcgtg gtggacctcc ctcaactttc    420
actgggcgta ggagtggtag ggggtcaggg acctgagcac cacctggagg gagttgaaag    480
tggggggctc cccgtgtgt ctgggccaga actcccagtc ccccacctcc aaccactccc    540
acccccgag gggcacaca  acccggtct tgagggtcag ggggtggagg ttggtgaggg    600
ccacctcctg ccccccccatc tgccccggct accgctggat gtgcctgcgc cgcttcatca    660
ggtggaggac gggggggtag acggggccga tggcgaccta cacggacgcg gcgaagtagt    720
tcttcctgtt catcctgctg ctgtgcctga tcttcctgct ggtgctgctg gactaccagg    780
agaaggacaa gtaggacgac gacacggact agaaggacga ccacgacgac ctgatggtcc    840
gcatgctgcc cgtgtgcccc ctgatccccg gctccaccac cacctccacc ggcccctgca    900
cgtacgacgg gcacacgggg gactaggggc cgaggtggtg gtggaggtgg ccggggacgt    960
agacctgcac cacccccgcc cagggcaact ccaagttccc ctcctgctgc tgcaccaagc   1020
tctggacgtg gtgggggcgg gtcccgttga ggttcaaggg gaggacgacg acgtggttcg   1080
ccaccgacgg caactgcacc tgcatcaata ttaatgaaaa agaattattg gaattggata   1140
ggtggctgcc gttgacgtgg acgtagttat aattactttt tcttaataac cttaacctat   1200
aatgggcaag tttgtggaat tggtttgaca taacaaactg gctgtggtat ataagattat   1260
ttacccgttc aaacacctta accaaactgt attgtttgac cgacaccata tattctaata   1320
tcataatgat agtaggaggc ttgataggtt taagaatagt ttttgctgta ctttctatag   1380
agtattacta tcatcctccg aactatccaa attcttatca aaaacgacat gaaagatatc   1440
```

```
tagtgggcct gtcccccacc gtgtggctgt ccgccatctg gatgatgtgg tactggggcc    1500
atcacccgga caggggtgg cacaccgaca ggcggtagac ctactacacc atgaccccgg    1560
cctccctgta ctccatcgtg tccccttca tccccctgct gcccatcttc ttctgcctgt    1620
ggagggacat gaggtagcac aggggggaagt aggggggacga cgggtagaag aagacggaca    1680
gggtgtacat ctgactagtg agctccccac atgtagactg atcactcgag               1730
```

<210> SEQ ID NO 60
<211> LENGTH: 15
<212> TYPE: PRT
<213> ORGANISM: Artificial Sequence
<220> FEATURE:
<223> OTHER INFORMATION: Recombinantly produced peptide

<400> SEQUENCE: 60

```
Asn Glu Lys Glu Leu Leu Glu Leu Asp Lys Trp Ala Ser Leu Trp
1               5                   10                  15
```

<210> SEQ ID NO 61
<211> LENGTH: 25
<212> TYPE: PRT
<213> ORGANISM: Artificial Sequence
<220> FEATURE:
<223> OTHER INFORMATION: Recombinantly produced peptide

<400> SEQUENCE: 61

```
Asn Glu Lys Glu Leu Leu Glu Leu Asp Lys Trp Ala Ser Leu Trp Asn
1               5                   10                  15

Trp Phe Asp Ile Thr Asn Trp Leu Trp
                20                  25
```

<210> SEQ ID NO 62
<211> LENGTH: 300
<212> TYPE: PRT
<213> ORGANISM: Artificial Sequence
<220> FEATURE:
<223> OTHER INFORMATION: Recombinantly produced peptide

<400> SEQUENCE: 62

```
Met Lys Thr Ile Ile Ala Leu Ser Tyr Ile Phe Cys Leu Val Phe Ala
1               5                   10                  15

Gln Asp Leu Pro Gly Asn Asp Asn Ser Glu Phe Asn Glu Lys Glu
            20                  25                  30

Leu Leu Glu Leu Asp Lys Trp Ala Ser Leu Trp Asn Trp Phe Asp Ile
            35                  40                  45

Thr Asn Trp Leu Trp Tyr Ile Arg Leu Phe Ile Met Ile Val Gly Gly
        50                  55                  60

Leu Ile Gly Leu Arg Ile Val Phe Ala Val Leu Ser Ile Pro Gln Ser
65              70                  75                  80

Leu Asp Ser Trp Trp Thr Ser Leu Asn Phe Leu Gly Gly Ser Pro Val
            85                  90                  95

Cys Leu Gly Gln Asn Ser Gln Ser Pro Thr Ser Asn His Ser Pro Thr
            100                 105                 110

Ser Cys Pro Pro Ile Cys Pro Gly Tyr Arg Trp Met Cys Leu Arg Arg
            115                 120                 125

Phe Ile Ile Phe Leu Phe Ile Leu Leu Leu Cys Leu Ile Phe Leu Leu
        130                 135                 140

Val Leu Leu Asp Tyr Gln Gly Met Leu Pro Val Cys Pro Leu Ile Pro
145             150                 155                 160
```

```
Gly Ser Thr Thr Thr Ser Thr Gly Pro Cys Lys Thr Cys Thr Thr Pro
            165                 170                 175

Ala Gln Gly Asn Ser Lys Phe Pro Ser Cys Cys Cys Thr Lys Pro Thr
        180                 185                 190

Asp Gly Asn Cys Thr Cys Ile Ser Ile Asn Glu Lys Glu Leu Leu Glu
            195                 200                 205

Leu Asp Lys Trp Ala Ser Leu Trp Asn Trp Phe Asp Ile Thr Asn Trp
    210                 215                 220

Leu Trp Ser Ser Leu Trp Ala Ile Lys Tyr Leu Trp Glu Trp Ala Ser
225                 230                 235                 240

Val Arg Phe Ser Trp Leu Ser Leu Leu Val Pro Phe Val Gln Trp Phe
                245                 250                 255

Val Gly Leu Ser Pro Thr Val Trp Leu Ser Ala Ile Trp Met Met Trp
                260                 265                 270

Tyr Trp Gly Pro Ser Leu Tyr Ser Ile Val Ser Pro Phe Ile Pro Leu
                275                 280                 285

Leu Pro Ile Phe Phe Cys Leu Trp Val Tyr Ile Gly
    290                 295                 300

<210> SEQ ID NO 63
<211> LENGTH: 313
<212> TYPE: PRT
<213> ORGANISM: Artificial Sequence
<220> FEATURE:
<223> OTHER INFORMATION: Recombinantly produced peptide

<400> SEQUENCE: 63

Met Lys Thr Ile Ile Ala Leu Ser Tyr Ile Phe Cys Leu Val Phe Ala
1               5                   10                  15

Gln Asp Leu Pro Gly Asn Asp Asn Ser Glu Phe Ile Thr Ser Gly
            20                  25                  30

Phe Leu Gly Pro Leu Leu Val Leu Gln Ala Gly Phe Phe Leu Leu Thr
        35                  40                  45

Arg Ile Leu Thr Ile Pro Gln Ser Leu Asp Ser Trp Trp Thr Ser Leu
    50                  55                  60

Asn Phe Leu Gly Gly Ser Pro Val Cys Leu Gly Gln Asn Ser Gln Ser
65                  70                  75                  80

Pro Thr Ser Asn His Ser Pro Thr Ser Cys Pro Pro Ile Cys Pro Gly
                85                  90                  95

Tyr Arg Trp Met Cys Leu Arg Arg Phe Ile Ile Phe Leu Phe Ile Leu
                100                 105                 110

Leu Leu Cys Leu Ile Phe Leu Leu Val Leu Leu Asp Tyr Gln Gly Met
            115                 120                 125

Leu Pro Val Cys Pro Leu Ile Pro Gly Ser Thr Thr Thr Ser Thr Gly
    130                 135                 140

Pro Cys Lys Thr Cys Thr Thr Pro Ala Gln Gly Asn Ser Lys Phe Pro
145                 150                 155                 160

Ser Cys Cys Cys Thr Lys Pro Thr Asp Gly Asn Cys Thr Cys Ile Ser
                165                 170                 175

Ile Asn Glu Lys Glu Leu Leu Glu Leu Asp Lys Trp Ala Ser Leu Trp
            180                 185                 190

Ala Ile Asn Glu Lys Glu Leu Leu Glu Leu Asp Lys Trp Ala Ser Leu
        195                 200                 205

Trp Ala Ile Asn Glu Lys Glu Leu Leu Glu Leu Asp Lys Trp Ala Ser
    210                 215                 220
```

```
Leu Trp Ala Ile Asn Glu Lys Glu Leu Leu Glu Leu Asp Lys Trp Ala
225                 230                 235                 240

Ser Leu Trp Ala Ile Lys Tyr Leu Trp Glu Trp Ala Ser Val Arg Phe
                245                 250                 255

Ser Trp Leu Ser Leu Leu Val Pro Phe Val Gln Trp Phe Val Gly Leu
            260                 265                 270

Ser Pro Thr Val Trp Leu Ser Ala Ile Trp Met Met Trp Tyr Trp Gly
        275                 280                 285

Pro Ser Leu Tyr Ser Ile Val Ser Pro Phe Ile Pro Leu Leu Pro Ile
    290                 295                 300

Phe Phe Cys Leu Trp Val Tyr Ile Gly
305                 310
```

<210> SEQ ID NO 64
<211> LENGTH: 337
<212> TYPE: PRT
<213> ORGANISM: Artificial Sequence
<220> FEATURE:
<223> OTHER INFORMATION: Recombinantly produced peptide

<400> SEQUENCE: 64

```
Met Lys Thr Ile Ile Ala Leu Ser Tyr Ile Phe Cys Leu Val Phe Ala
1               5                   10                  15

Gln Asp Leu Pro Gly Asn Asp Asn Ser Glu Phe Asn Glu Lys Glu
            20                  25                  30

Leu Leu Glu Leu Asp Lys Trp Ala Ser Leu Trp Asn Trp Phe Asp Ile
                35                  40                  45

Thr Asn Trp Leu Trp Tyr Ile Arg Leu Phe Ile Met Ile Val Gly Gly
    50                  55                  60

Leu Ile Gly Leu Arg Ile Val Phe Ala Val Leu Ser Ile Pro Gln Ser
65                  70                  75                  80

Leu Asp Ser Trp Trp Thr Ser Leu Asn Phe Leu Gly Gly Ser Pro Val
                85                  90                  95

Cys Leu Gly Gln Asn Ser Gln Ser Pro Thr Ser Asn His Ser Pro Thr
            100                 105                 110

Ser Cys Pro Pro Ile Cys Pro Gly Tyr Arg Trp Met Cys Leu Arg Arg
                115                 120                 125

Phe Ile Ile Phe Leu Phe Ile Leu Leu Leu Cys Leu Ile Phe Leu Leu
130                 135                 140

Val Leu Leu Asp Tyr Gln Gly Met Leu Pro Val Cys Pro Leu Ile Pro
145                 150                 155                 160

Gly Ser Thr Thr Thr Ser Thr Gly Pro Cys Lys Thr Cys Thr Thr Pro
                165                 170                 175

Ala Gln Gly Asn Ser Lys Phe Pro Ser Cys Cys Cys Thr Lys Pro Thr
            180                 185                 190

Asp Gly Asn Cys Thr Cys Ile Ser Ile Asn Glu Lys Glu Leu Leu Glu
                195                 200                 205

Leu Asp Lys Trp Ala Ser Leu Trp Ala Ile Asn Glu Lys Glu Leu Leu
    210                 215                 220

Glu Leu Asp Lys Trp Ala Ser Leu Trp Ala Ile Asn Glu Lys Glu Leu
225                 230                 235                 240

Leu Glu Leu Asp Lys Trp Ala Ser Leu Trp Ala Ile Asn Glu Lys Glu
                245                 250                 255

Leu Leu Glu Leu Asp Lys Trp Ala Ser Leu Trp Ala Ile Lys Tyr Leu
            260                 265                 270
```

-continued

```
Trp Glu Trp Ala Ser Val Arg Phe Ser Trp Leu Ser Leu Leu Val Pro
    275                 280                 285

Phe Val Gln Trp Phe Val Gly Leu Ser Pro Thr Val Trp Leu Ser Ala
    290                 295                 300

Ile Trp Met Met Trp Tyr Trp Gly Pro Ser Leu Tyr Ser Ile Val Ser
305                 310                 315                 320

Pro Phe Ile Pro Leu Leu Pro Ile Phe Phe Cys Leu Trp Val Tyr Ile
            325                 330                 335

Gly
```